United States Patent
Zhang et al.

(10) Patent No.: US 12,227,581 B2
(45) Date of Patent: *Feb. 18, 2025

(54) ANTI-BCMA SINGLE DOMAIN ANTIBODIES AND APPLICATION THEREOF

(71) Applicant: SHENZHEN PREGENE BIOPHARMA CO. LTD., Shenzhen (CN)

(72) Inventors: Jishuai Zhang, Shenzhen (CN); Hongjian Li, Shenzhen (CN); Chaolemeng Bao, Shenzhen (CN); Qinghua Cai, Shenzhen (CN); Yingying Li, Shenzhen (CN); Zongpei Song, Shenzhen (CN); Yijin Ding, Shenzhen (CN); Zhibo Cai, Shenzhen (CN)

(73) Assignee: SHENZHEN PREGENE BIOPHARMA CO., LTD., Shenzhen (CN)

( * ) Notice: Subject to any disclaimer, the term of this patent is extended or adjusted under 35 U.S.C. 154(b) by 840 days.

This patent is subject to a terminal disclaimer.

(21) Appl. No.: 17/270,788

(22) PCT Filed: Jul. 10, 2019

(86) PCT No.: PCT/CN2019/095507
§ 371 (c)(1),
(2) Date: Feb. 23, 2021

(87) PCT Pub. No.: WO2020/038147
PCT Pub. Date: Feb. 27, 2020

(65) Prior Publication Data
US 2022/0251226 A1 Aug. 11, 2022

(30) Foreign Application Priority Data

Aug. 24, 2018 (CN) .......................... 201810972054.2

(51) Int. Cl.
| | | |
|---|---|---|
| *C07K 16/28* | (2006.01) | |
| *A61K 39/00* | (2006.01) | |
| *A61P 35/00* | (2006.01) | |
| *C12N 5/0783* | (2010.01) | |

(52) U.S. Cl.
CPC ...... *C07K 16/2878* (2013.01); *A61K 39/4611* (2023.05); *A61K 39/4631* (2023.05); *A61K 39/464417* (2023.05); *A61P 35/00* (2018.01); *C12N 5/0636* (2013.01); *C12N 5/0638* (2013.01); *C07K 2317/24* (2013.01); *C07K 2317/565* (2013.01); *C07K 2317/569* (2013.01); *C07K 2317/76* (2013.01); *C07K 2319/33* (2013.01)

(58) Field of Classification Search
CPC .......... C07K 16/2878; C07K 2317/565; C07K 2317/569; C07K 2317/22; A61K 39/4631; A61K 39/464417
See application file for complete search history.

(56) References Cited

U.S. PATENT DOCUMENTS

| | | |
|---|---|---|
| 10,174,095 B2 | 1/2019 | Brogdon et al. |
| 10,383,929 B2 | 8/2019 | Morgan et al. |
| 2016/0046724 A1 | 2/2016 | Brogdon et al. |
| 2017/0226216 A1* | 8/2017 | Morgan .................. A61P 37/08 |
| 2018/0085444 A1 | 3/2018 | Morgan et al. |
| 2018/0094280 A1 | 4/2018 | Kutner et al. |
| 2018/0230225 A1 | 8/2018 | Fan et al. |
| 2019/0153061 A1 | 5/2019 | Brogdon et al. |
| 2020/0078399 A1 | 3/2020 | Fan et al. |
| 2021/0163615 A1 | 6/2021 | Fan et al. |
| 2021/0261675 A1 | 8/2021 | Fan et al. |
| 2022/0127371 A1 | 4/2022 | Fan et al. |
| 2022/0218746 A1 | 7/2022 | Zhang. et al. |

FOREIGN PATENT DOCUMENTS

| | | |
|---|---|---|
| CN | 105384825 A | 3/2016 |
| CN | 105777911 A | 7/2016 |
| CN | 105837693 A | 8/2016 |
| CN | 106687483 A | 5/2017 |
| CN | 106795217 A | 5/2017 |
| CN | 107207598 A | 9/2017 |
| CN | 107614008 A | 1/2018 |
| CN | 109134665 A | 1/2019 |
| CN | 109694413 A | 4/2019 |
| EP | 3 842 462 A1 | 6/2021 |

(Continued)

OTHER PUBLICATIONS

Mariuzza (Annu. Rev. Biophys. Biophys. Chem., 16: 139-159, 1987) (Year: 1987).*
Hasegawa et al (Single amino acid substitution in LC-CDR1 induces Russell body phenotype that attenuates cellular protein synthesis through eIF2α phosphorylation and thereby downregulates IgG secretion despite operational secretory pathway traffic. MAbs. Jul. 2017;9(5):854-873) (Year: 2017).*
Al Qaraghuli et al. (2020, Nature Scientific Reports 10:13969) (Year: 2020).*

(Continued)

*Primary Examiner* — Elizabeth C. Kemmerer
*Assistant Examiner* — Ashley H. Gao
(74) *Attorney, Agent, or Firm* — Merchant & Gould P.C.; Daniel J. Pereira

(57) ABSTRACT

A group of anti-BCMA single domain antibodies, as well as genes of the single domain antibodies in the group, a vector containing the single domain antibodies in the group, a chimeric antigen receptor, and a T cell modified by a chimeric antigen receptor, and detection and treatment application of the single domain antibodies in the group. The anti-BCMA single domain antibodies have high activity, high stability, high specificity, and high binding capability.

11 Claims, 4 Drawing Sheets

Specification includes a Sequence Listing.

(56) References Cited

FOREIGN PATENT DOCUMENTS

| KR | 10-2018-0035918 | | 4/2018 |
|----|-----------------|---|--------|
| WO | WO 2017/025038 | A1 | 2/2017 |
| WO | WO 2018/028647 | A1 | 2/2018 |
| WO | WO 2018/119215 | A1 | 6/2018 |
| WO | WO 2020/038146 | A1 | 2/2020 |

OTHER PUBLICATIONS

Lloyd et al. (2009, Protein Engineering, Eng. Design & Selection 22(3): 159-168) (Year: 2009).*
Khan et al. (2014, J. Immunol. 192: 5398-5405) (Year: 2014).*
Coquery et al (Regulatory roles of the tumor necrosis factor receptor BCMA. Crit Rev Immunol. 2012;32(4):287-305) (Year: 2012).*
American Cancer Society (Multiple Myeloma Causes, Risk Factors, and Prevention; https://www.cancer.org/cancer/types/multiple-myeloma/causes-risks-prevention/prevention.html (2020)) (Year: 2020).*
McCarthy et al. (J. Immunol. Methods, 251(1-2): 137-149, 2001) (Year: 2001).*
Lin et al. (African Journal of Biotechnology, 10(79):18294-18302, 2011) (Year: 2011).*
Wu, W. et al., "A Novel VHH Antibody Targeting the B Cell-Activating Factor for B-Cell Lymphoma," International Journal of Molecular Sciences, ISSN 1422-0067, 2014, vol. 15, pp. 9481-9496.
Tai, Y-T. et al., "Targeting B-cell maturation antigen in multiple myeloma," Immunotherapy, 2015, vol. 7, No. 11, pp. 1187-1199.
International Search Report issued on Oct. 10, 2019 in PCT/CN2019/095507 filed on Jul. 10, 2019, 5 pages.
Extended European Search Report issued Aug. 9, 2022 in European Patent Application No. 19852395.3, 10 pages.
Japanese Office Action issued Jun. 3, 2022 in Japanese Patent Application No. 2021-534412, 6 pages.
Singaporean Office Action and Search Report issued Oct. 5, 2022 in Singaporean Patent Application No. 11202101675U, 8 pages.
Eurasian Office Action issued Oct. 31, 2022 in Eurasian Patent Application No. 202190608 (with English language translation), 6 pages.
Norris Lam, et al., "T Cells Expressing Anti-B-Cell Maturation Antigen (BCMA) Chimeric Antigen Receptors with Antigen Recognition Domains Made up of Only Single Human Heavy Chain Variable Domains Specifically Recognize BCMA and Eradicate Tumors in Mice," Blood, No. 130, Supplement 1: 504, Dec. 7, 2017, 3 pages.
McKay Brown, et al., "Tolerance to Single, but Not Multiple, Amino Acid Replacements in Antibody $V_H$ CDR2," The Journal of Immunology, 1996, pp. 3285-3291.

* cited by examiner

ANTI-BCMA SINGLE DOMAIN ANTIBODIES AND APPLICATION THEREOF

CROSS-REFERENCE TO RELATED APPLICATIONS

This application is a National Stage Application and claims priority under 35 U.S.C. § 371 to Patent Cooperation Treaty application PCT/CN2019/095507, filed Jul. 10, 2019, which claims the benefit of CN application No. 201810972054.2, filed Aug. 24, 2018. Priority is claimed to these applications and the disclosures of these prior applications are considered part of the disclosure of this application and to the extent allowed the entire contents of the aforementioned applications are incorporated herein.

TECHNICAL FIELD

The present disclosure belongs to the field of biotechnologies. In particular, the present disclosure relates to a group of single domain antibodies against B cell maturation antigen (BCMA) and use thereof.

BACKGROUND

BCMA (B cell maturation antigen, BCMA) is a member of tumor necrosis factor receptor (TNFR) superfamily, which can bind to a B cell-activating factor (BAFF) or a B lymphocyte stimulator (BLyS) and a proliferation inducing ligand (APRIL). It is reported that in normal cells. BCMA is mainly expressed by plasmocytes and some mature B cells, but not expressed in most B cells or other organs. Multiple myeloma (MM) is a malignant tumor characterized by massive proliferation of clonal plasmocytes. The RNA of BCMA is generally detected in MM cells, and the BCMA protein can be detected on the surfaces of plasmocytes of a patient with multiple myeloma. Accordingly, a candidate target antigen for immune treatment of MM is BCMA. At present, MM treatment can induce remission, but almost all the patients will eventually relapse and die. Some monoclonal antibody candidate drugs have shown a promise to treat MM in pre-clinical studies and early clinical trials, but have not been universally approved by consensus, and no monoclonal antibody drug has been marketed. Clearly, there is an urgent need of new immunological therapy for MM, and an effective antigen-specific adoptive T cell therapy developed for this disease will be an important research progress.

Single domain antibody (sdAb), also known as nanobody, is a heavy chain antibody found in Alpaca blood in which a light chain is absent. By using the molecular biology technology in combination with nano-particle science, Belgian scientists have developed a novel, low molecular weight fragment of antibody which can bind to an antigen. It has a group of advantages, such as, simple structure, strong penetration, easy expression and purification, high affinity and stability, and no toxic and side reactions, or the like. Single domain antibodies for various target antigens have been researched by use of a single domain antibody platform technology, and then used in the field of biomedicines.

The present disclosure aims to develop a group of promising anti-BCMA single domain antibodies for use in therapeutic antibody candidate drugs and chimeric antigen receptor T cells targeting BCMA.

SUMMARY OF THE INVENTION

The technical problem to be solved by the present disclosure is to provide a group of novel anti-BCMA single domain antibodies having good effects.

Another technical problem to be solved by the present disclosure is to develop various uses of anti-BCMA single domain antibodies.

In order to achieve the above objects, the present disclosure provides the following technical solutions:

The present disclosure provides a group of anti-BCMA single domain antibodies composed of a framework region and a complementarity determining region, wherein the complementarity determining region has an amino acid sequence selected from those of SEQ ID NOs: 1-66 (Annex 1: Amino Acid Sequences of Complementarity Determining Regions of Screened BCMA-sdAbs).

In some embodiments, the amino acid sequence of the complementarity determining region has more than 80%, more than 85%, more than 90%, more than 95% or more than 99% identity to the amino acid sequence as set forth in SEQ ID NOs: 1-66.

Preferably, the difference in amino acids is conservative substitution.

In some embodiments, the single domain antibody in the group has an amino acid sequence selected from SEQ ID NOs: 67-132 or is an amino acid sequence selected from SEQ ID NOs: 67-132 (Annex 2: Amino Acid Sequences of Screened BCMA-sdAbs).

In some embodiments, the amino acid sequence of the single domain antibody has more than 80%, more than 85%, more than 90%, more than 95% or more than 99% identity to the amino acid sequence as set forth in SEQ ID NOs: 67-132.

Preferably, the difference in amino acids is conservative substitution, more preferably, one or more conservative substitutions.

The present disclosure provides a group of genes of anti-BCMA single domain antibodies having a nucleotide sequence selected from those of SEQ ID NOs: 133-198 (Annex 3: Nucleotide Sequences of Screened BCMA-sdAbs), or being a nucleotide sequence of SEQ ID NOs: 133-198, or being a nucleotide sequence encoding the above single domain antibodies.

In some embodiments, the nucleotide sequence of the single domain antibody has more than 80%, more than 85%, more than 90%, more than 95% or more than 99% identity to the nucleotide sequence as set forth in SEQ ID NOs: 133-198.

Preferably, the difference in bases is conservative substitution, more preferably, one or more conservative substitutions.

The present disclosure provides a polypeptide having one or more single domain antibodies selected from the group of single domain antibodies as described above.

Preferably, the plurality of single domain antibodies are the same or different.

The present disclosure provides an expression vector including one or more genes selected from the group of genes of single domain antibodies as described above.

Preferably, the expression vector is a prokaryotic cell expression vector, a eukaryotic cell expression vector, or other cell expression vector(s).

The present disclosure provides a host cell including the above expression vector.

Preferably, the host cell is a prokaryotic expression cell, a eukaryotic expression cell, a fungus cell or a yeast cell, wherein the prokaryotic expression cell is preferably *Escherichia coli*.

The present disclosure provides a chimeric antigen receptor, having one or multiple single domain antibodies selected from the above group of single domain antibodies.

Preferably, the multiple single domain antibodies are the same or different.

The present disclosure provides a T cell modified by a chimeric antigen receptor, which is modified by the above chimeric antigen receptor.

The present disclosure provides a pharmaceutical composition including one or more single domain antibodies selected from the above group of single domain antibodies as active ingredients.

The present disclosure provides a humanized anti-BCMA single domain antibody, which is obtained by humanizing the single domain antibody selected from the above group of single domain antibodies.

The present disclosure provides use of the single domain antibody in the above group of single domain antibodies in detection of BCMA.

The present disclosure provides use of the single domain antibody in the above group of single domain antibodies for blocking an interaction between BAFF and BCMA.

In some embodiments, the single domain antibody is linked to one or more of a cytotoxic agent, an enzyme, a radioisotope, a fluorescent compound or a chemiluminescent compound.

The present disclosure provides use of the single domain antibody in the above group of single domain antibodies in preparation of a drug for treating a disease associated with abnormal BCMA expression.

Preferably, the disease associated with abnormal BCMA expression is a multiple myeloma disease.

The present disclosure has the following beneficial technical effects:

The disclosure screens a group of anti-BCMA single domain antibodies. Compared with the existing antibodies, respective anti-BCMA single domain antibodies in the group have high activity and strong neutralization or binding capability. The group of single domain antibodies can specifically bind to human BCMA antigens or tumor cell strains expressing BCMA on the cell surfaces, effectively block the binding of BAFF antigen to BCMA, and generate a corresponding signal cascade effect. The group of single domain antibodies can be used for detecting and/or treating a plurality of diseases associated with abnormal BCMA expression.

Hereinafter the present disclosure will be described in details by reference to the accompanying drawings and examples, but the scope of the present disclosure is not limited thereto.

DETAILED DESCRIPTION OF THE EMBODIMENTS

Figure 1:
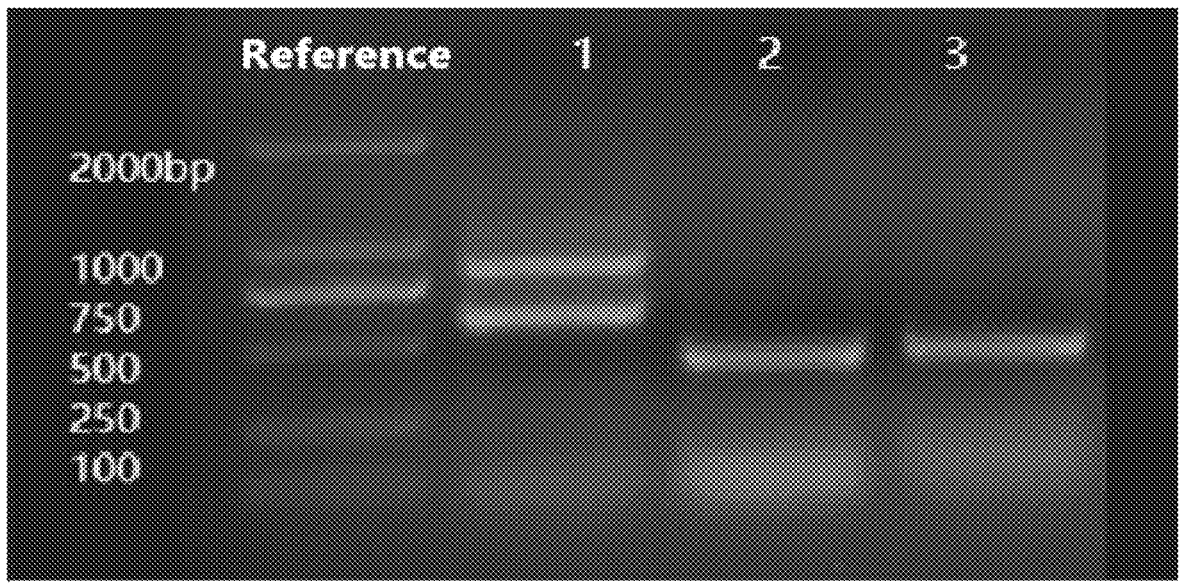
FIG. 1 shows an amplification of common heavy chain antibody and genes of single chain antibodies via a first-round PCR. With reference to (Marker) (1500 BP, 1000 BP, 800 BP, 500 BP, 250 BP and 100 BP)$_1$ PCR amplification products, there are common heavy chain gene amplification fragments having more than 800 BP and heavy chain antibody gene amplification fragments having less than 800 BP, 2 and 3 are PCR amplification products, which are heavy chain antibody gene amplification fragments having only about 500 BP.

The disclosure screens a group of anti-BCMA single domain antibodies by a group of steps, which have potentials of high activity and high neutralization or binding capability. These single domain antibodies have similar structures (composed of a framework region and a complementarity determining region), and similar functional effects. Thus, they can be considered as a group of anti-BCMA single domain antibodies having common structure and common property effects.

The term "BCMA", as used herein, is a member of tumor necrosis factor receptor (TNFR) superfamily, which can bind to a B cell-activating factor or a B lymphocyte stimulator and a proliferation inducing ligand (APRIL)). Multiple myeloma (MM) is a malignant tumor characterized by massive proliferation of clonal plasmocytes. The RNA of BCMA is generally detected in MM cells, and the BCMA protein can be detected on the surfaces of plasmocytes in a patient with multiple myeloma.

The term "multiple myeloma (MM)" as used herein is a malignant tumor characterized by massive proliferation of clonal plasmocytes. At present. MM treatment can induce remission, but almost all the patients will eventually relapse and die. Some monoclonal antibodies have shown a promise to treat MM in pre-clinical studies and early clinical trials, but have not been universally approved. Clearly, there is an urgent need of new antibodies and new immunological therapy for MM.

New antibodies against BCMA are the development object, and finally the protective object of the present disclosure. The scope of the present disclosure encompasses the obtained anti-BCMA antibodies and various forms thereof (for example, single domain antibodies), as well as substances including the antibody as component (for example, pharmaceutical compositions, kits, vectors, chimeric antigen receptors, a chimeric antigen receptor modified T cells, or the like), uses (for example, uses for diagnosis, treatment or application, etc.). However, it should be understood by those skilled in the art that the protective objects of the present disclosure are not limited to these exemplified contents.

The term "single domain antibody (sdAb)" as used herein refers to a fragment containing a single variable domain in an antibody, and is also known as nanobody. Like a complete antibody, it can selectively bind to a specific antigen. Compared with the mass of the complete antibody (150-160 kDa), the single domain antibody (only about 12-15 kDa) is much smaller. The first single domain antibody was made from alpaca heavy chain antibodies by artificial engineering, and known as "VHH segment". In a preferred embodiment, the present disclosure uses the single domain antibody of the alpaca, whereas those skilled in the art should understand that the present disclosure can also encompass single domain antibodies derived from other species. Without limitation, the single domain antibody of the present disclosure is an anti-BCMA single domain antibody.

The term "framework region" is also known as skeleton region. The sequences of about 110 amino acids near the N-terminals of the H chain and the L chain of immunoglobulin vary greatly, while the amino acid sequences in other positions are relatively constant. Accordingly, the light chain and the heavy chain can be divided to a variable region 00 and a constant region (C). The variable region contains an HVR (hypervariable region), also known as complementarity-determining region (CDR) and a frame region (FR). The variability of FR is less than that of CDR. There are four FR molecules in total, that is. FR1, FR2, FR3 and FR4, respectively. During the recognition of antibody, four FR molecules crimp so that CDR molecules are close to each other. It should be understood that the present disclosure is not limited to specific framework region(s), and those skilled in the art can select or obtain appropriate framework region(s) according to practical requirements without departing from the protective scope of the present disclosure.

The term "complementarity determining region (CDR)", the whole antibody molecule can be divided into a constant region and a variable region. In the variable region, some amino acid residues are highly variable, and the regions in which the compositions and arrangement orders of these amino acid residues are more prone to vary are called hypervariable regions. There are three hyper-variable regions (HVR) in the V regions of the L chain and the H chain, which can form a precise complementation with the antigen determinants in terms of spatial structure, and thus the hyper-variable regions are also called complementarity determining regions.

The term "identity" of sequence as used herein is interchangeably used with "homology", and refers to a similarity degree between sequences as measured by sequence alignment softwares, such as BLAST. The sequence alignment methods and softwares are well-known by those skilled in the art. Modified nucleotide sequences can be obtained by substitution, deletion and/or addition of one or more (for example, 1, 2, 3, 4, 5, 6, 7, 8, 9, 10, 11, 12, 13, 14, 15, 16, 17, 18 or more) amino acids or bases in a known sequence. For example, by modifying the amino acid sequence or nucleotide sequence as set forth in one or more of sequence SEQ ID NOs: 1-198 of the present disclosure via conventional means (for example, by conservative substitution), it is feasible to obtain sequences having more than 80%, more than 85%, more than 90%, more than 95% or more than 99% sequence identity to these sequences, and having substantially the same properties, which are encompassed within the protective scope of the present disclosure. Preferably, the present disclosure obtains sequence identity by conservative substitution, but is not limited thereto.

The term "amino acid sequence" refers to an arrangement in which amino acids are linked to each other to form a peptide chain (or polypeptide), wherein the amino acid sequence can only be read in one direction. There are more than 100 types of different amino acids, twenty of which are commonly used. The present disclosure does not exclude the case that other substances (e.g., saccharides, lipids, and other modifications) are attached to the amino acid chains, and is not limited to the 20 amino acids that are commonly used, either.

The term "nucleotide sequence" refers to an arrangement of bases in DNAs or RNAs, namely, an arrangement of A, T, G and C in DNA, or an arrangement of A, U, G and C in mRNA. It also includes arrangements of bases in rRNA, tRNA and mRNA. It should be understood that the antibody gene of the present disclosure also encompasses, in addition to DNA sequences, RNA (rRNA, tRNA and mRNA) and their complementarity sequences. It will also be understood that genes encoding the antibodies of the present disclosure are not equivalent to the sequences as set forth in SEQ ID NOs: 133-198 of the present disclosure, and the genes which encode the antibodies of the present disclosure but are different from the nucleotide sequences as set forth in SEQ ID NOs: 133-198 are also within the protective scope of the present disclosure.

In some embodiments, the polypeptide, the pharmaceutical composition, the chimeric antibody receptor or the CART of the present disclosure comprises one single domain antibody, it should be understood that the present disclosure is not limited thereto. The above substances of the present disclosure can contain two, three, or multiple single domain antibodies, wherein the multiple single domain antibodies are the same or different. Moreover, in addition to the single domain antibodies of the present disclosure, other antibodies or single domain antibodies that are not contained in the present disclosure can also be included without going beyond the scope of the present disclosure.

The term "expression vectors" refers to a vector that incorporates expression elements (such as, promoter, RBS, or terminor) on the basis of the basic backbone of a cloning vector so that a target gene can be expressed. The expression vector comprises four parts: a target gene, a promoter, a terminator and a marker gene. The present disclosure includes, but is not limited to, a prokaryotic cell expression vector, a eukaryotic cell expression vector or other cell expression vectors.

"Chimeric antigen receptor (CAR)" is a core component of "chimeric antigen receptor T cell (CART)", which imparts a T cell with an ability to recognize tumor antigens in an independent manner, so that the T cell modified by CAR is capable of recognizing a broader range of targets as compared with a natural T cell surface receptor. The basic design of CAR comprises a tumor-associated antigen binding region, an extracellular hinge region, a transmembrane region, and an intracellular signal region.

In an embodiment of the present disclosure, the chimeric antigen receptor or chimeric antigen receptor T cell of the present disclosure can contain one, two or more single domain antibodies of the present disclosure, which can be the same or different.

In an embodiment of the present disclosure, the "pharmaceutical composition" of the present disclosure can contain one, two or more single domain antibodies of the present disclosure, which can be the same or different.

The term "humanized" antibody refers to an antibody in which the constant regions (namely CH and CL regions) of the antibodies or the whole antibodies are encoded by human antibody genes. The humanized antibody can greatly reduce the immune side reaction of a heterologous antibody in a human organism. The humanized antibody includes several types including chimeric antibodies, modified antibodies and full human antibodies. It will be appreciated that those skilled in the art can prepare suitable humanized forms of the single domain antibodies of the present disclosure according to the practical requirements, which are within the scope of the present disclosure.

The term "lentivirus" as used herein is one genus of Retroviridae including eight viruses that can infect humans and vertebrates, wherein the primary infection cells are mainly lymphocytes and macrophages, and the infected individuals will eventually develop the diseases. The types of lentiviruses include, for example, human immunodeficiency virus (HIV), simian immunodeficiency virus (SIV), equine infectious anemia (EIA), and feline immunodeficiency virus (FIV). The progress of lentiviral vector research is rapid and intensive. This vector can effectively integrate foreign genes into host chromosomes, so as to achieve persistent expression. In terms of infectability, it can effectively infect neurons, hepatocytes, cardiomyocytes, tumor cells, endothelial cells, stem cells and other types of cells, so as to achieve good gene therapeutic effect. In addition, those skilled in the art can also select other suitable vectors other than lentivirus, which are within the protective scope of the present disclosure.

Hereinafter the present disclosure will be described in details by reference to the following examples. However, the present disclosure is not limited to the specific details of these examples, because for persons skilled in the art, other variations are well established, or obvious according to the direct disclosure and the appended claims. Therefore, all the technologies achieved based on the above description of the present disclosure shall fall within the scope of the present disclosure.

Unless otherwise specified, all the experimental methods described in the following examples are conventional methods; and all the reagents and biomaterials are commercially available, unless otherwise specified.

Example 1: Construction of Anti-BCMA Antigen-Specific Single Domain Antibody Library 1) Immunization of Alpaca with BCMA Antigen It is performed according to the conventional immunization method. Briefly, adult healthy alpacas were subject to multipoint subcutaneous injections at their necks and backs with BCMA antigen (Human TNFRSF17/BCMA/CD269 Protein, purchased from Beijing Yiqiao Shenzhou. Product No. 10620-H15H) with a total weight of about 2 mg, in which the antigen and an equal volume of Freund's adjuvant were added. Immunizations were carried out for 4-6 times. The absorption of mass at the injection sites was followed to confirm correct immunization. The immunization interval time was 7-15 days. After the fourth immunization, serum was collected to determine the immune titer of the antigen. When the titer reached 10,000 times or more (ELISA method), about 100 ml of whole blood was collected, and lymphocytes were separated and stored at −80° C., for subsequent use.

2) Separation and RNA Extraction of Peripheral Blood Lymphocytes of Alpaca

Peripheral blood lymphocytes of alpacas were separated by using a QIAGEN kit (QIAamp RNA Blood Mini Kit (50), Product No. 52304) following the instructions. Briefly, to 1 ml of full blood was added 5-10 ml of red blood cell lysate. The mixture was uniformly mixed, and placed in an ice bath for 30 min. It was centrifuged for 10 min at 2000 rpm after red blood cells were lysed. The supernatant was discarded, and an additional 1-2 ml of red blood cell lysate was added and uniformly mixed. The mixture was placed in an ice bath for 10 min to lyse residual red blood cells, and then centrifuged at 2000 rpm for 10 min. The supernatant was discarded, and 0.3 ml of lysate was added to mix with leukocytes uniformly. The resultant mixture was stored at −80° C., for subsequent use.

RNA purification was carried out by using a QIAGEN kit (QIAamp RNA Blood Mini Kit (50), Product No. 52304) following the instructions. Briefly, to 0.3 ml of the separated alpaca lymphocytes was added 0.3 ml of buffer RLT, and the mixture was mixed well with shaking. The mixed liquid from the last step was transferred to a collection tube equipped with an adsorption column (QIAshredderSpinColumn), and centrifuged at 14,000 rpm for 2 min. The filtrate in the collection tube was transferred to a new centrifuge tube. 0.5 ml of 70% ethanol was added into the filtrate, and uniformly mixed upside down. The mixture was centrifuged at 10000 rmp for 15 s, the waste liquid in the collection tube was discarded, and the adsorption column was re-placed into the collection tube. The adsorption column was transferred to a new 2 ml collection tube, 0.7 ml of buffer RWI was added, and the mixture was centrifuged at 10000 rmp for 15 s. The adsorption column was transferred to a new 2 ml collection tube. 0.5 ml of buffer RPE was added, and the mixture was centrifuged for 15 s at 10000 rmp. 0.5 ml of buffer RPE was added, and the mixture was centrifuged at 14000 rmp for 3 min. The adsorption column was transferred to a new 1.5 ml centrifuge tube, and 30-50 µl RNase-free water was added dropwise into the middle of an adsorption membrane in the air. The mixture was placed at room temperature for 2-5 min, and centrifuged at 12,000 rpm for 1 min. The plasmid solution was collected into the centrifuge tube, and measured for the RNA concentration.

3) Variable Region-VHH of Heavy Chain Antibody

Figure 2:
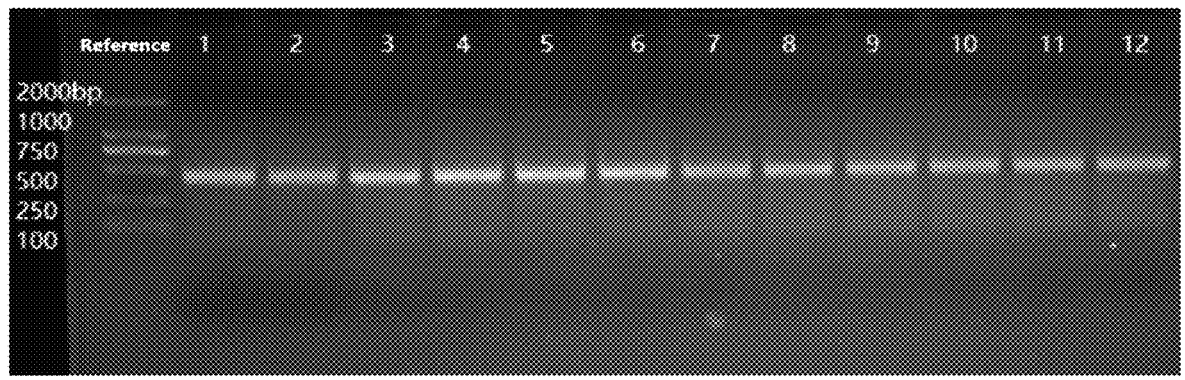
FIG. 2 shows a VHH target gene fragment obtained in second-round PCR amplification. Marker (1500BP, 1200 BP, 1000 BP, 800 BP, 700 BP, 600 BP, 500 BP, 250 BP and 100 BP). 1-12 are PCR amplification products, which are heavy chain antibody VHH gene amplification fragments having about 500 BP.

Synthesis of a first chain of cDNA: A cDNA synthesis kit (MiniBESTAgarose Gel DNA Extraction Kit ver.4.0, TAKARA Company) was used following the instructions. With this template, two sets of primers were used to perform PCR amplification of the VHH gene fragment of the heavy chain antibody. By using a Nested PCR method, the fragments of greater than 800 bp in the first PCR amplification are common heavy chain gene fragments, and the fragments between 800 bp and 500 bp are heavy chain antibody gene fragments with deletion of light chains (see FIG. 1). The gene fragments of heavy chain antibodies with deletion of light chain were recovered by gel cutting, and used as the template to obtain the VHH target gene (~500 bp) by PCR amplification with VHH specific primers (see FIG. 2).

```
Synthesis of primers:
First-round PCR Fd5' primer:
YF-1:
                                      (SEQ ID NO: 199)
CGC CAT CAA GGT ACC AGT TGA YF-2:
                                      (SEQ ID NO: 200)
GGG GTA CCT GTC ATC CAC GGA CCA GCT GA First-round PCR Bd3' primer:
YBN:
                                      (SEQ ID NO: 201)
CAG CCG GCC ATG GCC SMK GTR CAG CTG GTG GAK TCT GGG

GGA G

Second-round PCR primer:
YV-BACK:
                                      (SEQ ID NO: 202)
CAT GTG CATGGCCTA GAC TCG CGG CCCAGC CGG CCA TGG

CC

YV-FOR:
                                      (SEQ ID NO: 203)
CAT GTG TAG ATT CCT GGC CGG CCT GGC CTG AGG AGA CGG

TGA CCT GG
```

4) Ligation of VHH Fragment and Phage Display Vector and Electric Transformation of TG1 Competent Cells After the VHH fragment and the pHEN6 vector plasmid were subjected to single digestion with Sfl, the VHH fragment and the pHEN6 vector (Conrath, KEM other. Antimicrob Agents Chemother (Antimicrobial Chemotherapy) 2001, 45: (10) 2807-12, Chinese patent ZL20111028003.1)) were ligated by a ligase, and then electrically transformed into TG1 competent cells, which were used to coat a plate, and detected by colony PCR for verification of the antibody insertion rate. Detection of recombinant gene cloning efficiency: an LB/Amp plate was coated with an electrically transformed bacterial solution, cultured overnight at 32° C., and detected by colony PCR for verification of the ligation efficiency of the antibodies on the next day. The ligation efficiency of the phage-antibody library was more than 90%. The LB/Amp plate was coated with the electrically transformed bacterial solution, and cultured overnight at 32° C. The culture was washed with 2YT culture medium, and 15% glycerol was added. The mixture was stored at −80° C.

5) Preparation of VHH Phage Antibody Library

Helper phage M13K07 (Invitrogen) was added into the antibody library for rescue: the phage antibody library was prepared according to a conventional method and stored at −80° C., for subsequent use.

Example 2: Preparation of Single Domain Antibody of BCMA

Screening of BCMA-Specific Single Domain Antibody
 First-round: BCMA protein concentration 150 μg/ml, 150 μl/well, 1 micropore, incubate overnight at 4° C.
 Second-round: BCMA protein concentration 10-100 μg/ml, 150 μl/well, 5 micropores, incubate overnight at 4° C.
 Third-round: BCMA protein concentration 10-50 μg/ml, 150 μl/well, 5 micropores, incubate overnight at 4° C.

| Blocking: 1% CPBS, 300 μl/well, 37° C., incubate for 2 h. | | | | |
|---|---|---|---|---|
| Screening Round No. | Total amount of added phage antibody library | Elution solution + Tris-HCl | Number of single colony | Elution titer |
| First round | $5.6 \times 10^{11}$ | 300 μl + 200 μl | 10 | 50/μl |
| Second round | $5.25 \times 10^{11}$ | 150 μl/well × 5 + 350 μl | ¼ = 600 about 2400 | $2.4 \times 10^4$/μl |
| Third round | $5.32 \times 10^{11}$ | 150 μl/well × 5 + 350 μl | ¼ = 750 about 3000 | $3 \times 10^4$/μl |

2. Picking of Positive Clones Via Phage ELISA

A single colony was randomly picked from an agar plate screened for grown colonies in the third round, inoculated and cultured in a 96-well culture plate containing an Amp 2YT liquid culture medium, and subject to superinfection of helper phages to induce the expression of the phage antibody. The expression supernatant was harvested, and then an ELISA assay was carried out with BCMA as an antigen. BCMA-positive wells were selected, and subject to DNA sequencing to identify the gene sequence of the anti-BCMA single domain antibody clones. A series of single domain antibody gene sequences including those in Annex 3 were obtained and used for further expression and screening of the single domain antibodies with high specificity and high activity.

Example 3: Construction of Expression Plasmid of Specific BCMA Single Domain Antibody The specific BCMA single domain antibody gene obtained in Example 3 was amplified by PCR to obtain PCR products with restriction enzymes BbsI and BamHI sites. The PCR products and vectors (pSJF2 vector) (kim ls. Biosic Biochem. 2002, 66 (5): 1148-51, Chinese patent ZL 201110280031) were treated with restriction enzymes BbsI and BamHI respectively, and recombined by ligation with T4 ligase to obtain the plasmid sdAb-pSJF2 that can be efficiently expressed in *Escherichia coli*, which was subject to gene sequencing to determine the correctness of its sequence.

1) PCR amplification conditions required for obtaining VHH target genes, and compositions of 50 μl PCR system:

| | |
|---|---|
| MIX | 25 μl |
| Positive colony clone | 1 μl |
| 5' primer | 1 μl (1 mol/l) |
| 3' primer | 1 μl (1 mol/l) |
| DEPC-treated ddH$_2$O | 22 μl |
| Total volume | 50 μl |

| PCR Reaction Conditions: | | | |
|---|---|---|---|
| 94° C. | 3 min | 30 s | |
| 94° C. | 30 s | | |
| 72° C. | 55° C. 1 min | | 30 rounds |

(SEQ ID NO: 204)
5' primer-GAA GAAGAA GAC AA CAG GCC SVK GTG MAG CTG GWG GAK TCT (SEQ ID NO: 205)
3' primer-gaagatctccggatccTGAGGAGACGGTGACCTGGGT 2) The target gene and the vector were digested, ligated, and transformed into TG1 cells. The products were subject to PCR for identifying the clones containing the target fragment, which were subject to gene sequencing so as to obtain the BCMA single domain antibody expression plasmid with a correct gene sequence.

Example 4: Expression and Purification of Anti-BCMA Single Domain Antibody

Figure 3:
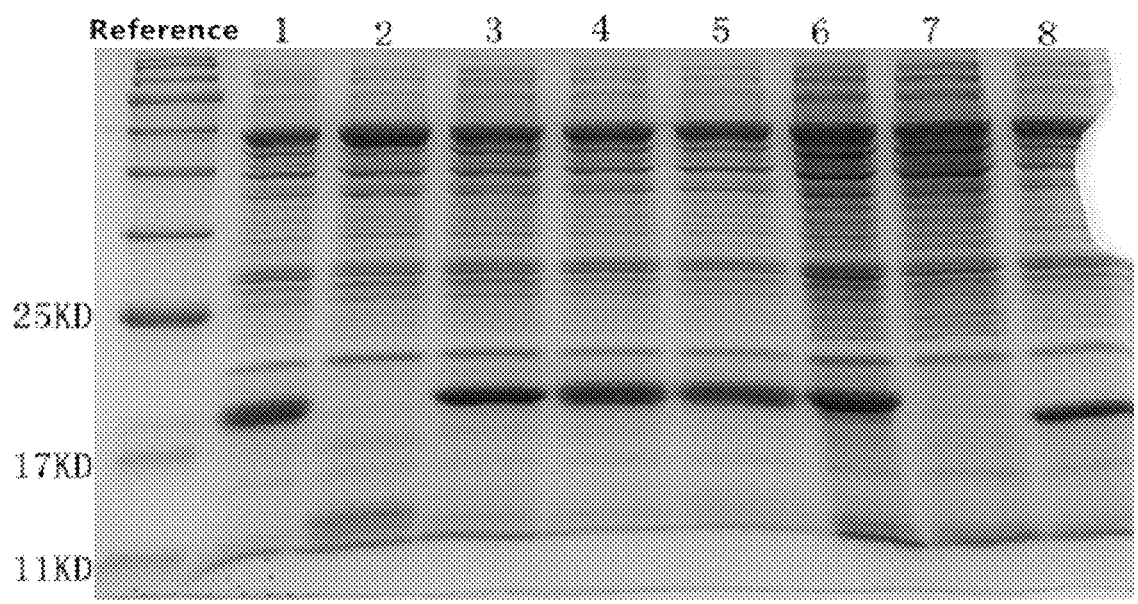
FIG. 3 is an SDS-PAGE illustration of expressed BCMA-sdAbs before purification.
Figure 4:
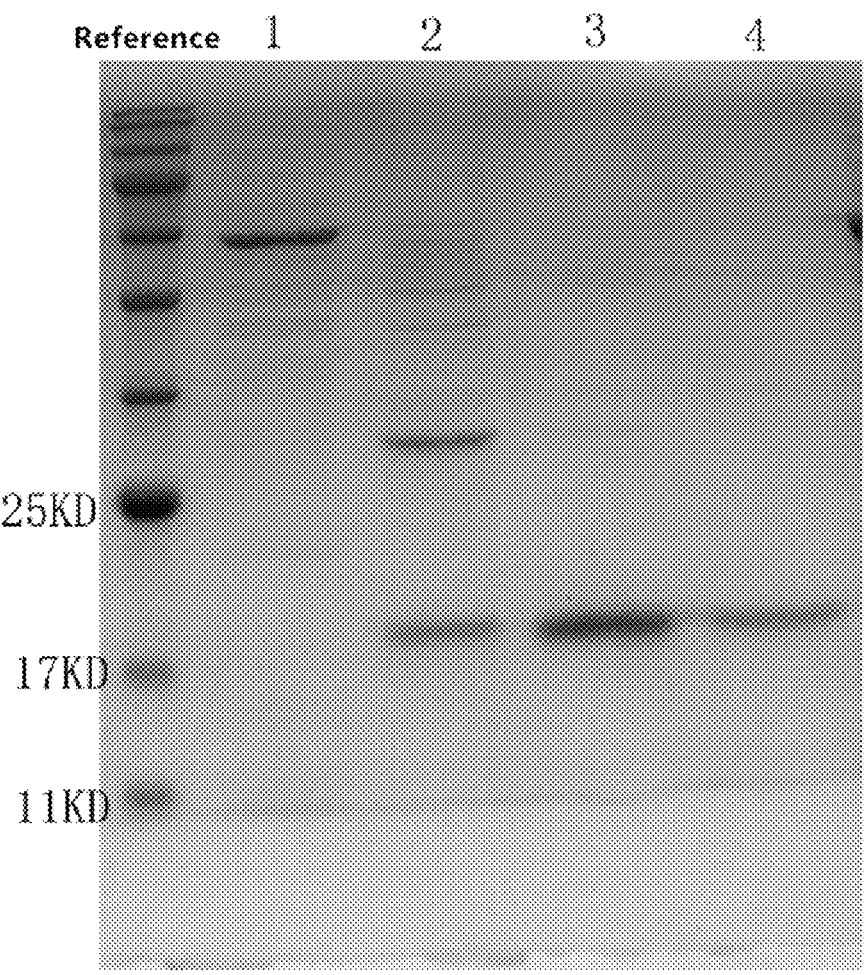
FIG. 4 shows an SDS-PAGE illustration of expressed BCMA-sdAbs after being purified by a nickel column.

The strains containing the plasmid BCMAsdAb-pSJF2 in example 3 were inoculated on an LB culture plate containing ampicillin at 37° C., overnight. A single colony was picked and inoculated in 15 ml LB medium solution containing ampicillin, and was cultured in a shaker at 37° C., overnight. 10 ml of culture was transferred to 1 L of 2YT culture solution containing ampicillin and cultured in a shaker at 37° C., at 240 rpm/min. After OD value reached 0.4-0.6, 0.5-1.0 mM IPTG was added and additionally incubated overnight. The above solution was centrifuged for collecting bacteria. The bacteria were lysed by adding lysozym and centrifuged, and the soluble single domain antibody protein in the supernatant was collected. A protein with the purity of more than 95% was obtained by Ni ion affinity chromatography. FIG. 3 shows the expressed anti-BCMA single domain antibody protein, and FIG. 4 shows SDS-PAGE electrophoresis results of expressed BCMA-sdAbs purified by a nickel column.

Example 5: Affinity Assay Test of BCMA Single Domain Antibody

1) Preparation of Sample
Antigen: Bio-BCMA was diluted to 10 μg/ml with 1× dynamic buffer (1×PBS, containing 0.05% Tween 20, 0.1% BSA, pH7.2):
Single domain antibody was gradually diluted into 400 nM, 200 nM, 100 nM, 50 nM, 25 nM, 12.5 nM and 6.25 nM with 1× kinetic buffer:
2) Sample Test
The antigen to be tested was loaded through an SA sensor. The antigen was diluted by 5 gradients, and all the BCMA single domain antibodies had an affinity of 50 nm, 20 nm, 10 nm, 1 nm, 0.1 nm and 0.01 nm.

Example 6: Binding Test of Purified BCMA Single Domain Antibody and BCMA Antigen (ELISA)

Figure 5:
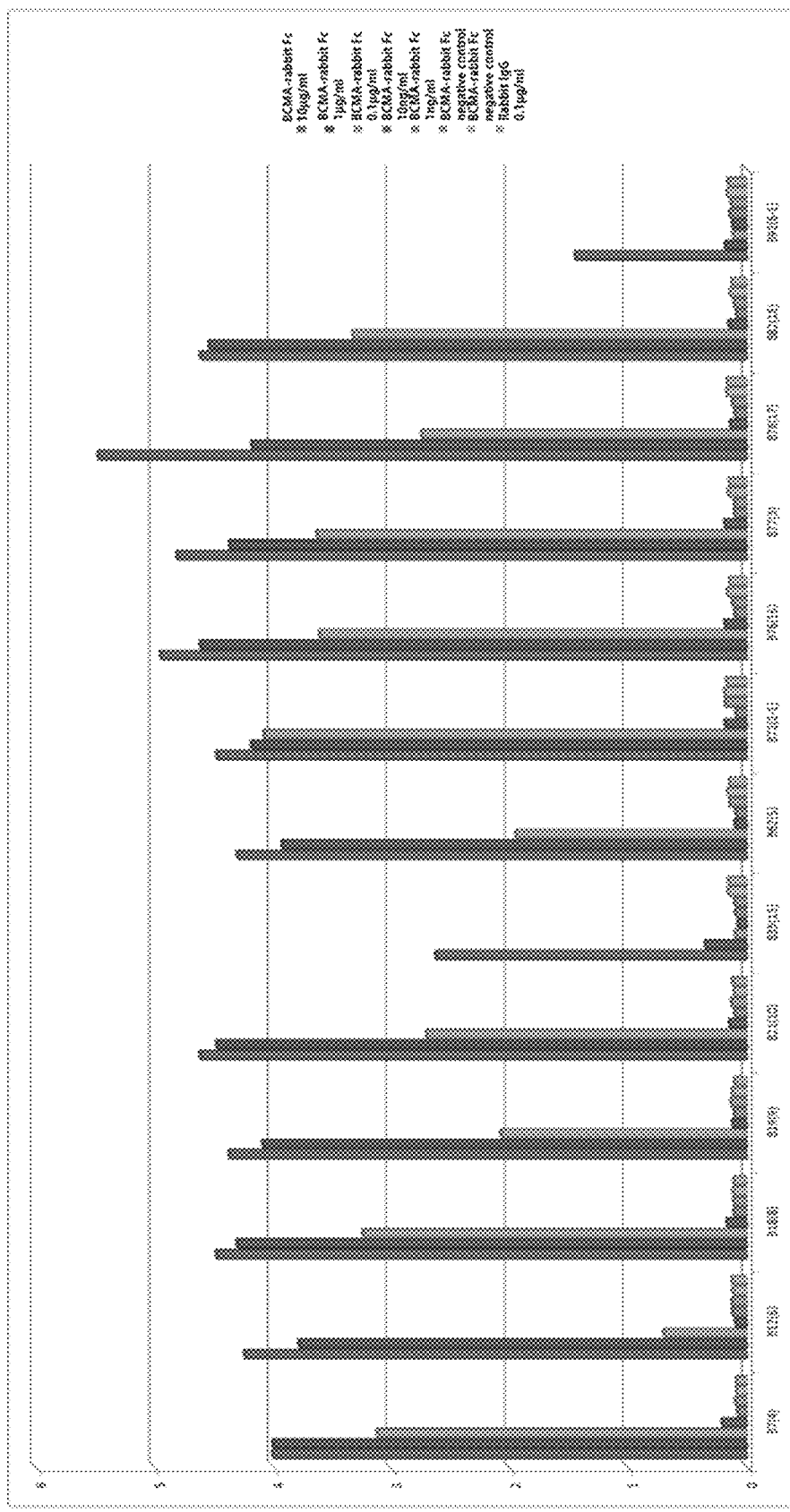
FIG. 5 shows a concentration gradient of a purified BCMA single domain antibody binding to BCMA protein (ELISA).

The BCMA-Fc antigen was diluted to 1 μg/ml with 0.05 M $NaHCO_3$ (pH 9.5). A 96-well place was coated with 100 μl antigen overnight at 4° C. The 96-well plate was blocked with 300 μl 0.5% BSA-PBS for 2 h at 37° C. The purified BCMA single domain antibodies with different dilution concentrations were added in 100 μl/well at 37° C., for 1 h. The plate was washed three times with 0.05% PBST. Mouse anti-His-HRP diluted in 1:5000 fold was added in 100 μl/well at 37° C., for 1 hour. The plate was washed three times with 0.05% PBST. 100 μl of TMB was added and kept in dark place at room temperature for 20 min. 100 μl of 1 mol/L HCl was added to quench the reaction. The OD value of the sample at 450 nm was measured by a microplate reader. FIG. 5 shows the concentration gradient of purified BCMA single domain antibody binding to BCMA protein (ELISA). Except that the binding ability of the two antibodies of B35 (13) and B92 (6-1) to the BCMA antigen was relatively low: the binding ability of the rest 11 antibodies to BCMA antigen was very high.

Figure 6:
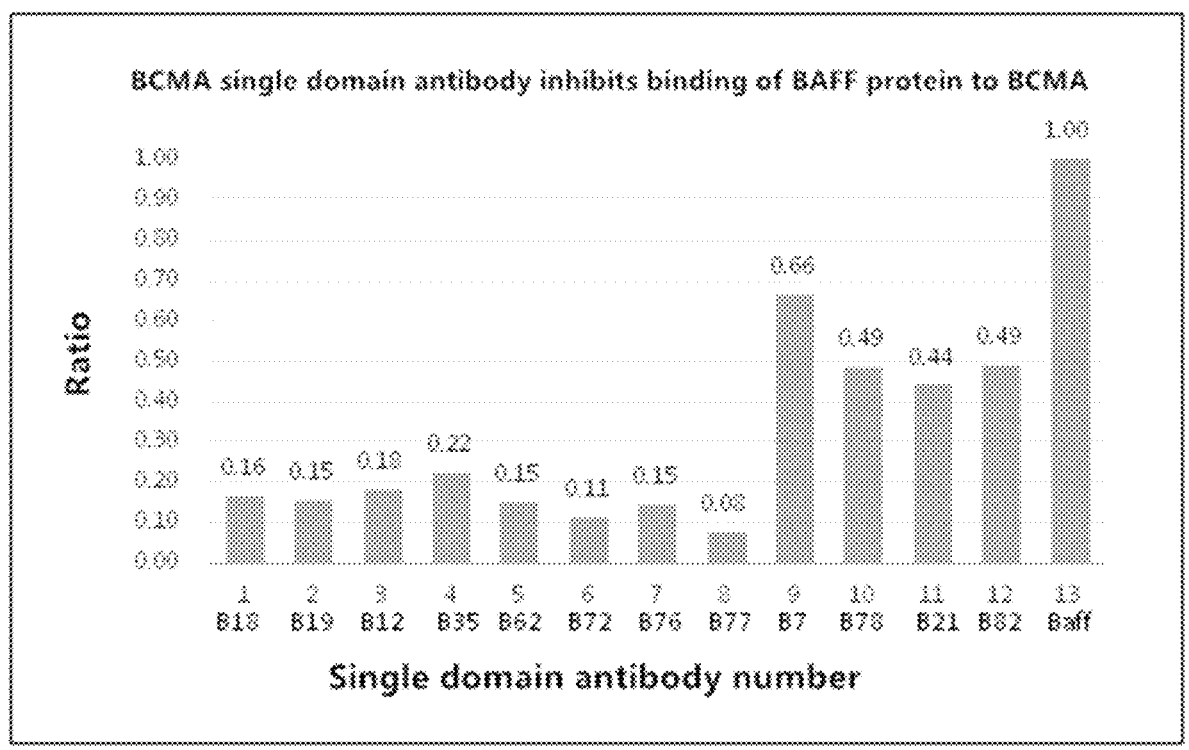
FIG. 6 shows that a BCMA single domain antibody can competitively inhibit the binding of BAFF protein to BCMA protein.

Example 7: Binding Competitive Inhibition Test of BCMA Single Domain Antibody on BAFF and BCMA Because BCMA can bind to BAFF, the functional BCMA single domain antibody should be able to competitively inhibit the binding of BAFF to BCMA. BAFF protein coated a detachable ELISA plate according to 1 μg/ml. 100 μl/well and incubated overnight at 4° C. 2% BSA was added for blocking. 300 μl/well, incubated at 37° C., for 2 hours. The BCMA single domain antibody was diluted to a final concentration of 10 μg/ml. 100 μl BCMA (10 μg/ml) single domain antibody was added. 2 μl of BAFF (5 μg/ml) protein was added in each well to be uniformly mixed. Goat anti-rabbit IgG HRP (1:5000) was diluted. 100 μl/well, incubated for 1 h at 37° C. TMB chromogenic solution was added. 100 μl/well, and reacted in dark for 10 min. The reaction was quenched by adding 2M $H_2SO_4$ at 50 μl/well. The OD value was measured at 450 nm. FIG. 6 shows that the BCMA single domain antibody can competitively inhibit the binding of BAFF protein to BCMA protein. Different BCMA single domain antibodies could competitively inhibit the binding of BAFF protein to BCMA protein, and the inhibition rate ranged from 34% to 92%.

Figure 7:
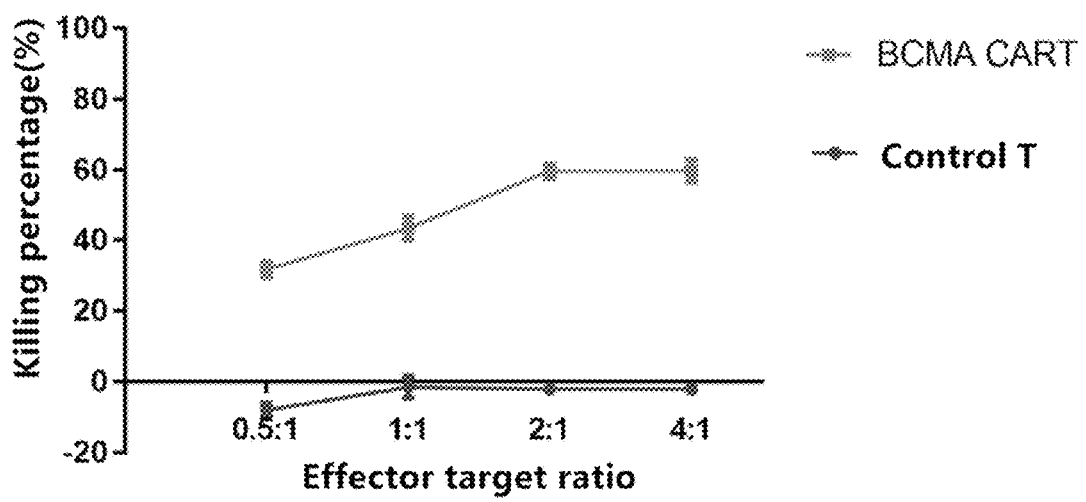
FIG. 7 shows a killing efficiency of BCMA CART on tumor cells.

Example 8: The Study on BCMA Single Domain Antibody as Recognition Antibody Targeting Specific BCMA Antigen on CART Cell 1) Construction of Vector
A BCMA single domain antibody gene and a second-generation CAR structure gene were synthesized. The two genes were spliced by overlapping PCR to obtain a BCMA CAR gene. After the synthetic gene was obtained, molecular cloning was carried out. First. PCR products of two gene fragments were obtained. Then, overlapping PCR was carried out to obtain BCMA CAR gene with the second-generation CAR structure in which two fragments are linked. Through enzyme digestion of Pre vector and BCMA CAR gene, ligation, transformation, cloning, plasmid upgrading and sequencing, the BCMA CAR-expressed lentiviral vector Pre-Lenti-EFI BCMA with a correct sequence was obtained.
2) Packaging of Lentivirus
On the day before virus packaging. 293T cells were digested by trypsin and spread in 150 cm culture dish. The cells were incubated in 5% $CO_2$ culture box for 8-24 h. When the adherent cells reached 80% of the total culture dish area, the 293T cells were transfected. Pre-Lenti-EFI BCMA CAR: psPAX2: pMD2G=4:3:1 was co-transfected with lipofectamine 2000. The virus supernatant was collected after 48 hours, and centrifuged at 4° C., at 1250 rpm for 5 min to remove the dead 293T cells and cell debris. Then, the virus supernatant was filtered, concentrated, sub-packaged, and stored in a refrigerator at −80° C.
3) Preparation of CART Cells
10 ml of fresh blood was taken from healthy volunteers. Peripheral blood mononuclear cells (PBMC) were isolated with lymphocyte isolation solution, and then T cells were isolated and purified by magnetic beads. $2×10^6$ T cells/well were seeded into a 6-well plate, cultured in an x-vivo 15 culture medium containing IL-2 (1000 U/ml) and stimulated with anti-CD3 for 24 h. After 24 hours of stimulation, a BCMA virus solution was added and infected overnight. 2 ml of culture medium was added on the second day. After 6-7 days of infection, the expression of CAR was evaluated by flow cytometry. The positive rate of expressing anti-BCMA-CAR by transfected T cells was analyzed using biotinylated BCMA via flow cytometry.
4) Determination of Killing Vitality
In a cell killing test, an LDH detection kit (Promega) was used for detection. CART cells/T cells: target cells were set with four gradients, which were 0.5:1, 1:1, 2:1 and 4:1, respectively. Daudi cells 3×10⁴/well, and the rest wells were supplemented to 200 μL with an X-VIVO-containing culture medium/1640) culture medium. The 96-well plate was cultured in a 5% CO2 incubator at 37° C. After 17 h, 20 μl of lysate was added into the maximum release well, and the cells were uniformly mixed to be completely ruptured. The 96-well plate was incubated in the CO2 incubator for 2 h. Two hours later, the maximum release well was observed. After target cells were completely lysed. 50 μL of supernatant was sucked from each well to the 96-well plate with a flat bottom, and then 50 μL of substrate solution was added to each well, development was carried out for 30 min in the dark. After 30 min, the mixture was observed for the color change, wherein the colors of the maximum release MM. IS well and the CART cell well should be darker. A microplate reader was used for measurement at a wavelength of 490 nm. The killing results were seen in FIG. 7. BCMA chimeric antigen receptor modified T cells can specifically kill BCMA-positive cells with a very high killing activity of more than 20%, and has no killing effect on BCMA-negative cells.

Annex 1:

| Sequence | CDR1 | CDR2 | CDR3 | Clone group |
|---|---|---|---|---|
| 1 | TYFMA | GGIRWSDGVPHYADSVKG | CASRGIADGSDFGS | G3 |
| 2 | IKAMA | AYIRSGGTTNYADSVKG | CNADYSPPGSRFPDLGP | G1 |
| 3 | ANTM | ARISTDGRTNYADSVKG | CNANWLSKFDY | NG7 |
| 4 | VNAVA | AYIRRSGSTNYADSVKG | CNADFGSDYVVLGS | G5 |
| 5 | IKALA | AYITSGGNTNYADSVRG | CNADFGEGTIISLGP | G9 |
| 6 | INAMA | AALTSGGNTHYADSVKG | CNADFGTAGLVVLGP | G7 |
| 7 | INAMA | AYIRSNGRTNYADSVKG | CNADYGPPVSIGP | G6-2 |
| 8 | IKAMA | AAVTSGGSTHYLDSVKG | CNADFGTDYVDLGP | G10 |
| 9 | INAMG | AAITKSNNINYADSVKG- | CNGFFALPGYSSEEFGP | G2 |
| 10 | MNRMG | ADIRDGGSTIYSDSVKG | CNAGRTGDRFNLVAY | G8 |
| 11 | GYAMA | AAISSSSNSAPYYANSVKG | CAARYGTKRYVAREYDS | G17 |
| 12 | INGMG | ARIDSRGSAYYADFVEG | CFAWQGAETY | G25 |
| 13 | TYAMA | AYITNGGSTDYAASVKG | CNGATRGAQLVFD | NG1 |
| 14 | NYAMA | AAISVSANSAPYYANSVKG | CAARYGTKRYVAREYDS | NG20 |
| 15 | LNAMG | ARIAADGSTHYADSVEG | CFAWLGTDTY | NG21 |
| 16 | NNAMG | ARIDSGGITRYADSLKG | CFAHVGGTI | G14 |
| 17 | INSMG | ASITGGGSSRYADSVKG | CNTIPPARTQSDHGEWYDY | NGS1 |
| 18 | IN-MS | ATTRHDSTHYSDSVKG | CSGFFLDGSTWHPY | G12 |
| 19 | INAMA | AYIRSNGSTNYADSVKG | CNGFFTLPGYSSEEFGP | G6 |
| 20 | INAMG | AGITKGGRTNYADSVKG | CNGLCSGRECYGDSLFAA | G22# |
| 21 | INAMA | AYIRSNGRTNYADSVKG | CSGFFLDGSTWHPY | G6-1 |
| 22 | DYAIG | SCISSSDGSTHYADSVKG | CATPWVTYCPENLLFSY | G13# |
| 23 | DYAIG | SCITSSDGSTYYADSVKG | CATPWVTYCPENLLFSY | G13-2# |
| 24 | IKAMG | AAITSGGSTNYADSVKG | CNGFFEYRGLEQLGP | G31 |
| 25 | IRAMT | AVLTSAGKPMYADSVKG | CNADFGTPGSVVLGP | G4 |
| 26 | IEAMG | AAITSGDSTNYADFVKG | CNALMVVRAGSNPEIGP | NG2 |
| 27 | DYAIG | SCISSSDGSTYYADSVKG | CATPWVTYCPENLLFSY | G13-3# |
| 28 | LDAVG | ARIDRRGSTYYAVSVEG | CFAWQGAETH | G20 |
| 29 | FNDMG | AAITSSRNTLYVDSVKG | CNPYPSPNNY | NG3 |
| 30 | INAMG | AAITRSGKTNYADSVKG | CNGFYGSEFGP | NG4 |
| 31 | RYAVG | ASITWSGDYTYYKDSVKG | CAADKSSFRLRGPGLYDY | NG5 |

Annex 1:

| Sequence | CDR1 | CDR2 | CDR3 | Clone group |
|---|---|---|---|---|
| 32 | YYAIG | SCISSRDGTTHYADSVKG | CATPWVTYCPENLLFSY | ++ |
| 33 | YYAIG | SAISNIDDDTYYEDSVKG | CAADKDVVVRTGLSESDY | NG8 |
| 34 | INAMA | AVITSGGRTMYAESVKG | CNGDWGSEGRVLGP | NG9 |
| 35 | IGDME | ASISAGPEMRSAGTPTYAKSVEG | CNADVLTYYNGRYSRDVY | NG10 |
| 36 | INMS | ATITRHDSTHYSDSVKG | CSGFFLDGSTWRPY | G12-1 |
| 37 | GYAVA | AAISSSDNSSPYYANVVKG | CAARYGTKRYVAREYDS | |
| 38 | INAMA | AYIRSSGTTMYADSVKG | CNGDYSPPGSTYPDLGP | NG11 |
| 39 | DYAIG/ YCPENLLFSY | SCITSSDGSTYYADSVKG/ AAIRWSDGVPHYTDSVKG | CATPWVN/ CASRGIADGSDFGSY | G15(bi) |
| 40 | ATTMA | ALITSDWHTKYADSVKD | CYARQAFSEPR | G11 |
| 41 | IDAMG | ARLGSNGFTQYDISVEG | CFAWLGQDTV | NG12 |
| 42 | NYAMG | ASVTRSGDNTYYKDSAKG | CAADKSSFRLRGPGVYDY | NG14 |
| 43 | VMLMG | ASITSADYTTYAESVEG | CKVIAATVWGQETQVRQGLF | NG13 |
| 44 | ARSMT | AVIMGGGSTMYADSVKG | CNADWGEVGFPNLGP | G21 |
| 45 | TYAIG | AAISRRGNKTDYAESVKG | CAASARNFIGTQPLDYDY | NG23 |
| 46 | NYALG | AAIDWRHSSYYADSVKG | CAASSLFPSSAPRQYDY | NG15 |
| 47 | NYAMG | AAIVGSGDSTRYADSVKG | CASSSDPRVYIASTLDY | NG16 |
| 48 | MFIMG | AAISRNSNLTYYFQSVKG | CNADYGPPVSIGP | G23 |
| 49 | IKAMG | AGIVSSGNTNYADFVKG | CNALVVVTSASGPELAS | NG17 |
| 50 | TYFMA | CNADYSPPGSRFPDLGP | AGIVSSGNTNYADFVKG | G1-3 |
| 51 | NYAIA | SSTGSDGNLYTPSVRG | CVAGKRPVITTWIALDA | NG18 |
| 52 | IDSMR | AHITSTGRTNYADAVKG | CNMVTTPYMH | NG24 |
| 53 | ENAMG | AAITSSRSTLYIDSVKG | CNPYPSPNSY | NG25 |
| 54 | ANKMG | ARISTDGRTNYADSVKG | CNANWLDKYDY | NG19 |
| 55 | ARSMT | AVITSGGSTMYADSVKG | CNADWGEVGFVNLGP | NG26 (G21-1) |
| 56 | FNGVA | AVIRSGGNTLYADSVKG | CNVDYSPPGSLVPDLGP | G18 |
| 57 | INAMG | AAITRGGSTNYADSVKG | CNGLCSDDRCYGDSLFAP | G16 |
| 58 | LDAVG | ARIDSRGSAYYADSVEG | CFAYYGAQISFGP | G24 |
| 59 | LDAMG | AHIDDDRGTAYYADFVKG | CFAWQGAETY | G19 |
| 60 | VNAVA | AYIRRSGSTNYADSVKG | CNAGRTGDRFNLVAY | G5-1 |
| 61 | TYFMA | GGIRWSDGVPHYADSVKG | CNADYSPPGSRFPDLGP | G26 |
| 62 | IKAMA | AYIRSGGTNYADSVKG | CASRGIADGSDFGS | G27 |
| 63 | LYAMG | AYIRSGGTTNYADSVKG | CNADYSPPGSRFPDLGP | G1-2 |
| 64 | TYAMG | AAISRRGNKTDYAESVKG | CAASARNFIGTQPLDYDY | G28 |
| 65 | GYFMA | GGIRWSDGVPHYADSK | CASRGIADGSDFGS | G29 |
| 66 | INAMG | AAITKSNNINYADSBKG | CNGFFTLPGYSSEEFGP | G2-1 |

Annex 2

| Sequence | Amino acid sequence | Clone group |
|---|---|---|
| 67 | EVQLQASGGGLAQAGGSLRLSCTASGRTFSTYFMAWFRQPPGKEREYVGGIRWSDGVPHYADS VKGRFTISRDNAKNTVYLQMNSLKSEDTAVYFCASRGIADGSDFGSYGQGTQVTVSS | G3 |
| 68 | QVKLEESGGGLVQPGGSLRLSCAASGSIFSIKAMAWYRQAPGKQRELVAYIRSGGTTNYADSV KGRFTISRDIAKNTVYLQMNSLKPEDTAVYYCNADYSPPGSRFPDLGPWGQGTQVTVSS | G1 |
| 69 | QVKLEESGGGLAQPGGSLRLSCAASGLVFSANTMAWYRRAPGKQRELVARISTDGRTNYADSV KGRFTISRDNREKTVFLQMNRLNPDDTAVYYCNANWLSKFDYWGQGTQVTVSS | NG7 |
| 70 | DVQLQASGGGLVQAGGSLRLSCVASGSIFSVNAVAWYRQAPGKQRELVAYIRRSGSTNYADSV KGRFTISRDNAKNTVYLQMNSLKPEDTAVYYCNADFGSDYVVLGSWGQGTQVTVSS | G5 |
| 71 | QVKLEESGGGLVQAGGSLRLSCAASGSIFSIKALAWYRQAPGKQRELVAYITSGGNTNYADSV RGRFTISRDNAKNTVYLQMNSLKPEDTAVYYCNADFGEGTIISLGPWGQGTQVTVSS | G9 |
| 72 | EVQLVESGGGLVQPGGSLRLSCAASGSEFSINAMAWYRQAPGKQRELVAALTSGGNTHYADSV KGRFTISRDNAKNTWYLQMNSLKPEDTAVYYCNADFGTAGLVVLGPWGQGTQVTVSS | G7 |
| 73 | EVQLQASGGGLVQPGGSLRLSCAASGSIFSINAMAWYRQAPGKQRELVAYIRSNGRTNYADSV KGRFTISRDNAKNTVYLQMNSLKLEDTAVYYCNADYGPPVSIGPWGQGTQVTVSS | G6-2 |
| 74 | EVQLVESGGGLVQAGGSLRLSCVVSGSLLSIKAMAWFRQPPGKRELVAAVTSGGSTHYLDSV KGRFTISRDNANTVHLQMNSLKPEDTAVYYCNADFGTDYVDLGPWGQGTGVTVSS | G10 |
| 75 | DVQLQASGGGLVQPGGSLRLSCAVSGSIFSINAMGWYRQAPGKQRELVAAITKSNNINYADSV KGRFTISTDNAKNTVYLQMNSLKPEDTAVYYCNGFFALPGYSSEEFGPWGQGTQVTVSS | G2 |
| 76 | EVQLVESGGGLVQPGGSLRLSCVASGNIFDMNRMGWYRQPPGKQRELVADIRDGGSTIYSDSV KGRFTISRDNAKNTLYLQMNSLKPDDTAVYYCNAGRTGDRFNLVAYWGQGTQVTVSS | G8 |
| 77 | DVQLQASGGGLVQHGGSLRLSCEASGRTFSGYAMAWFRQAPGKEHEFVAAISSSSNSAPYYAN SVKGRFTISRDNAKMTVYLQMNNLQTEDTAVYYCAARYGTKRYVAREYDSWGQGTQVTVSS | G17 |
| 78 | DVQLQASGGGVVQAGGSLRLSCTASGSIRSINGMGWSRVAPGKQRDFVARIDSRGSAYYADSV EGRFTISRDNAKNTVYLQVDTLKPEDTAVYYCFAWQGAETYWGLGTQVTVSS | G25 |
| 79 | QVKLEESGGGLVQPGGSLRLSCAASGSIGDTYAMAWYRQAPGKQRDLVAYITNGGSTDYAASV KGRFTISRDNAKNTVYLQMNSLKPEDTAVYYCNGATRGAQLVFDWGQGTQVTVSS | NG1 |
| 80 | QVKLEESGGGLVQHGGSLRLSCAASGGTFSNYAMAWFRQAPGKEREFVAAISVSANSAPYYAN SVKGRFTISRDNAKNTVYLQMNSLKTEDTAVYYCAARYGTKRYVAREYDSWGQGTQVTVSS | NG20 |
| 81 | QVKLEESGGGLVQPGGSLRLSCAASGSSVSLNAMGWSRVQPGSTRDFVARIAADGSTHYADSV EGRFTISGDAARNTVYLQMDSLKPEDTAVYYCFAWLGTDTYWGQGTQVTVSS | NG21 |
| 82 | DVQLQASGGGLVQAGGSLTLSCAASGSIGDNNAMGWSRTPPGKQREFVARIDSGGITRYADSL KGRFTVSRDTGKNTVSLQMNSLKAEDTGVYYCFAHVGGTIWGQGTQVTVSS | G14 |
| 83 | QVQLVESGGGLVQPGGSLRLSCLPSGGIFTINSMGWYRQAPGKQRELVASITGGGSSRYADSV KGRFIMSRDNAKNMVYLQMNSLKPEDTAVYYCNTIPPARTQSDHGEWYDYWGQGTQVTVSS | NSG1 |
| 84 | QVKLEESGGGLVQAGGSLRLSCAASSSIFSINMSWYRQAPGNERELVATITRHDSTHYSDSVK GRFTISRDDDKNTIYLQMNSLKPEDTAVYYCSGFFLDGSTWHPYWGQGTQVTVSS | G12 |
| 85 | EVQLVESGGGLVQPGGSLRLSCAASGSIVSINAMAWYRQAPGKQRELVAYIRSNGSTNYADSV KGRFTISRDNAKNTVYLQMNSLKLEDTAVYYCNGFFTLPGYSSEEFGPWGQGTQVTVSS | G6 |
| 86 | EVQLVESGGGLVQPGGSLRLSCAASESIFSINAMGWYRQAPGKQREYVAGITKGGRTNYADSV KGRFTISRDDAKNTVYLQMNSLKPEDTAVYYCNGLCSGRECYGDSLFAAWGQGTQVTVSS | G22# |
| 87 | EVQLVESGGGLVQPGGSLRLSCAASGSIVSINAMAWYRQAPGKQRELVAYIRSNGRTNYADSV KGRFTISRDNAKNTVYLQMNSLKLEDTAVYYCSGFFLDGSTWHPYWGQGTQVTVSS | G6-1 |
| 88 | EVQLVESGGGLAQAGGSLRLSCAASGFTFDDYAIGWFRQAPGKEREGVSCISSSDGSTHYADS VKGRFTISRDNARNTVTLQINSLKPEDTAVYYCATPWVTYCPENLLFSYWGQGTQVTVSS | G13# |
| 89 | QVKLEESGGGLVQPGGSLRLSCAASGFTFDDYAIGWFRQAPGKEREGVSCITSSDGSTYYADS VKGRFTISRDNANNTVHLQISNLKPEDTAVYYCATPWVTYCPENLLFSYWGQGTQVTVSS | G13-# |
| 90 | EVQLVESGGGLVQAGGSLTLSCAVSGSSFSIKAMGWYRLAPGKQRELVAAITSGGSTNYADSV KGRFTISRDSAKNTVYLQMNSLKPEDTAVYYCNGFFEYRGLEQLGPWGQGTQVTVSS | G31 |
| 91 | DVQLQASGGGLVQPGGSLRLSCAASGSIVGIRAMTWYRQAPGKQRELVAVLTSAGKPMYADSV KGRFTISRDNAKNTVYLQMNSLKPEDTAVYYCNADFGTPGSVVLGPWGQGTQVTVSS | G4 |

-continued

Annex 2

| Sequence | Amino acid sequence | Clone group |
|---|---|---|
| 92 | QVKLEESGGGLVQPGGSLRLSCAASGSILSIEAMGWYRQTLGKQRELVAAITSGDSTNYADFV KGRFTISRDKAKNMVYLQMNSLKPEDTAVYFCNALMVVRAGSNPEIGPWGQGTQVTVSS | NG2 |
| 93 | QVKLEESGGGLVQPGGSLRLSCAASGFTFDDYAIGWFRQAPGKEREGVSCISSSDGSTYYADS VKGRFTISRDNANNTVHLQISNLKPEDTAVYFCNALMVVRAGSNPEIGPWGQGTQVTVSS | G13-# |
| 94 | EVQLVESGGGLVQPGGSLRLSCVVSARGVSLDAVGWSRVAPGKQRDFVARIDRRGSTYYAVSV EGRSTISRDNAKNTVYLQLDTLKPEDTAVYYCFAWQGAETHWGLGTQVTVSS | G20 |
| 95 | QVKLEESGGGLVQAGGSLTLSCVASGSHFSFNDMGWYRQDPWKGRDLVAAITSSRNTLYVDSV KGRFTISRDDAKNTVYLQMNNLKPEDTAVYYCNPYPSPNNYWGQGTQVTVSS | NG3 |
| 96 | QVKLEESGGGLVQPGGSLRLSCAASGSPFTINAMGWYRQAPGKQRELVAAITRSGKTNYADSV KGRFTISGDNALTTVYLQMNNLQPEDTAVYYCNGFYGSEFGPWGQGTQVTVSS | NG4 |
| 97 | QVKLEESGGGLVQAGGSATLSCSAPGDTLSRYAVGWFRQGPGQERDFVASITWSGDYTYYKDS VKGRFTISRDSVNNMVYLRMNSLKPEDTALYYCAADKSSFRLRGPGLYDYRGQGTQVTVSS | NG5 |
| 98 | QVKLEESGGGLVQPGGSLRLSCAASGFTFDYYAIGWFRQAPGKEREGVSCISSRDGTTHYADS VKGRFTISRDNAKNTVYLQIDSLKPEDTAVYYCATPWVTYCPENLLFSYWGQGTQVTVSS | NG6# |
| 99 | QVKLEESGGGFVQPGGSLRLSCAASGFSLHYYAIGWFRQAPGKEREWVSAISNIDDDTYYEDS VKGRFTISRDNAKNTAYLQMNNLKPEDTAVYYCAADKDVVVVRTGLSESDYWGQGTQVTVSS | NG8 |
| 100 | QVKLEESGGGLVQAGGSLRLSCAASGSIFGINAMAWYRQAPGKQRELVAVITSGGRTMYAESV KGRFAISRDVAKNTVYLQMNSLKPEDTAVYYCNGDWGSEGRVDLGPWGQGTQVTVSS | NG9 |
| 101 | QVKLEESGGGLVQPGGTLRLSCAASGSIRSIGDMEWYRQAPGQQRELVASISAGPEMRSAGTP TYAKSVEGRFTISRDNIKNMMWLQMNSLRPEDTAVYSCNADVLTYYNGRYSRDVYWGQGTQVT VSS | NG10 |
| 102 | QVKLEESGGGLVQAGGSLRLSCAASSSIFSINMSWYRQAPGNERELVATITRHDSTHYSDSVK GRFAISRDDDKNTIYLQMNSLKPEDTAVYYCSGFFLDGSTWRPYWGQGTQVTVSS | G12-1 |
| 103 | DVQLQASGGGLVQPGGSLRLSCAASGRTLSGYAVAWFRQAPGKEREFVAAISSSDNSSPYYAN VVKGRFTISRDNAKNTVYLQMNSLQTEDTALYYCAARYGTKRYVAREYDSWGQGTQVTVSS | G17-1 |
| 104 | QVKLEESGGGLVQPGGSLRLSCAASRSIFSINAMAWYRQAPGKQRELVAYIRSSGTTMYADSV KGRFTISRDNAKNTVYLQMNSLKPEDTAVYYCNGDYSPPGSTYPDLGPWGQGTQVTVSS | NG11 |
| 105 | EVQLQASGGGLVQPGGSLRLSCAASGFTFDDYAIGWFRQAPGKEREGVSCITSSDFSTYYADS VKGRFTISRDNANNTVHLQISNLKPEDTAVYYCATPWVNYCPENLLFSYWGQGTQVTVSSQAQ VQLVESGGGLAQAGGSLRLSCTASGRTFSTYFMAWFRQPPGKEREYVGGIRWSDGVPHYTDSV KGRFTISRDNAKNTVYLQMNSLKSEDTABYFCASRGIADGSDFGSYGQGTQVTVSS | G15(bi) |
| 106 | QVKLEESGGGLVQAGGSLRLSCGASGIIFSATTMAWYRQAPGKQRELVALITSDWHTKYADSV KDRFSISRDNAKSTVHLQMNSLRSEDTAVYFCYARQAFSEPRQGQGTQVTVSS | G11 |
| 107 | QVQLVDSGGGLVQPGGSLRLSCAASGSSGRIDAMGWSRVAPGKQRDFVARLGSNGFTQYDISV EGRFTISGDVAKNTIYLQMDTLKPEDTAVYYCFAWLGQDTVWGQGTQVTVSS | NG12 |
| 108 | QVQLVDSGGGLVKAGASLRLSCAASGDALFNYAMGWFRQGPGKERDFVASVTRSGDNTYYKDS AKGRFTISRDDAKNTVYLQMNSLKPEDTAVYFCAADKSSFRLRGPGVYDYRGQGTQVTVSS | NG14 |
| 109 | DVQLVDSGGGLVQAGGSLRLSCAVSGSDGRVMLMGWYRQAPGQQRDLVASITSADYTTYAESV EGRFTISTDNNKNTVYLQMNSLKPEDTAVYFCKVIAATVWGQETQVRQGLTFWGQGTQVTVSS | NG13 |
| 110 | EVQLVESGGGLVQPGGSLRLSCVASGSISSARSMTWYRQALGKQRELVAVIMGGGSTMYADSV KGRFTISRDNAKNTVYLQMNSLKPEDTAVYYCNADWGGVGFPNLGPWGQGTQVTVSS | G21 |
| 111 | DVQLQASGGGLVQIGDSVRLSCIASGGTFRTYAIGWFRQAPGAEREFVAAISRRGNKDYAESV KGRFTVSRDNAENTVYLQMNSLKPDDMGVYYCAASARNFIGTQPLDYDYWGQGTQVTVSS | NG23 |
| 112 | QVKLEESGGGLVQAGGSLRLSCAASGWNLGNYALGWFRQAPGKEREFVAAIDWRHSSYYADSV KGRFTISRDNTKNMVYLQMSSLKLEDTRLYYCAASSLFPSSAPRQYDYWGQGTQVTVSS | NG15 |
| 113 | DVQLVDSGGGLVQAGGSLRLSCVASGRTFSNYAMGWYRRRPGLEREFVAAIVGSGDSTRYADS VKGRFTISRDNAKNTVYLQMNTLKPEDTAVYYCASSSDPRVYIASTLDYWGQGTQVTVSS | NG16 |
| 114 | QVQLVESGGGLVQAGGSLRLSCAASGRTFSMFIMGWFRQAPGKERELVAAISRNSNLTYYFQS VKGRFTISRDNAKNTVYLQMNSLKLEDTAVYYCNADYGPPVSIGPWGQGTQVTVSS | G23 |

Annex 2

| Sequence | Amino acid sequence | Clone group |
|---|---|---|
| 115 | QVKLEESGGGWVQPGGSLRLSCVVSGRILSIKAMGWYRQAPGKQREYVAGIVSSGNTNYADFV KGRFTISGDNAKNTVFLQMNSLKPEDTAVYYCNALVVVTSASGPELASWGQGTQVTVSS | NG17 |
| 116 | DVQLVDSGGGLAQAGGSLRLSCTASGRTFSTYFMAWFRQPPGKQRELVAYIRSGGTNYADSV KGRFTISRDIAKNTVYLQMNSLKPEDTAVYYCNADYSPPGSRFPDLGPWGQGTQVTVSS | G1-3 |
| 117 | QVKLEESGGGLVQPGGSLTLSCAASGFTLDNYAIAWFRQAPGREREWVSSTGSDGNLYTPSVR GRFTISRDNAKNTVYLQMNSLKPEDTAVYYCVAGKRPVITTWIALDAWGQGTQVTVSS | NG18 |
| 118 | DVQLVDSGGGLVQAGGSLRLSCAASGTFSSIDSMRWFRRAPGKEREFVAHITSTGRTNYADAV KGRFTISRDNAKNTMWLQMDNLKPDDTAVYYCNMVTTPYMHWGQGTQVTVSS | NG24 |
| 119 | QVKLEESGGGLVQAGGSLKLSCVASGSRFSENAMGQYHQAPDKQRTLVAAITSSRSTLYIDSV KGRFTISRDNAKNTVYLQMSNLKPEDTGVYYCNPYPSPNSYWGQGTQVTVSS | NG25 |
| 120 | QVKLEESGGGLVQPGGSLRLSCAASGLVFSANKMGWYRQAPGKQRELVARISTDGRTNYADSV KGRFTISRDNAEKTVFLQMNSLNPDDTAVYYCNANWLDKYDYWGQGTQVTVSS | NG19 |
| 121 | QVKLEESGGGLVEPGGSLRLSCVASGSISSARSMTWYRQAHGKQRELVAVITSGGSTMYADSV KGRFTISRDSAKNTVYLQMNSLKPEDTAVYYCNADWGEVGFVNLGPWGQGTQVTVSS | NG26 (G21-1) |
| 122 | EVQLVESGGGLVQPGGSLRLSCAASGSIFGFNGVAWFRQAPGKGRELVAVIRSGGNTYADSVK GRFTISRDNAKNTVYLQMNSLKPEDTAVYYCNVDYSPPGSLVPDLGPWGQGTQVTVSS | G18 |
| 123 | EVQLEESGGGLVQPGGSLRLSCAASGSTASINAMGWYRQAPGKQRELVAAITRGGSTNYADSV KGRFTISRDNAKNTVYLQMNSLKPEDTAVYSCNGLCSDDRCYGDSLFAPWGPGTQVTVSS | G16# |
| 124 | EVQLVESGGGLVQPGGSLRLSCLVSGRGVSLDAVGWSRVAPGKQRDFVARIDSRGSAYYADSV EGRFTISRDNAKNTVYLQVDTLKPEDTAVYYCFAYYGAQISFGPWGQGTQVTVSS | G24 |
| 125 | DVQLQASGGGLVQPGGSLRLSCVVSGRGVNLDAMGWSRVAPGKQRDFVAHIDDRGTAYYADFV KGRSTISRDNAKNTVYLQVDTLKPEDTAVYYCFAWQGAETYWGLGTRVTVSS | G19 |
| 126 | EVQLVESGGGLVQAGGSLRLSCVASGSIFSVNAVAWYRQAPGKQRELVAYIRRSGSTNYADSV KGRFTISRDNAKNTLYLQMNSLKPDDTAVYYCNAGRTGDRFNLVAYWGQGTQVTVSS | G5-1 |
| 127 | EVQLEESGGGLAQAGGSLRLSCTASGRTFSTYFMAWFRQPPGKEREYVGGIRWSDGVPHYADS VKGRFTISRDNAKNTVYLQMNSLKPEDTAVYYCNADYSPPGSRFPDLGPWGQGTQVTVSS | G26 |
| 128 | EVQLQASGGGLVQPGGSLRLSCVASGSIFSIKAMAWYRQAPGKQRELVAYIRSGGTTNYADSV KGRFTISRDIAKNTVYLQMNSLKSEDTAVYFCASRGIADGSDFGSYGQGTQVTVSS | G27 |
| 129 | EVQLVESGGGLVQAGASVRLSCAASGRANSLYAMGWFRQAPGKQRELVAYIRSGGTTNYADSV KGRFTISRDIAKNTVYLQMNSLKPEDTAVYYCNADYSPPGSRFPDLGPWGQGTQVTVSS | G1-2 |
| 130 | EVQLVESGGGLVQIGDSVRLSCIASGGTFRTYAMGWFRQAPGAEREFVAAISRRGNKTDYAES VKGRFTVSRDNAENTVYLQMNSLKPDDMGVYYCAASARNFIGTQPLDYDYWGQGTQVTVSS | G28 |
| 131 | QVKLEESGGGMVQAGGSLRLSCVASGRSFVGYFMAWFRQPPGKEREYVGGIRWSDGVPHYADS VKGRFTISRDNAKNTVYLQMNSLKSEDTAVYFCASRGIADGSDFGSYGQGTQVTVSS | G29 |
| 132 | QVKLVESGGGLVQPGGSLRLSCAASGSIFSINAMGWYRQAPGKQRELVAAITKSNNINYADSV KGRFTISRDNAKNTVYLWMNSLKPEDTAVYYCNGFFTLPGYSSEEFGPWGQGTQVTVSS | G2-1 |

Annex 3

| Sequence | Nucleotide acid sequence | Clone group |
|---|---|---|
| 133 | GAGGTACAGCTGGTGGAATCTGGGGGAGGATTGGCGCAGGCTGGGGGCTCTCTGAGACTCTCC TGTACAGCCTCTGGACGCACCTTCAGTACCTATTTCATGGCTGGTTCCGCCAGCCTCCAGGG AAAGAGCGTGAATACGTAGGCGGTATTAGGTGGAGTGATGGTGTTCCACACTATGCAGACTCC GTGAAGGGCCGATTCACCATCTCCAGAGACAACGCCAAGAACACGGTGTATTTGCAAATGAAC AGCCTGAAATCTGAGGACACGGCCGTTTATTTTTGTGCATCACGGGGTATTGCGGATGGATCT GACTTTGGTTCCTACGCCAGGGGACCCAGGTCACCGTCTCCTCA | G3 |
| 134 | GAGGTACAGCTGGTGGAATCTGGGGGAGGATTGGCGCAGGCTGGGGGCTCTCTGAGACTCTCC TGTACAGCCTCTGGACGCACCTTCAGTACCTATTTCATGGCCTGGTTCCGCCAGCCTCCAGGG AAAGAGCGTGAATACGTAGGCGGTATTAGGTGGAGTGATGGTGTTCCACACTATGCAGACTCC GTGAAGGGCCGATTCACCATCTCCAGAGACAACGCCAAGAACACGGTGTATTTGCAAATGAAC | G1 |

Annex 3

| Sequence | Nucleotide acid sequence | Clone group |
|---|---|---|
|  | AGCCTGAAATCTGAGGACACGGCCGTTTATTTTTGTGCATCAGGGGGTATTGCGGATGGATCT GACTTTGGTTCCTACGGCCAGGGGACCCAGGTCACCGTCTCCTCA |  |
| 135 | CAGGTAAAGCTGGAGGAGTCTGGGGGAGGCTTGGTGCAGCCTGGGGGGTCTCTAAGACTCTCC TGTGCAGCCTCTGGACTCGTCTTCAGTGCCAATACCATGGCCTGGTACCGCCGGGCTCCAGGG AAGCAGCGCGAGTTGGTCGCACGTATTAGCACTGACGGACGTACAAACTACGCGGACTCCGTG AAGGGCCGATTCACCATCTCCAGAGACAACCGCGAGAAGACGGTGTTTCTGCAAATGAACAGG CTGAACCCTGACGACACGGCCGTCTATTACTGTAATGCAAACTGGCTCAGTAAATTTGACTAC TGGGGCCAGGGGACCCAGGTCACCGTCTCCTCA | NG7 |
| 136 | CAGGTAAAGCTGGAGGAGTCTGGGGGAGGCTTGGTGCAGGCTGGGGGGTCTCTGAGACTCTCC TGTGTAGCCTCTGGAAGCATCTTCAGTGTCAATGCCGTGGCCTGGTACCGCCAGGCTCCAGGG AAACAGCGCGAGTTGGTCGCATATATACGTCGTAGTGGTAGCACAAACTATGCAGACTCCGTG AAGGGCCGATTCACCATCTCCAGAGACAACGCCAAGAACACGGTGTATCTGCAAATGAACAGC CTGAAACCTGAGGACACAGCCGTCTATTACTGTAATGCAGATTTCGGTAGCGACTATGTCGTC CTCGGTTCCTGGGGCCAGGGGACCCAGGTCACCGTCTCCTCA | G5 |
| 137 | CAGGTAAAGCTGGAGGAGTCTGGGGGAGGCTTGGTGCAGGCTGGGGGGTCTCTGAGACTCTCC TGTGCAGCCTCTGGAAGCATCTTCAGTATCAAAGCCTTGGCCTGGTACCGCCAGGCTCCAGGG AAGCAGCGCGAGTTGGTCGCATATATTACTAGTGGTGGTAACACAAACTATGCAGACTCCGTG AGGGGCCGATTCACCATCTCCAGAGACAACGCCAAGAACACGGTATATCTGCAAATGAACAGC CTGAAACCTGAGGACACAGCCGTCTATTACTGTAATGCAGATTTCGGAGAAGGGACTATCATA TCCCTTGGACCCTGGGGCCAGGGGACCCAGGTCACCGTCTCCTCA | G9 |
| 138 | CAGGTAAAGCTGGAGGAGTCTGGGGGAGGCTTGGTGCAGCCTGGGGGGTCTCTGAGACTCTCC TGTGCAGCCTCTGGAAGCGAATTCAGTATCAATGCCATGGCGTGGTACCGCCAGGCTCCAGGG AAGCAGCGCGAGTTGGTCGCAGCACTTACTAGTGGTGGTAACACTCACTATGCGGACTCCGTG AAGGGCCGATTCACCATCTCCAGAGACAACGCCAAGAACACGTGGTATCTGCAAATGAACAGC CTGAAACCTGAGGACACGGCCGTCTATTACTGTAATGCAGATTTCGGAACTGCGGGTTTGGTA GTGCTGGGTCCCTGGGGCCAGGGGACCCAGGTCACCGTCTCCTCA | G7 |
| 139 | CAGGTAAAGCTGGAGGAGTCTGGGGGAGGCTTGGTGCAGCCTGGGGGGTCTCTGAGACTCTCC TGTGCAGCCTCTGGAAGCATCGTCAGTATCAATGCCATGGCCTGGTACCGCCAGGCTCCAGGG AAGCAGCGCGAGTTGGTCGCATATATTCGTAGTAATGGCCGCACAAACTATGCAGACTCCGTG AAGGGCCGATTCACCATTTCCAGAGACAACGCCAAGAACACGGTGTATCTGCAAATGAACAGC CTGAAACTTGAGGACACGGCCGTCTATTACTGTAATGCAGACTACGGGCCTCCAGTATCCATT GGTCCTTGGGGCCAGGGGACCCAGGTCACCGTCTCCTCA | G6-2 |
| 140 | CAGGTAAAGCTGGAGGAGTCTGGGGGAGGCTTGGTGCAGGCTGGGGGGTCTCTGAGACTCTCC TGTGTAGTCTCTGGAAGTCTCCTCAGTATCAAAGCCATGGCCTGGTTCCGCCAGCCTCCAGGG AAGCAGCGCGAGTTGGTCGCAGCTGTTACTAGTGGTGGAAGCACACACTATTTAGACTCCGTG AAGGGCCGATTCACCATCTCCAGAGACAACGCCAACACGGTGCATCTGCAAATGAACAGCCTG AAACCTGAGGACACAGCTGTCTATTACTGTAATGCAGATTTCGGTACTGACTATGTCGACTTA GGGCCCTGGGGCCAGGGGACCCAGGTCACCGTCTCCTCA | G10 |
| 141 | CAGGTAAAGCTGGAGGAGTCTGGGGGAGGCTTGGTGCAGCCTGGGGGGTCTCTGAGACTCTCC TGTGCAGTCTCTGGAAGCATCTTCAGTATCAATGCCATGGGCTGGTACCGCCAGGCTCCAGGG AAACAGCGCGAGTTGGTCGCAGCTATTACTAAAAGTAATAACATAAACTATGCAGACTCCGTG AAGGGCCGATTCACCATCTCCACAGACAACGCCAAGAACACGGTGTATCTGCAAATGAACAGC CTGAAACCTGAGGACACGGCCGTCTATTACTGTAATGGATTCTTCGCTTTGCCTGGGTACAGT AGTGAAGAATTTGGTCCCTGGGGCCAGGGGACCCAGGTCACCGTCTCCTCA | G2 |
| 142 | GAGGTACAGCTGGTGGAATCTGGGGGAGGCTTGGTGCAGCCTGGGGGGTCTCTGAGACTCTCC TGTGTAGCCTCTGGAAACATCTTCGATATGAATCGGATGGGCTGGTACCGCCAGCCTCCAGGG AAGCAGCGCGAGTTGGTCGCAGATATTCGTGATGGCGGTTCTACAATTTATTCAGATTCCGTG AAGGGCCGATTCACCATCTCCAGAGACAACGCCAAGAACACGTGTATCTGCAAATGAACAGC CTGAAACCTGACGACACAGCCGTGTATTATTGTAATGCGGGCGGACAGGGGATCGTTTTAAT TTGGTGCGTATTGGGGCCAGGGGACCCAGGTCACCGTCTCCTCA | G8 |
| 143 | GATGTGCAGCTGCAGGCGTCTGGGGGAGGCTTGGTGCAGCACGGGGGCTCTCTGAGACTCTCC TGTGAAGCCTCTGGACGCACCTTCAGTGGCTATGCCATGGCCTGGTTCCGCCAGGCTCCAGGA AAGGAACATGAATTTGTAGCAGCTATTAGCTCAAGTAGTAATAGTGCCCCATACTATGCAAAT TCCGTGAAGGGCCGATTCACCATCTCCAGAGACAACGCCAAGAACACGGTTTATCTACAAATG AACAACCTACAAACTGAGGACACGGCCGTTTATTACTGTGCAGCCCGGTACGGTACGAAACGG TACGTCGCCCGGGAGTATGACTCGTGGGGCCAAGGGACCCAGGTCACCGTCTCCTCA | G17 |
| 144 | GATGTGCAGCTGCAGGCGTCTGGGGGAGGCGTCGTGCAGGCTGGGGGGTCTCTGAGACTCTCC TGTACAGCCTCTGGAAGCATCCGCAGTATCAATGGCATGGGCTGGTCGCGCGTGGCTCCAGGG AAGCAGCGCGACTTCGTCGCACGTATTGATAGTAGGGGTAGCGCATACTATGCAGACTCCGTA GAGGGCCGATTCACCATCTCCAGAGACAACGCCAAGAACACGGTGTATCTGCAAGTGGACACG CTGAAACCTGAGGACACGGCCGTCTATTATTGCTTTGCGTGGCAGGGTCCGGAAACATATTGG GGCCTGGGCACCCAGGTCACCGTCTCCTCA | G25 |

-continued

Annex 3

| Sequence | Nucleotide acid sequence | Clone group |
|---|---|---|
| 145 | CAGGTAAAGCTGGAGGAGTCTGGGGGAGGCTTGGTGCAGCCTGGGGGTCTCTGCGACTCTCC<br>TGTGCAGCCTCTGGAAGCATCGGCGATACCTATGCCATGGCCTGGTACCGCCAGGCTCCAGGG<br>AAGCAGCGCGACTTGGTCGCATATATTACTAATGGTGGTAGCACGGACTACGCAGCCTCCGTG<br>AAGGGCCGATTCACCATCTCCAGAGACAACGCCAAGAACACGGTCTATCTGCAAATGAACAGC<br>CTGAAACCTGAGGACACGGCCGTCTACTACTGTAATGGAGCTACCCGTCGTGCACAGTTAGTC<br>TTCGACTGGGGCCAGGGGACCCAGGTCACCGTCTCCTCA | NG1 |
| 146 | CAGGTAAAGCTGGAGGAGTCTGGGGGAGGATTGGTGCAGCACGGGGCTCTCTGAGACTCTCC<br>TGTGCAGCCTCTGGAGCCACCTTCAGTAACTATCCCATGGCCTGGTTCCGCCAGCCTCCAGGA<br>AAGGAGCGTGAATTTGTAGCAGCTATTAGCGTGAGTGCTAATAGTGCCCCATACTATGCAAAT<br>TCCGTGAAGGGCCGATTCACCATCTCCAGAGACAACGCCAAGAACACGGTTTATCTGCAAATG<br>AACAGCCTAAAAACTGAGGACACGGCCGTTTATTACTGTGCAGCCCGGTACGGTACGAAACGA<br>TACGTCGCCCGGGAGTATGACTCGTGGGGCCAGGGGACCCAGGTCACCGTCTCCTCA | NG20 |
| 147 | CAGGTAAAGCTGGAGGAGTCTGGGGGAGGCTTGGTGCAGCCTGGGGGGTCTCTGCGACTCTCC<br>TGCGCAGCCTCTGGAAGTAGCGTCAGTCTCAATGCCATGGGCTGGTCGCGCGTGCAACCAGGA<br>AGTACGCGCGACTTCGTCGCACGGATTGCTGCCGATGGTAGCACTCACTATGCAGACTCCGTG<br>AGGGGCCGGTTCACCATCTCCGGGGACGCCGCCAGGAACACGGTGTATCTACAAATGGATTCGC<br>TGAAACCCGAAGACACGGCCGTCTATTACTGTTTTGCGTGGCTGGGTACGGACACGTACTGGG<br>GCCAGGGGACCCAGGTCACCGTCTCCTCA | NG21 |
| 148 | CAGGTAAAGCTGGAGGAGTCTGGGGGAGGCTTGGTGCAGGCTGGGGGGTCTCTGACACTCTCC<br>TGTGCAGCCTCTGGAAGCATCGGCGATAACAATGCCATGGGCTGGTCCCGCACGCCTCCAGGG<br>AAGCAGCGCGAGTTCGTCGCACGTATAGATAGTGGGGGATCACACGCTATGCAGACTCCCTG<br>AAGGGCCGATTCACTGTCTCCAGAGACACCGGCAAGAACACGGTGTCTCTGCAAATGAACAGC<br>CTGAAAGCTGAGGACACAGGCGTCTATTACTGTTTTGCACATGTCGGTGGTACTATCTGGGGC<br>CAGGGGACCCAGGTCACCGTCTCCTCA | G14 |
| 149 | CAGGTAAAGCTGGAGGAGTCTGGGGGAGGCTTGGTGCAGCCTGGGGGTCTCTGAGACTCTCC<br>TGTTTACCCTCTGGAGGCATCTTCACTATCAATAGCATGGGCTGGTATCGGCAGGCTCCAGGG<br>AAACAGCGCGAGTTGGTCGCAAGTATCACTGGTGGTGGTAGTTCACGTTATGCAGACTCCGTG<br>AAGGGCCGATTCATCATGTCCAGAGACAACGCCAAGAACACGGTGTATCTGCAAATGAACAGC<br>CTGAAACCTGAGGACACGGCCGTCTATTACTGTAATACAATCCCCCGGCCCGGACCCAAAGC<br>GATCATGGGGAGTGGTATFACTACTGGGGCCAGGGGACCCAGGTCACCGTCTCCTCA | NGS1 |
| 150 | CAGGTAAAGCTGGAGGAGTCTGGGGGAGGCTTGGTGCAGGCTGGAGGGTCTCTGAGACTCTCC<br>TGCGCAGCCTCTAGCAGCATCTTCAGTATCAATATGAGCTGGTACCGCCAGGCTCCAGGGAAC<br>GAGCGCGAGTTGGTCGCAACTATTACACGGCATGATAGCACACACTATTCAGACTCCGTGAAC<br>GGCCGATTCACCATCTCCAGAGACGACGACAAGAACACGATATATCTGCAAATGAACAGCCTG<br>AAACCTGAGGACACGGCCGTCTATTACTGTTCTGGGTTTTTTCTGGACGGTAGTACCTGGCAC<br>CCATATTGGGGCCAGGGGACCCAGGTCACCGTCTCCTCA | G12 |
| 151 | GAGGTACAGCTGGTGGAATCTGGGGGAGGCTTGGTGCAGCCTGGGGGTCTCTGAGACTCTCC<br>TGTGCAGCCTCTGGAAGCATCGTCAGTATCAATGCCATGGCCTGGTACCGCCAGGCTCCAGGG<br>AAGCAGCGCGAGTTGGTCGCATATATTCGTAGTAATGGCACAAACTATGCAGACTCCGTG<br>AAGGGCCGATTCACCATTTCCAGAGACAACGCCAAGAACACGGTCTACCTGCAAATGAACAGC<br>CTGAAACTTGAGGACACGGCCGTCTATTATTGTAATGGATTCTTCACTTTGCCTGGCTACAGT<br>AGTGAAGAATTTGGTCCCTGGGGCCAGGCGACCCAGGTCACCGTCTCCTCA | G6 |
| 152 | GAGGTACAGCTGGTGGAATCTGGGGGAGGCTTGGTGCAGCCTGGAGGGTCTCTGAGACTCTCC<br>TGTGCAGCCTCTGAGAGCATCTTCAGTATCAACCCCATGGGCTGGTACCGCCAGGCTCCAGGG<br>AAGCAGCGCGAGTATGTCGCAGGCATTACTAAGGGTGGGCGTACAAACTATGCAGACTCCGTG<br>AAGGGCCGATTCACCATCTCCAGAGACGACGCCAAGAATACGGTGTATCTGCAAATGAACAGC<br>CTGAAACCTGAAGACACGGCCGTCTATTACTGTAATGGTTTGTGCTCAGGCAGAGAGTGTTAT<br>GGGGACTCCCTTTTTGCCGCCTGGGGCCAGGGGACCCAGGTCACCGTCTCCTCAGGATCCGAA<br>CAAAAACTGATCAGCGAAGAAGATCTGAACCATCACCATCACCATTAGTGA | G22# |
| 153 | GAGGTACAGCTGGTGGAATCTGGGGGAGGCTTGGTGCAGCCTGGGGGTCTCTGAGACTCTCC<br>TGTGCAGCCTCTGGAAGCATCGTCAGTATCAATGCCATGGCCTGGTACCGCCAGGCTCCAGGG<br>AAGCAGCGCGAGTTGGTCGCATATATTCGTAGTAATGGCCGCACAAACTATGCAGACTCCGTG<br>AAGGGCCGATTCACCATTTCCAGAGACAACGCCAAGAACACGGTGTATCTGCAAATGAACAGC<br>CTGAAACTTGAGGACACGGCCGTCTATTACTGTTCTGGGTTTTTTCTGGACGGTAGTACCTGG<br>CACCCATATTGGGGCCAGGGCACCCAGGTCACCGTCTCCTCA | G6-1 |
| 154 | GAGGTACAGCTGGTGGAATCTGGGGGAGGATTGGCGCAGGCTGGGGGCTCTCTGAGACTCTCC<br>TGTGCAGCCTCTGGATTCACTTTCGATGATTATGCCATAGGCTGGTTCCGCCAGGCCCCAGGG<br>AAGGAGCGTGAGGGGGTCTCATGTATTAGTGATGGTAGCACACACTATGCAGACTCC<br>GTGAAGGGCCGATTCACCATCTCCAGAGACAATGCCAGGAACACGGTGACTCTGCAAATAAAC<br>AGCCTGAAACCTGAGGATACGGCCGTTTATTACTGTGCGACCCCCTGGGTGACCTATTGCCCC<br>GAGAACCTTCTGTTTAGTTACTGGGGCCAGGGGACCCAGGTCACCGTCTCCTCA | G13# |
| 155 | CAGGTAAAGCTGGAGGAGTCTGGGGGAGGCTTGGTGCAGCCTGGGGGGTCTCTGAGACTCTCC<br>TGTGCAGCCTCTGGATTCACTTTCGATGATTATGCCATAGGCTGGTTCCGCCAGGCCCCAGGG | G13-2# |

Annex 3

| Sequence | Nucleotide acid sequence | Clone group |
|---|---|---|
|  | AAGGAGCGCGAGGGGGTCTCATGTATTACGAGTAGTGATGGTAGCACATACTATGCAGACTCT GTGAAGGGCCGATTCACCATCTCCAGAGACAATGCCAACAACACGGTGCATCTGCAAATAAGC AACCTAAAACCTGAGGATACGGCCGTTTATTACTGTGCGACCCCTGGGTGACCTACTGCCCC GAGAACCTTCTGTTTAGTTACTGGGGCCAGGGGACCCAGGTCACCGTCTCCTCA |  |
| 156 | GAGGTACAGCTGGTGGAATCTGGGGGAGGCTTGGTGCAGGCTGGGGGTCTCTGACACTCTCC TGTGCAGTCTCTGGAAGCAGCTTCAGTATCAAGGCCATGGGCTGGTACCGCCTGGCTCCAGGG AAGCAGCGCGAGTTGGTCGCAGCAATTACTAGTGGTGGTAGCACGAACTATGCGGACTCCGTG AAGGGCCGATTCACCATCTCCAGAGACAGCGCCAAGAACACGGTGTATCTGCAAATGAACAGC CTGAAACCTGAGGACACAGCCGTCTATTACTGTAATGGTTTTTTTCGAGTATAGGGGTCTTGAA CAATTGGGCCCCTGGGGCCAGGGGACCCAGGTCACCGTCTCCTCA | G31 |
| 157 | GATGTGCAGCTGCAGGCGTCTGGGGGAGGCTTGGTGCAGCCTGGGGGGTCTCTGAGACTCTCC TGTGCAGCCTCTGGAAGCATCGTCGGTATCCGTGCCATGACGTGGTACCGCCAGGCTCCAGGG AAGCAGCGCGAGTTGGTCGCAGTTCTTACTAGTGCTGGTAAACCTATGTATGCCGACTCCGTG AAGGGCCGATTCACCATCTCCAGAGACAACGCCAAGAACACGGTATATCTGCAAATGAACAGC CTGAAACCTGAGGACACGGCCGTCTATTACTGTAACGCAGATTTCGGGACTCCGGGTTCAGTA GTACTGGGTCCTTGGGGCCAGGGGACCCAGGTCACCGTCTCCTCA | G4 |
| 158 | CAGGTAAAGCTGGAGGAGTCTGGGGGAGGCTTGGTGCAGCCTGGGGGGTCTCTGAGACTCTCC TGTGCAGCCTCTGGAAGCATCCTCAGTATCGAGGCCATGGGCTGGTACCGCCAGACTCTTGGG AAGCAGCGCGAATTGGTCGCAGCTATTACTAGTGGTGATAGCACAAACTATGCAGACTTCGTG AAGGGCCGATTCACCATCTCCAGAGACAAGGCCAAGAACATGGTGTATCTGCAAATGAACAGC CTGAAACCTGAGGACACGGCCGTCTATTTCTGTAATGCCCTAATGGTAGTTAGGGCTGGCTCG AATCCCGAAATTGGTCCCTGGGGCCAGGGGACCCAGGTCACCGTCTCCTCA | NG2 |
| 159 | CAGGTAAAGCTGGAGGAGTCTGGGGGAGGCTTGGTGCAGGCTGGGGGTCTCTGAGACTCTCC TGTGCAGCCTCTGGATTCACTTTCGATGATTATGCCATAGGCTGGTTCCGCCAGGCCCCAGGG AAGGAGCGTGAGGGGGTCTCATGTATTAGTAGTAGTGATGGTAGCACATACTATGCAGACTCC GTGAAGGGCCGATTCACCATCTCCAGAGACAATGCCAAGAACACGGTGTATCTGCAAATAAAC AGCCTGAAACCTGAGGATACGGCCGTTTATTACTGTGCGACCCCTGGGTGACCTACTGCCCC GAGAACCTTCTGTTTAGTTACTGGGGCCAGGGGACCCAGGTCACCGTCTCCTCA | G13-3# |
| 160 | GAGGTACAGCTGGTGGAATCTGGGGGAGGATTGGTGCAGCCTGGGGGGTCTCTGAGACTGTCC TGTGTAGTCTCTGCAAGGGGCGTCAGTCTCGATGCCGTGGGCTGGTCGCGCGTGGCTCCAGGG AAGCAGCGCGACTTCGTCGCACGTATTGATCGAAGGGGTAGTACATACTATGCAGTGTCCGTA GAGGGCCGATCACCATCTCCAGAGACAACGCCAAGAACACGGTGTATCTGCAACTGGACACG CTGAAACCTGAGGACACGGCCGTCTATTATTGTTTTGCATGGCAGGGTGCGGAAACACATTGG GGCCTGGGGACCCAGGTCACCGTCTCCTCA | G20 |
| 161 | CAGGTAAAGCTGGAGGAGTCTGGGGGAGGCTTGGTGCAGGCTGGGGGGTCTCTGACCCTCTCC TGTGTAGCCTCTGGAAGCCACTTCAGTTTCAATGACATGGGCTGGTATCGCCAGGATCCGTGG AAGGGGCGCGACTTGGTCGCGGCTATTACTAGTAGTCGTAACACACTTTATGTAGACTCCGTG AAGGGCCGGTTCACCATCTCCAGAGACGACGCCAAGAACACGGTGTATCTACAAATGAACAAC CTGAAACCTGAGGACACAGCCGTCTATTACTGTAACCCGTACCCTTCCCCAAATAACTACTGG GGCCAGGGGACCCAGGTCACCGTCTCCTCA | NG3 |
| 162 | CAGGTAAAGCTGGAGGAGTCTGGGGGAGGCTTGGTGCAGCCTGGGGGGTCTCTGAGACTCTCC TGTGCAGCCTCTGGAAGCCCCTTCACGATCAATGCCATGGGCTGGTACCGCCAGGCTCCAGGG AAGCAGCGCGAGTTGGTCGCAGCAATTACTCGTAGTGGTAAGACGAACTATGCAGACTCCGTG AAGGGCCGATTCACCATCTCCGGAGACAACGCCCTGACCACGGTGTATCTGCAAATGAACAAC CTGCAACCTGAAGACACGGCCGTCTATTACTGTAATGGGTTCTACGGGTCTGAATTTGGGCCC TGGGGCCAGGGGACCCAGGTCACCGTCTCCTCA | NG4 |
| 163 | CAGGTAAAGCTGGAGGAGTCTGGGGGAGGATTGGTCCAGGCTGGGGGCTCTGCGACGCTCTCC TGTTCAGCCCCTGGAGACACCTTAAGTAGATACGCCGTGGGCTGGTTCCGCCAGGGGCCAGGG CAGGAGCGTGATTTTGTAGCATCCATTACCTGGAGTGGTGATTACACATACTATAAAGACTCC GTGAAGGGCCGATTCACCATCTCCAGAGACAGTGTCAACAACATGGTGTATCTGCGAATGAAC AGCCTGAAACCTGAGGACACGGCCCTGTATTACTGTGCAGCCGATAAGAGTTCCTTTAGACTC CGAGGCCCTGGATTATATGACTACAGGGGCCAGGGGACCCAGGTCACCGTCTCCTCA | NG5 |
| 164 | CAGGTAAAGCTGGAGGAGTCTGGGGGAGGCTTGGTGCAGCCTGGGGGGTCTCTGAGACTCTCC TGTGCAGCCTCTGGATTCACTTTCGATTATTATGCCATAGGCTGGTTCCGCCAGGCCCCAGGG AAGGAGCGCGAGGGGGTCTCATGTATTAGTAGTAGGGATGGTACCACCCACTATGCAGACTCC GTGAAGGGCCGATTCACCATCTCCAGAGACAATGCCAAGAACACGGTGTATCTGCAAATAGAC AGCCTGAAACCTGAGGATACGGCCGTTTATTACTGTGCGACCCCTGGGTGACCTACTGCCCC GAGAACCTTCTGTTTAGTTACTGGGGCCAGGGGACCCAGGTCACCGTCTCCTCA | NG6# |
| 165 | CAGGTAAAGCTGGAGGAGTCTGGGGGAGGCTTCGTACAGCCTGGGGGTCACTGAGACTCTCC TGTGCAGCCTCGGGATTCAGTTTTGCATTATTATGCCATAGGCTGGTTCCGCCAGGCCCCAGGG AAGGAGCGCGAGTGGGTCTCTGCCATTAGTAATATTGATGATGACACATACTATGAAGACTCC GTGAAGGGCCGATTCACCATCTCCAGAGACAACGCCAAGAACACGGCGTATCTGCAAATGAAC AACCTGAAACCTGAGGACACGGCCGTTTATTACTGTGCAGCAGATAAGGATGTAGTGGTAGTG CGTACGGGTCTCAGCGAGTCTGACTATTGGGGCCAGGGGACCCAGGTCACCGTCTCCTCA | NG8 |

Annex 3

| Sequence | Nucleotide acid sequence | Clone group |
|---|---|---|
| 166 | CAGGTAAAGCTGGAGGAGTCTGGGGGAGGCTTGGTGCAGGCTGGGGGGTCTCTGAGACTCTCC<br>TGTGCAGCCTCTGGAAGCATCTTCGGTATCAATGCCATGGCCTGGTACCGCCAGGCTCCAGGG<br>AAGCAGCGCGAACTGGTCGCAGTTATTACCAGTGGTGGACGCACAATGTATGCAGAGTCCGTG<br>AAGGGCCGATTCGCCATCTCCAGAGACGTCGCCAAGAACACGGTGTATCTGCAAATGAACAGC<br>CTGAAACCTGAAGACACAGCCGTCTATTACTGTAATGGAGACTGGGGGTCGGAGGGTAGGGTG<br>GACCTTGGACCCTGGGGCCAGGGGACCCAGGTCACCGTCTCCTCA | NG9 |
| 167 | CAGGTAAAGCTGGAGGAGTCTGGGGGAGGCTTGGTGCAGCCTGGGGGACGCTGAGACTCTCC<br>TGTGCCGCCTCGGGAAGCATTCGCAGTATCGGCGACATGGAGTGGTACCGCCAGGCTCCAGGA<br>CAGCAGCGCGAGTTGGTCGCAAGTATTAGTGCTGGCCCTGAGATGCGTAGTGCTGGTACCCCA<br>ACTATGCAAAGTCCGTGGAAGGGCCGATTCACCATCTCCAGAGACAACATCAAGAACATGATG<br>TGGCTGCAAATGAACAGCCTGAGACCTGAAGACACGGCCGTCTATTCCTGTAATGCCGACGTT<br>CTGACGTACTATAATGGTAGATACTCCCGAGATGTCTACTGGGGCCAGGGGACCCAGGTCACC<br>GTCTCCTCA | NG10 |
| 168 | CAGGTAAAGCTGGAGGAGTCTGGGGGAGGCTTGGTGCAGGCTGGGGGGTCTCTGAGACTCTCC<br>TGCGCAGCCTCTAGCAGCATCTTCAGTATCAATATGAGCTGGTACCGCCAGGCTCCAGGGAAC<br>GAGCGCGAGTTGGTCGCAACTATTACACGACATGATAGTACACACTATTCAGACTCCGTGAAG<br>GGCCGATTCGCCATCTCCAGAGACGACGACAAGAACACGGATATATCTGCAAATGAACAGCCTG<br>AAACCTGAGGACACGGCCGTCTATTACTGTTCTGGATTTTTTCTGGACGGTAGTACCTGGCGG<br>CCATATTGGGGCCAGGGGACCCAGGTCACCGTCTCCTCA | G12-1 |
| 169 | GATGTGCAGCTGCAGGCGTCTGGGGGAGGCTTGGTGCAGCCTGGGGGTCTCTGAGACTCTCC<br>TGTGCAGCCTCTGGACGCACCCTCAGTGGCTATGCCGTGGCCTGGTTCCGCCAGGCTCCAGGA<br>AAGGGAGCGTGAGTTTGTAGCAGCCATTAGCTCGAGTGATAATAGTAGCCCATATTATGCAAAT<br>GTCGTGAAGGGTCGATTCACCATCTCCAGAGACAACGCCAAGAACACGGTTTATCTGCAAATG<br>AACAGCCTGCAAACTGAGGACACGGCCCTTTATTACTGTGCAGCCCGGTACGGTACGAAACGG<br>TACGTCGCCCGGGAGTATGACTCGTGGGTCAGGGGACCCAGGTCACCGTCTCCTCA | G17-1 |
| 170 | CAGGTAAAGCTGGAGGAGTCTGGGGGAGGCTTGGTGCAGCCTGGGGGGTCTCTGAGACTCTCC<br>TGTGCAGCCTCTAGAAGCATCTTCAGTATCAATGCCATGGCCTGGTACCGCCAGGCTCCAGGG<br>AAGCAGCGCGAGTTGGTCGCATATATTCGTAGTAGTGGTCACACAATGTATGCGGATTCCGTG<br>AAGGGCCGATTCACCATCTCCAGAGACAACGCCAAGAACACGGTGTATCTGCAAATGAACAGC<br>CTGAAACCTGAGGACACGGCCGTCTATTATTGTAACGGAGATTACTCCCGCCCGGCAGCACG<br>TACCCTGACTTAGGTCCCTGGGGCCAGGGGACCCAGGTCACCGTCTCCTCA | NG11 |
| 171 | GAGGTGCAGCTGCAGGCGTCTGGGGGAGGCTTGGTGCAGCCTGGGGGGTCTCTGAGACTCTCC<br>TGTGCAGCCTCTGGATTCACTTTTCGATGATTATGCCATAGGCTGGTTCCGCCAGGCCCCAGGG<br>AAGGAGCGCGAGGGGGTCTCATGTATTACGAGTAGTGATGGTAGCACATACTATGCAGACTCT<br>GTGAAGGGCCGATTCACCATCTCTAGAGACAATGCCAACAACACGGTGCATCTGCAAATAAGC<br>AACCTAAAACCTGAGGATACGGCCGTTTATTACTGTGCGACCCCCTGGGTGAACTACTGCCCC<br>GAGAACCTTCTGTTTAGTTACTGGGGCCAGGGGACCCAGGTCACCGTCTCCTCACAGGCCCAG<br>GTACAGCTGGTGGAATCTGGGGGAGGATTGGCGCAGGCTGGGGGCTCTCTGAGACTCTCCTGT<br>ACAGCCTCTGGACGCACCTTCAGTACCTATTTCATGGCCTGGTTCCGCCAGCCTCCAGGGAAA<br>GAGCGTGAATACGTAGGCGGTATTAGGTGGAGTGATGGTGTTCCACACTATACAGACTCCGTG<br>AAGGGCCGATTCACCATCTCCAGAGACAACGCCAAGAACACGGTGTATTTGCAAATGAACAGC<br>CTGAAATCTGAGGACACGGCCGTTTATTTTTGTGCATCACGGGGTATTGCGGATGGATCTGAC<br>TTTGGTTCCTACGGCCAGGGGACCCAGGTCACCGTCTCCTCAGGATCCGAACAAAAACTGATC<br>AGCGAAGAAGATCTGAACCATCACCATCACCATTAGTGA | G15(bi) |
| 172 | CAGGTAAAGCTGGAGGAGTCTGGGGGAGGCTTGGTGCAGGCTGGGGGGTCTCTGAGACTCTCC<br>TGTGGAGCATCTGGAATTATTTTTAGTGCCACTACCATGGCCTGGTACCGCCAGGCTCCAGGG<br>AAGCAGCGCGAGTTGGTCGCACTGATTACTAGTGATTGGCACACAAAGTATGCAGACTCCGTG<br>AAGGACCGATTCTCCATTTCCAGAGACAACGCCAAGAGCACGGTGCACCTGCAAATGAACAGC<br>CTGAGATCTGAAGACACAGCAGTCTATTTTTGTTATGCCCGCCAAGCCTTCAGTGAGCCTCGT<br>TGGGGCCAGGGGACCCAGGTCACCGTCTCCTCA | G11 |
| 173 | CAGGTACAGCTGGTGGATTCTGGGGGAGGCTTGGTGCAGCCTGGGGGGTCTCTGAGATTGTCC<br>TGTGCAGCCTCTGGAAGCAGCGGCAGAATCGATGCCATGGGCTGGTCGCGCGTGGCTCCAGGG<br>AAGCAGCGCGACTTCGTCGCACGTCTTGGCAGTAATGGATTCACACAGTATGACATCTCCGTG<br>GAGGGCCGATTCACCATCTCCGGGACGTCGCCAAGAATACGATATATCTGCAAATGGACACG<br>CTGAAACCTGAGGACACGGCCGTCTATTACTGTTTTGCGTGGCTGGGGCAAGATACCGTGTGG<br>GGCCAGGGGACCCAGGTCACCGTCTCCTCA | NG12 |
| 174 | CAGGTACAGCTGGTGGATTCTGGGGGAGGATTGGTAAAGGCTGGGGCATCTCTGAGACTCTCC<br>TGTGCAGCCTCTGGAGACGCCTTATTTAACTACGCCATGGGCTGGTTTCGCCAGGGGCCAGGG<br>AAGGAGCGTGACTTTGTAGCATCTGTTACCAGGAGTGGTGATAATACATACTATAAAGACTCC<br>GCGAAGGGCCGATTCACCATCTCCAGAGACGACGCCAAGAACACGGTATATCTGCAAATGAAC<br>AGCCTGAAACCTGAGGACACGGCCGTTTATTTCTGTGCAGCAGATAAGAGTTCCTTTAGGCTC<br>CGAGGCCCTGGAGTATAFGACTACAGGGGCCAGGGGACCCAGGTCACCGTCTCCTCA | NG14 |
| 175 | CAGGTACAGCTGGTGGATTCTGGGGGAGGCTTGGTGCAGGCTGGGGGGTCTCTGAGACTCTCC<br>TGTGCAGTCTCTGGAAGCGACGGCCGAGTCATGCTCATGGGCTGGTACCGCCAGGCTCCAGGG | NG13 |

Annex 3

| Sequence | Nucleotide acid sequence | Clone group |
|---|---|---|
|  | CAGCAGCGCGACCTGGTCGCATCTATTACTAGTGCAGATTACACAACCTATGCAGAATCCGTC GAGGGCCGATTCACCATCTCCACAGACAACAACAAGAACACAGTGTATCTACAAATGAACAGC CTGAAGCCTGAAGCACAGCCGTCTATTTTTGTAAAGTAATTGCGGCGACGGTCTGGGGCCAG GAGACCCAGGTCAGGCAGGGTTTGACATTCTGGGGCCAGGGGACCCAGGTCACCGTCTCCTCA |  |
| 176 | GAGGTACAGCTGGTGGAATCTGGGGGAGGCTTGGTGCAGCCTGGGGGTCTCTGAGACTCTCC TGTGTAGCCTCTGGAAGCATCTCCAGTGCCAGATCCATGACCTGGTACCGCCAGGCTCTAGGG AAGCAGCGCGAGTTGGTCGCAGTGATTATGGGTGGCGGTAGCACGATGTATGCAGACTCCGTG AAGGGCCGATTCACCATCTCCAGAGACAACGCCAAGAACACGGTGTATCTACAAATGAACAGC CTGAAACCTGAGGACACGGCCGTCTATTATTGTAATGCAGACTGGGGGGGAGTCGGGTTTCCG AACTTAGGTCCCTCCCGCCACCGCACCCAGGTCACCGTCTCCTCA | G21 |
| 177 | GATGTGCAGCTGCAGGCGTCTGGGGGAGGATTGGTGCAAATTGGGGACTCTGTGAGACTCTCC TGTATAGCCTCTGGAGGCACCTTCAGAACTTATGCTATCGGTTGGTTCCGCCAGGCTCCAGGG GCTGAGCGTGAATTTGTAGCTGCCATTAGCCGGCGCGGTAATAAGACAGATTATGCAGAGTCC GTGAAGGGCCGATTCACAGTCTCCAGAGACAACGCCGAGAATACGGTGTATTTGCAAATGAAC AGCCTGAAACCTGATGACATGGGCGTTTATTACTGTGCAGCGTCGGCGCGTAATTTCATCGGC ACCCAGCCACTTGATTATGACTACTGGGGCCAGGGGACCCAGGTCACCGTCTCCTCA | NG23 |
| 178 | CAGGTAAAGCTGGAGGAGTCTGGGGGAGGATTGGTACAGGCTGGGGGCTCTCTGAGACTCTCC TGTGCAGCCTCTGGATGGAACCTTGGTAATTATGCCTTGGGCTGGTTCCGCCAGGCTCCAGGG AAGGAGCGTGAGTTTGTAGCAGCTATCGACTGGCGTCATAGTTCATACTATGCAGACTCCGTG AAGGGCCGATTCACCATCTCCAGAGACAACACCAAGAACATGGTGTATCTGCAAATGAGCAGC CTGAAACTTGAGGACACGCGCCTTTATTACTGTGCAGCATCAAGCCTATTCCCTAGTAGTGCT CCCCGTCAGTATGACTACTGGGGCCAGGGGACCCAGGTCACCGTCTCCTCA | NG15 |
| 179 | CAGGTACAGCTGGTGGATTCTGGGGGAGGATTGGTGCAGGCTGGGGGCTCTCTGAGACTCTCC TGTGTAGCCTCTGGACGCACCTTCAGTAATTATCCATGGGCTGGTACCGCCGACGTCCAGGG CTGGAGCGTGAATTTGTAGCAGCTATTGTTGGGAGTGGTGATAGCACAAGGTATGCAGACTCC GTGAAGGGCCGATTCACCATCTCCAGAGACAACGCCAAGAACACGGTGTATCTGCAAATGAAC ACGCTGAAACCTGAGGACACGGCCGTTTATTACTGTGCGTCATCCTCCGACCCGCGGGTTTAT ATAGCAAGTACTCTCGATTACTGGGGCCAGGGGACCCAGGTCACCGTCTCCTCA | NG16 |
| 180 | CAGGTACAGCTGGTGGAATCTGGGGGAGGATTGGTGCAGGCTGGGGGCTCTCTGAGACTCTCC TGTGCAGCCTCTGGACGCACCTTCAGTATGTTTATCATGGGCTGGTTCCGCCAGGCTCCAGGG AAGGAGCGTGAATTAGTAGCAGCTATTAGCCGGAATAGTAATCTCACATACTATTTTCAGTCC GTGAAAGGCCGATTCACCATCTCCAGAGACAACGCCAAGAACACGGTGTATTTGCAAATGAAC AGCCTGAAACTTGAGGACACGGCCGTCTATTACTGTAATGCAGACTACGGGCCTCCAGTATCC ATTGGTCCTTGGGGCCAGGGGACCCAGGTCACCGTCTCCTCA | G23 |
| 181 | CAGGTAAAGCTGGAGGAGTCTGGGGGAGGCTGGGTGCAGCCTGGGGGGGTCTCTGAGACTCTCC TGTGTAGTCTCTGGAAGGATCCTCAGTATCAAGGCCATGGGCTGGTACCGCCAGGCTCCTGGG AAGCAGCGCGAGTACGTCGCAGGTATTGTTAGCAGTGGTAATACAAACTATGCAGACTTCGTG AAGGGCCGATTCACCATCTCCGGAGACAACGCCAAGAACACGGTGTTTCTGCAAATGAACAGC CTGAAACCTGAAGACACGGCCGTCTATTACTGTAATGCCCTAGTGGTCGTTACTAGTGCCTCG GGTCCCGAGTTGGCTTCCTGGGGCCAGGGGACCCAGGTCACCGTCTCCTCA | NG17 |
| 182 | GATGTACAGCTGGTGGATTCTGGGGGAGGATTGGCGCAGGCTGGGGGCTCTCTGAGACTCTCC TGTACAGCCTCTGGACGCACCTTCAGTACCTATTTCATGGCCTGGTTCCGCCAGCCTCCAGGG AAGCAGCGCGAGTTGGTCGCATACATTCGTAGTGGTGGTACGACAAACTATGCAGACTCCGTG AAGGGCCGATTCACCATCTCCAGAGACATCGCCAAGAACACGGTGTATCTGCAAATGAACAGC CTGAAACCTGAGGACACGGCCGTCTATTACTGCAATGCAGATTACTCCCCGCCCGGCAGCCGG TTCCCTGACTTAGGTCCCTGGGGCCAGGGGACCCAGGTCACCGTCTCCTCA | G1-3 |
| 183 | CAGGTAAAGCTGGAGGAGTCTGGGGGAGGCTTGGTGCAGCCTGGGGGGTCTCTGACACTCTCC TGCGCAGCCTCTGGATTCACCTTGGATAATTATGCCATAGCGTGGTTCCGCCAGGCCCCAGGG AGGGAGCGCGAGTGGGTCTCATCAACTGGTAGTGATGGTAACTTATATACACCGTCCGTGAGG GGCCGATTCACCATTTCCAGAGACAACGCCAAGAACACGGTGTATCTGCAAATGAACAGCCTG AAACCTGAGGACACGGCCGTTTATTATTGTGTAGCAGGGAAGAGACCGGTAATTACTACATGG ATTGCTTTGGACGCATGGGGCCAGGGGACCCAGGTCACCGTCTCCTCA | NG18 |
| 184 | GATGTACAGCTGGTGGATTCTGGGGGAGGCTTGGTGCAGGCTGGGGGGTCTCTGAGACTCTCC TGTGCAGCCTCTGGAACATTCTCCAGTATCGATTCCATGCGCTGGTTCCGGCGGCTCCAGGA AAGGAGCGCGAATTTGTCGCACATATTACTAGCACGGGTAGGACAAACTATGCAGACGCCGTG AAGGGCCGATTTACCATCTCTAGAGACAACGCCAAGAACACGATGTGGCTGCAAATGGACAAC CTGAAACCTGACGACACGGCCGTCTATTATTGCAATATGGTGACGACTCCTTATATGCACTGG GGCCAGGGGACCCAGGTCACCGTCTCCTCA | NG24 |
| 185 | CAGGTAAAGCTGGAGGAGTCTGGGGGAGGCTTGGTGCAGGCTGGGGGGTCTCTGAAACTCTCC TGTGTAGCCTCTGGAAGCCGCTTCAGTGAAAATGCCATGGGCTGGTATCACCAGGCTCCAGAC AAACAGCGCACCTTGGTCGCAGCTATTACTAGTAGTCGTAGCACTCTTTATATAGACTCCGTG AAGGGCCGCTTCACCATCTCCAGAGACAACGCCAAGAACACGGTATATCTGCAAATGAGCAAC CTGAAACCTGAGGACACGGCCGTCTATTACTGTAACCCGTACCCTTCCCCAAATTCCTACTGG GGCCAGGGGACCCAGGTCACCGTCTCCTCA | NG25 |

Annex 3

| Sequence | Nucleotide acid sequence | Clone group |
|---|---|---|
| 186 | CAGGTAAAGCTGGAGGAGTCTGGGGGAGGCTTGGTGCAGCCTGGGGGGTCTCTAAGACTCTCC<br>TGTGCAGCCTCTGGACTCGTCTTCAGTGCCAATAAGATGGGCTGGTACCGCCAGGCTCCAGGG<br>AAGCAGCGCGAGTTGGTCGCACGTATTAGCACTGACGGACGTACAAACTATGCGGACTCCGTG<br>AAGGGCCGATTCACCATCTCCAGAGACAACGCCGAGAAGACGGTGTTTCTGCAAATGAACAGC<br>CTGAATCCTGACGACACGGCCGTCTATTACTGTAATGCAAACTGGCTCGATAAATATGACTAC<br>TGGGGCCAGGGGACCCAGGTCACCGTCTCCTCA | NG19 |
| 187 | CAGGTAAAGCTGGAGGAGTCTGGGGGAGGCTTGGTGGAGCCTGGGGGGTCTCTGAGACTCTCC<br>TGTGTGGCCTCTGGAAGCATCTCCAGTGCCAGATCCATGACCTGGTACCGCCAGGCTCACGGG<br>AAGCAGCGCGAGTTGGTCGCAGTTATTACTAGTGGCGGTAGCACAATGTATGCAGACTCCGTG<br>AAGGGCCGATTCACCATCTCCAGAGACAGCGCCAAGAACACGGTGTATCTACAAATGAACAGC<br>CTGAAACCTFAGGACACGGCCGTCTATTATTGTAATGCAGACTGGGGGGAAGTCGGGTTTGTG<br>AACTTAGGTCCCTGGGGCCAGGGGACCCAGGTCACCGTCTCCTCA | NG26 (G21-1) |
| 188 | GAGGTACAGCTGGTGGAATCTGGGGGAGGCTTGGTGCAGCCTGGGGGGTCTCTGAGACTCTCC<br>TGTGCAGCCTCTGGAAGCATCTTCGGTTTCAATGGCGTGGCCTGGTTCCGCCAGGCTCCAGGG<br>AAGCAGCGCGAGTTGGTCGCAGTTATTCGTAGTGGTGGTAACACGCTCTATGCAGACTCCGTG<br>AAGGGCCGATTCACCATCTCCAGAGACAACGCCAAGAACACGGTGTATCTGCAAATGAACAGC<br>CTGAAACCTGAGGACACGGCCGTCTATTACTGTAATGTAGATTACTCCCCGCCCGGTAGTCTG<br>GTTCCTGACTTAGGTCCCTGGGGCCAGGGGACCCAGGTCACCGTCTCCTCA | G18 |
| 189 | GAGGTACAGCTGGAGGAGTCTGGGGGAGGCTTGGTGCAGCCTGGGGGGTCTCTGAGACTCTCC<br>TGTGCAGCCTCTGGAAGCATCGCCAGTATCAATGCCATGGGCTGGTACCGCCAGGCTCCAGGG<br>AAGCAGCGCGAGTTGGTCGCAGCTATTACTAGAGGTGGTGGCACAAACTATGCAGACTCCGTG<br>AAGGGCCGATTCACCATCTCCAGAGACAACGCCAAGAACACGGTATATCTGCAAATGAACAGC<br>CTGAAACCGGAGGACACGGCCGTCTATTCATGTAATGGTTTGTGCTCAGACGATCGGTGTTAT<br>GGGGACTCCCTTTTTGCCCCCTGGGGCCCGGGGACCCAGGTCACCGTCTCCTCA | G16# |
| 190 | GAGGTACAGCTGGTGGAATCTGGGGGAGGATTGGTGCAGCCTGGGGGGTCTCTGAGACTGTCC<br>TGTCTAGTCTCTGGAAGGGGCGTCAGTCTCGATGCCGTGGGCTGGTCGCGCGTGGCTCCAGGG<br>AAGCAGCGCGACTTCGTCGCACGTATTGATAGTAGGGGTAGCGCATACTATGCAGACTCCGTA<br>GAGGGCCGATTCACCATCTCCAGAGACAACGCCAAGAACACGGTGTATCTGCAAGTGGACACG<br>CTGAAACCTGAGGACACGGCCGTCTATTATTGTTTTGCGTACTACGGGGCTCAAATATCTTTT<br>GGTCCGTGGGGCCAGGGGACCCAGGTCACCGTCTCTTCA | G24 |
| 191 | GATGTGCAGCTGCAGGCGTCTGGGGGAGGATTGGTGCAGCCTGGGGGGTCTCTGAGACTGTCC<br>TGTGTAGTCTCTGGAAGGGGCGTCAATCTCGATGCCATGGGCTGGTCGCGCGTGGCTCCAGGG<br>AAGCAGCGCGACTTCGTCGCACATATTGATGATAGGGGTACCGCATACTATGCAGACTTCGTA<br>AAGGGCCGATCCACCATCTCCAGAGACAACGCCAAGAACACGGTGTATCTGCAAGTGGACACG<br>CTGAAACCTGAGGACACGGCCGTCTATTATTGCTTTGCGTGGCAGGGTGCGGAAACATATTGG<br>GGCCTGGGGACCCGGGTCACCGTCTCCTCAGGATCCGAACCAAAACTGATCAACGAAGAACAT<br>CTGAACCATCACCATCACCATTATTGA | G19 |
| 192 | GAGGTACAGCTGGTGGAATCTGGGGGAGGCTTGGTGCAGGCTGGGGGGTCTCTGAGACTCTCC<br>TGTGTAGCCTCTGGAAGCATCTTCAGTGTCAATGCCGTGGCCTGGTACCGCCAGGCTCCAGGG<br>AAACAGCGCGAGTTGGTCGCATATATACGTCGTAGTGGTAGCACAAACTATGCAGACTCCGTG<br>AAGGGCCGATTCACCATCTCCAGAGACAATGCCAAGAACACGCTGTATCTGCAAATGAACAGC<br>CTGAAACCTGACGACACAGCCGTGTATTATTGTAATGCGGGGCGGACAGGGGATCGTTTTAAT<br>TTGGTGGCGTATTGGGGCCAGGGGACCCAGGTCACCGTCTCCTCA | G5-1 |
| 193 | GAGGTACAGCTGGTGGAATCTGGGGGAGGATTGGCGCAGGCTGGGGGCTCTCTGAGACTCTCC<br>TGTACAGCCTCTGGACGCACCTTCAGTACCTATTTCATGGCCTGGTTCCGCCAGCCTCCAGGG<br>AAAGAGCGTGAATACGTAGGCGGTATTAGGTGGAGTGATGGTGTTCCACACTATGCAGACTCC<br>GTGAAGGGCCGATTCACCATCTCCAGAGACAACGCCAAGAACACGGTGTATTTGCAAATGAAC<br>AGCCTGAAACCTGAGGACACGGCCGTCTATTACTGCAATGCAGATTACTCCCCGCCCGGCAGC<br>CGGTTCCCTGACTTAGGTCCCTGGGGCCAGGGGACCCAGGTCACCGTCTCCTCA | G26 |
| 194 | GAGGTGCAGCTGCAGGCGTCTGGGGGAGGCTTGGTGCAGCCTGGGGGGTCTCTGAGACTCTCC<br>TGTGTAGCCTCTGGAAGCATCTTCAGTATCAAAGCCATGGCCTGGTACCGCCAGGCTCCAGGG<br>AAGCAGCGCGAGTTGGTCGCATACATTCGTAGTGGTGGTACGACAAACTATGCAGACTCCGTG<br>AAGGGCCGATTCACCATCTCCAGAGACATCGCCAAGAACACGGTGTATCTGCAAATGAACAGC<br>CTGAAATCTGAGGACACGGCCGTTTATTTTTGTGCATCACGGGGTATTGCGGATGGATCTGCT<br>TTGGTTCCTACGGCCAGGGGACCCAGGTCACCGTCTCCTCA | G27 |
| 195 | GAGGTACAGCTGGTGGAATCTGGGGGAGGCTTGGTGCAGGCTGGGGCCTCCGTGAGACTCTCC<br>TGTGCAGCCTCTGGACGCGCCAACAGTTTGTATGCCATGGGCTGGTTCCGCCAGGCTCCAGGG<br>AAGCAGCGCGAGTTGGTCGCATACATTCGTAGTGGTGGTACGACAAACTATGCAGACTCCGTG<br>AAGGGCCGATTCACCATCTCCAGAGACATCGCCAAGAACACGGTGTATCTGCAAATGAACAGC<br>CTGAAACCTGAGGACACGGCCGTCTATTACTGCAATGCAGATTACTCCCCGCCCGGCAGCCGG<br>TTCCCTGACTTAGGTCCCTGGGGCCAGGGGACCCAGGTCACCGTCTCCTCA | G1-2 |
| 196 | GAGGTACAGCTGGTGGAATCTGGGGGAGGATTGGTGCAAATTGGGGACTCTGTGAGACTCTCC<br>TGTATAGCCTCTGGAGGCACCTTCAGAACTTATGCTATGGGTTGGTTCCGCCAGGCTCCAGGG | G28 |

| Sequence | Nucleotide acid sequence | Clone group |
|---|---|---|
| | GCTGAGCGTGAATTTGTAGCTGCCATTAGCCGGCGCGGTAATAAGACAGATTATGCAGAGTCC GTGAAGGGCCGATTCACAGTCTCCAGAGACAACGCCGAGAATACGGTGTATTTGCAAATGAAC AGCCTGAAACCTGATGACATGGGCGTTTATTACTGTGCAGCGTCGGCGCGTAATTTCATCGGC ACCCAGCCACTTGATTATGACTACTGGGGCCAGGGGACCCAGGTCACCGTCTCCTCA | |
| 197 | CAGGTAAAGCTGGAGGAGTCTGGGGGAGGAATGGTGCAGGCTGGGGGCTCTCTGAGACTCTCC TGTGTAGCCTCTGGACGCTCCTTCGTTGGCTATTTCATGGCCTGGTTCCGCCAGCCTCCAGGG AAAGAGCGTGAATACGTAGGCGGTATTAGGTGGAGTGATGGTGTTCCACACTATGCAGACTCC GTGAAGGGCCGATTCACCATCTCCAGAGACAACGCCAAGAACACGGTGTATTTGCAAATGAAC AGCCTGAAATCTGAGGACACGGCCGTTTATTTTTGTGCATCACGGGGTATTGCGGATGGATCT GACTTTGGTTCCTACGGCCAGGGGACCCAGGTCACCGTCTCCTCA | G29 |
| 198 | GAGGTACAGCTGGTGGAATCTGGGGGAGGCTTGGTGCAGCCTGGGGGGTCTCTGAGACTCTCC TGTGCAGCCTCTGGAAGCATCTTCAGTATCAATGCCATGGGCTGGTACCGCCAGGCTCCAGGG AAGCAGCGCGAATTGGTCGCAGCTATTACTAAAAGTAATAACATAAACTATGCAGACTCCGTG AAGGGCCGATTCACCATCTCCAGAGACAACGCCAAGAACACGGTGTATCTGCAAATGAACAGC CTGAAACCTGAGGACACGGCCGTCTATTATTGTAATGGATTCTTCACTTTGCCTGGGTACAGT AGTGAAGAATTTGGTCCCTGGGGCCTGGGGACCCAGGTCACCGTCTCCTCA | G2-1 |

The invention claimed is:

1. An anti-BCMA (B cell maturation antigen) single domain antibody, comprising framework regions and complementarity determining regions, wherein the complementarity determining regions comprise the amino acid sequences of CDR1, CDR2, and CDR3 in SEQ ID NO: 67.

2. The antibody of claim 1, wherein the single domain antibody comprises an amino acid sequence of SEQ ID NO:67 or is an amino acid sequence of SEQ ID NO: 67.

3. A chimeric antigen receptor, comprising the single domain antibody of claim 1.

4. The antibody of claim 1, wherein said single domain antibody is a humanized antibody.

5. The chimeric antigen receptor of claim 3, comprising more than one of the single domain antibody,
wherein the single domain antibodies are the same.

6. The chimeric antigen receptor of claim 3, comprising more than one of the single domain antibody,
wherein the single domain antibodies are different.

7. A method of treating diseases associated with abnormal BCMA (B cell maturation antigen) expression, the method comprising:
administering to a subject in need thereof an effective amount of a pharmaceutical composition comprising the single domain antibody of claim 1.

8. The method of claim 7, wherein said disease associated with abnormal BCMA expression is a multiple myeloma disease.

9. The method of claim 7, wherein the single domain antibody can be used to detect BCMA.

10. The method of claim 7, wherein said single domain antibody is able to block an interaction between BAFF (B cell-activating factor) and BCMA.

11. The method of claim 10, wherein said single domain antibody is linked to one or more of cytotoxicity agent(s), enzyme phase(s), radioisotope(s), fluorescent compound(s) or chemiluminescent compound(s).

* * * * *

UNITED STATES PATENT AND TRADEMARK OFFICE
CERTIFICATE OF CORRECTION

PATENT NO. : 12,227,581 B2
APPLICATION NO. : 17/270788
DATED : February 18, 2025
INVENTOR(S) : Zhang et al.

Page 1 of 1

It is certified that error appears in the above-identified patent and that said Letters Patent is hereby corrected as shown below:

On the Title Page

Item (71), "SHENZHEN PREGENE BIOPHARMA CO. LTD." should read -- SHENZHEN PREGENE BIOPHARMA CO., LTD. --

Signed and Sealed this
Twenty-fifth Day of March, 2025

Coke Morgan Stewart
*Acting Director of the United States Patent and Trademark Office*

SEQUENCE LISTING

<160> NUMBER OF SEQ ID NOS: 205

<210> SEQ ID NO 1
<211> LENGTH: 37
<212> TYPE: PRT
<213> ORGANISM: artificial sequence
<220> FEATURE:
<223> OTHER INFORMATION: amino acid sequence of G3's complementary
      determining region

<400> SEQUENCE: 1

Thr Tyr Phe Met Ala Gly Gly Ile Arg Trp Ser Asp Gly Val Pro His
1               5                   10                  15

Tyr Ala Asp Ser Val Lys Gly Cys Ala Ser Arg Gly Ile Ala Asp Gly
            20                  25                  30

Ser Asp Phe Gly Ser
        35

<210> SEQ ID NO 2
<211> LENGTH: 39
<212> TYPE: PRT
<213> ORGANISM: artificial sequence
<220> FEATURE:
<223> OTHER INFORMATION: amino acid sequence of G1's complementary
      determining region

<400> SEQUENCE: 2

Ile Lys Ala Met Ala Ala Tyr Ile Arg Ser Gly Gly Thr Thr Asn Tyr
1               5                   10                  15

Ala Asp Ser Val Lys Gly Cys Asn Ala Asp Tyr Ser Pro Pro Gly Ser
            20                  25                  30

Arg Phe Pro Asp Leu Gly Pro
        35

<210> SEQ ID NO 3
<211> LENGTH: 33
<212> TYPE: PRT
<213> ORGANISM: artificial sequence
<220> FEATURE:
<223> OTHER INFORMATION: amino acid sequence of NG7's complementary
      determining region

<400> SEQUENCE: 3

Ala Asn Thr Met Ala Ala Arg Ile Ser Thr Asp Gly Arg Thr Asn Tyr
1               5                   10                  15

Ala Asp Ser Val Lys Gly Cys Asn Ala Asn Trp Leu Ser Lys Phe Asp
            20                  25                  30

Tyr

<210> SEQ ID NO 4
<211> LENGTH: 36
<212> TYPE: PRT
<213> ORGANISM: artificial sequence
<220> FEATURE:
<223> OTHER INFORMATION: amino acid sequence of G5's complementary
      determining region

<400> SEQUENCE: 4

Val Asn Ala Val Ala Ala Tyr Ile Arg Arg Ser Gly Ser Thr Asn Tyr
1               5                   10                  15

Ala Asp Ser Val Lys Gly Cys Asn Ala Asp Phe Gly Ser Asp Tyr Val
            20                  25                  30

Val Leu Gly Ser
        35

<210> SEQ ID NO 5
<211> LENGTH: 37
<212> TYPE: PRT
<213> ORGANISM: artificial sequence
<220> FEATURE:
<223> OTHER INFORMATION: amino acid sequence of G9's complementary
      determining region

<400> SEQUENCE: 5

Ile Lys Ala Leu Ala Ala Tyr Ile Thr Ser Gly Gly Asn Thr Asn Tyr
1               5                   10                  15

Ala Asp Ser Val Arg Gly Cys Asn Ala Asp Phe Gly Glu Gly Thr Ile
            20                  25                  30

Ile Ser Leu Gly Pro
        35

<210> SEQ ID NO 6
<211> LENGTH: 37
<212> TYPE: PRT
<213> ORGANISM: artificial sequence
<220> FEATURE:
<223> OTHER INFORMATION: amino acid sequence of G7's complementary
      determining region

<400> SEQUENCE: 6

Ile Asn Ala Met Ala Ala Ala Leu Thr Ser Gly Gly Asn Thr His Tyr
1               5                   10                  15

Ala Asp Ser Val Lys Gly Cys Asn Ala Asp Phe Gly Thr Ala Gly Leu
            20                  25                  30

Val Val Leu Gly Pro
        35

<210> SEQ ID NO 7
<211> LENGTH: 35
<212> TYPE: PRT
<213> ORGANISM: artificial sequence
<220> FEATURE:
<223> OTHER INFORMATION: amino acid sequence of G6-2's complementary
      determining region

<400> SEQUENCE: 7

Ile Asn Ala Met Ala Ala Tyr Ile Arg Ser Asn Gly Arg Thr Asn Tyr
1               5                   10                  15

Ala Asp Ser Val Lys Gly Cys Asn Ala Asp Tyr Gly Pro Val Ser
            20                  25                  30

Ile Gly Pro
        35

<210> SEQ ID NO 8
<211> LENGTH: 36
<212> TYPE: PRT
<213> ORGANISM: artificial sequence
<220> FEATURE:
<223> OTHER INFORMATION: amino acid sequence of G10's complementary
      determining region

<400> SEQUENCE: 8

Ile Lys Ala Met Ala Ala Val Thr Ser Gly Gly Ser Thr His Tyr
1               5                   10                  15

Leu Asp Ser Val Lys Gly Cys Asn Ala Asp Phe Gly Thr Asp Tyr Val
            20                  25                  30

Asp Leu Gly Pro
        35

<210> SEQ ID NO 9
<211> LENGTH: 39
<212> TYPE: PRT
<213> ORGANISM: artificial sequence
<220> FEATURE:
<223> OTHER INFORMATION: amino acid sequence of G2's complementary
      determining region

<400> SEQUENCE: 9

Ile Asn Ala Met Gly Ala Ala Ile Thr Lys Ser Asn Asn Ile Asn Tyr
1               5                   10                  15

Ala Asp Ser Val Lys Gly Cys Asn Gly Phe Phe Ala Leu Pro Gly Tyr
            20                  25                  30

Ser Ser Glu Glu Phe Gly Pro
        35

<210> SEQ ID NO 10
<211> LENGTH: 37
<212> TYPE: PRT
<213> ORGANISM: artificial sequence
<220> FEATURE:
<223> OTHER INFORMATION: amino acid sequence of G8's complementary
      determining region

<400> SEQUENCE: 10

Met Asn Arg Met Gly Ala Asp Ile Arg Asp Gly Gly Ser Thr Ile Tyr
1               5                   10                  15

Ser Asp Ser Val Lys Gly Cys Asn Ala Gly Arg Thr Gly Asp Arg Phe
            20                  25                  30

Asn Leu Val Ala Tyr
        35

<210> SEQ ID NO 11
<211> LENGTH: 41
<212> TYPE: PRT
<213> ORGANISM: artificial sequence
<220> FEATURE:
<223> OTHER INFORMATION: amino acid sequence of G17's complementary determining region

<400> SEQUENCE: 11

Gly Tyr Ala Met Ala Ala Ile Ser Ser Ser Asn Ser Ala Pro
1               5                   10                  15

Tyr Tyr Ala Asn Ser Val Lys Gly Cys Ala Ala Arg Tyr Gly Thr Lys
            20                  25                  30

Arg Tyr Val Ala Arg Glu Tyr Asp Ser
        35                  40

<210> SEQ ID NO 12
<211> LENGTH: 32
<212> TYPE: PRT
<213> ORGANISM: artificial sequence
<220> FEATURE:
<223> OTHER INFORMATION: amino acid sequence of G25's complementary
      determining region

<400> SEQUENCE: 12

Ile Asn Gly Met Gly Ala Arg Ile Asp Ser Arg Gly Ser Ala Tyr Tyr
1               5                   10                  15

Ala Asp Phe Val Glu Gly Cys Phe Ala Trp Gln Gly Ala Glu Thr Tyr
            20                  25                  30

<210> SEQ ID NO 13
<211> LENGTH: 35
<212> TYPE: PRT
<213> ORGANISM: artificial sequence
<220> FEATURE:
<223> OTHER INFORMATION: amino acid sequence of NG1's complementary
      determining region

<400> SEQUENCE: 13

Thr Tyr Ala Met Ala Ala Tyr Ile Thr Asn Gly Gly Ser Thr Asp Tyr
1               5                   10                  15

Ala Ala Ser Val Lys Gly Cys Asn Gly Ala Thr Arg Gly Ala Gln Leu
            20                  25                  30

Val Phe Asp
        35

<210> SEQ ID NO 14
<211> LENGTH: 41
<212> TYPE: PRT
<213> ORGANISM: artificial sequence
<220> FEATURE:
<223> OTHER INFORMATION: amino acid sequence of NG20's complementary
      determining region

<400> SEQUENCE: 14

Asn Tyr Ala Met Ala Ala Ile Ser Val Ser Ala Asn Ser Ala Pro
1               5                   10                  15

Tyr Tyr Ala Asn Ser Val Lys Gly Cys Ala Ala Arg Tyr Gly Thr Lys
            20                  25                  30

Arg Tyr Val Ala Arg Glu Tyr Asp Ser
        35                  40

<210> SEQ ID NO 15
<211> LENGTH: 32
<212> TYPE: PRT
<213> ORGANISM: artificial sequence
<220> FEATURE:
<223> OTHER INFORMATION: amino acid sequence of NG21's complementary
      determining region

```
<400> SEQUENCE: 15

Leu Asn Ala Met Gly Ala Arg Ile Ala Ala Asp Gly Ser Thr His Tyr
1               5                   10                  15

Ala Asp Ser Val Glu Gly Cys Phe Ala Trp Leu Gly Thr Asp Thr Tyr
                20                  25                  30

<210> SEQ ID NO 16
<211> LENGTH: 31
<212> TYPE: PRT
<213> ORGANISM: artificial sequence
<220> FEATURE:
<223> OTHER INFORMATION: amino acid sequence of G14's complementary
      determining region

<400> SEQUENCE: 16

Asn Asn Ala Met Gly Ala Arg Ile Asp Ser Gly Gly Ile Thr Arg Tyr
1               5                   10                  15

Ala Asp Ser Leu Lys Gly Cys Phe Ala His Val Gly Thr Ile
                20                  25                  30

<210> SEQ ID NO 17
<211> LENGTH: 41
<212> TYPE: PRT
<213> ORGANISM: artificial sequence
<220> FEATURE:
<223> OTHER INFORMATION: amino acid sequence of NGS1's complementary
      determining region

<400> SEQUENCE: 17

Ile Asn Ser Met Gly Ala Ser Ile Thr Gly Gly Gly Ser Ser Arg Tyr
1               5                   10                  15

Ala Asp Ser Val Lys Gly Cys Asn Thr Ile Pro Pro Ala Arg Thr Gln
                20                  25                  30

Ser Asp His Gly Glu Trp Tyr Asp Tyr
            35                  40

<210> SEQ ID NO 18
<211> LENGTH: 34
<212> TYPE: PRT
<213> ORGANISM: artificial sequence
<220> FEATURE:
<223> OTHER INFORMATION: amino acid sequence of G12's complementary
      determining region

<400> SEQUENCE: 18

Ile Asn Met Ser Ala Thr Thr Arg His Asp Ser Thr His Tyr Ser Asp
1               5                   10                  15

Ser Val Lys Gly Cys Ser Gly Phe Phe Leu Asp Gly Ser Thr Trp His
                20                  25                  30

Pro Tyr

<210> SEQ ID NO 19
<211> LENGTH: 39
<212> TYPE: PRT
<213> ORGANISM: artificial sequence
<220> FEATURE:
<223> OTHER INFORMATION: amino acid sequence of G6's complementary
      determining region

<400> SEQUENCE: 19

Ile Asn Ala Met Ala Ala Tyr Ile Arg Ser Asn Gly Ser Thr Asn Tyr
1               5                   10                  15

Ala Asp Ser Val Lys Gly Cys Asn Gly Phe Phe Thr Leu Pro Gly Tyr
```

Ser Ser Glu Glu Phe Gly Pro
        35

<210> SEQ ID NO 20
<211> LENGTH: 40
<212> TYPE: PRT
<213> ORGANISM: artificial sequence
<220> FEATURE:
<223> OTHER INFORMATION: amino acid sequence of G22#'s complementary
      determining region

<400> SEQUENCE: 20

Ile Asn Ala Met Gly Ala Gly Ile Thr Lys Gly Gly Arg Thr Asn Tyr
1               5                   10                  15

Ala Asp Ser Val Lys Gly Cys Asn Gly Leu Cys Ser Gly Arg Glu Cys
            20                  25                  30

Tyr Gly Asp Ser Leu Phe Ala Ala
        35                  40

<210> SEQ ID NO 21
<211> LENGTH: 36
<212> TYPE: PRT
<213> ORGANISM: artificial sequence
<220> FEATURE:
<223> OTHER INFORMATION: amino acid sequence of G6-1's complementary
      determining region

<400> SEQUENCE: 21

Ile Asn Ala Met Ala Ala Tyr Ile Arg Ser Asn Gly Arg Thr Asn Tyr
1               5                   10                  15

Ala Asp Ser Val Lys Gly Cys Ser Gly Phe Phe Leu Asp Gly Ser Thr
            20                  25                  30

Trp His Pro Tyr
        35

<210> SEQ ID NO 22
<211> LENGTH: 40
<212> TYPE: PRT
<213> ORGANISM: artificial sequence
<220> FEATURE:
<223> OTHER INFORMATION: amino acid sequence of G13#'s complementary
      determining region

<400> SEQUENCE: 22

Asp Tyr Ala Ile Gly Ser Cys Ile Ser Ser Asp Gly Ser Thr His
1               5                   10                  15

Tyr Ala Asp Ser Val Lys Gly Cys Ala Thr Pro Trp Val Thr Tyr Cys
            20                  25                  30

Pro Glu Asn Leu Leu Phe Ser Tyr
        35                  40

<210> SEQ ID NO 23
<211> LENGTH: 40
<212> TYPE: PRT
<213> ORGANISM: artificial sequence
<220> FEATURE:
<223> OTHER INFORMATION: amino acid sequence of G13-2#'s complementary
      determining region

<400> SEQUENCE: 23

Asp Tyr Ala Ile Gly Ser Cys Ile Thr Ser Ser Asp Gly Ser Thr Tyr
1               5                   10                  15

Tyr Ala Asp Ser Val Lys Gly Cys Ala Thr Pro Trp Val Thr Tyr Cys
            20                  25                  30

Pro Glu Asn Leu Leu Phe Ser Tyr
        35                  40

<210> SEQ ID NO 24
<211> LENGTH: 37
<212> TYPE: PRT
<213> ORGANISM: artificial sequence
<220> FEATURE:
<223> OTHER INFORMATION: amino acid sequence of G31's complementary
      determining region

<400> SEQUENCE: 24

Ile Lys Ala Met Gly Ala Ala Ile Thr Ser Gly Gly Ser Thr Asn Tyr
1               5                   10                  15

Ala Asp Ser Val Lys Gly Cys Asn Gly Phe Phe Glu Tyr Arg Gly Leu
            20                  25                  30

Glu Gln Leu Gly Pro
        35

<210> SEQ ID NO 25
<211> LENGTH: 37
<212> TYPE: PRT
<213> ORGANISM: artificial sequence
<220> FEATURE:
<223> OTHER INFORMATION: amino acid sequence of G4's complementary
      determining region

<400> SEQUENCE: 25

Ile Arg Ala Met Thr Ala Val Leu Thr Ser Ala Gly Lys Pro Met Tyr
1               5                   10                  15

Ala Asp Ser Val Lys Gly Cys Asn Ala Asp Phe Gly Thr Pro Gly Ser
            20                  25                  30

Val Val Leu Gly Pro
        35

<210> SEQ ID NO 26
<211> LENGTH: 39
<212> TYPE: PRT
<213> ORGANISM: artificial sequence
<220> FEATURE:
<223> OTHER INFORMATION: amino acid sequence of NG2's complementary
      determining region

<400> SEQUENCE: 26

Ile Glu Ala Met Gly Ala Ala Ile Thr Ser Gly Asp Ser Thr Asn Tyr
1               5                   10                  15

Ala Asp Phe Val Lys Gly Cys Asn Ala Leu Met Val Val Arg Ala Gly
            20                  25                  30

Ser Asn Pro Glu Ile Gly Pro
        35

<210> SEQ ID NO 27
<211> LENGTH: 40
<212> TYPE: PRT
<213> ORGANISM: artificial sequence
<220> FEATURE:
<223> OTHER INFORMATION: amino acid sequence of G13-3#'s complementary
      determining region

<400> SEQUENCE: 27

Asp Tyr Ala Ile Gly Ser Cys Ile Ser Ser Ser Asp Gly Ser Thr Tyr
1               5                   10                  15

Tyr Ala Asp Ser Val Lys Gly Cys Ala Thr Pro Trp Val Thr Tyr Cys
            20                  25                  30

Pro Glu Asn Leu Leu Phe Ser Tyr
            35                  40

<210> SEQ ID NO 28
<211> LENGTH: 32
<212> TYPE: PRT
<213> ORGANISM: artificial sequence
<220> FEATURE:
<223> OTHER INFORMATION: amino acid sequence of G20's complementary
      determining region

<400> SEQUENCE: 28

Leu Asp Ala Val Gly Ala Arg Ile Asp Arg Arg Gly Ser Thr Tyr Tyr
1               5                   10                  15

Ala Val Ser Val Glu Gly Cys Phe Ala Trp Gln Gly Ala Glu Thr His
            20                  25                  30

<210> SEQ ID NO 29
<211> LENGTH: 32
<212> TYPE: PRT
<213> ORGANISM: artificial sequence
<220> FEATURE:
<223> OTHER INFORMATION: amino acid sequence of NG3's complementary
      determining region

<400> SEQUENCE: 29

Phe Asn Asp Met Gly Ala Ala Ile Thr Ser Ser Arg Asn Thr Leu Tyr
1               5                   10                  15

Val Asp Ser Val Lys Gly Cys Asn Pro Tyr Pro Ser Pro Asn Asn Tyr
            20                  25                  30

<210> SEQ ID NO 30
<211> LENGTH: 33
<212> TYPE: PRT
<213> ORGANISM: artificial sequence
<220> FEATURE:
<223> OTHER INFORMATION: amino acid sequence of NG4's complementary
      determining region

<400> SEQUENCE: 30

Ile Asn Ala Met Gly Ala Ala Ile Thr Arg Ser Gly Lys Thr Asn Tyr
1               5                   10                  15

Ala Asp Ser Val Lys Gly Cys Asn Gly Phe Tyr Gly Ser Glu Phe Gly
            20                  25                  30

Pro

<210> SEQ ID NO 31
<211> LENGTH: 41
<212> TYPE: PRT
<213> ORGANISM: artificial sequence
<220> FEATURE:
<223> OTHER INFORMATION: amino acid sequence of NG5's complementary
      determining region

<400> SEQUENCE: 31

Arg Tyr Ala Val Gly Ala Ser Ile Thr Trp Ser Gly Asp Tyr Thr Tyr
1               5                   10                  15

Tyr Lys Asp Ser Val Lys Gly Cys Ala Ala Asp Lys Ser Ser Phe Arg
            20                  25                  30

Leu Arg Gly Pro Gly Leu Tyr Asp Tyr
            35                  40

<210> SEQ ID NO 32
<211> LENGTH: 40
<212> TYPE: PRT
<213> ORGANISM: artificial sequence
<220> FEATURE:
<223> OTHER INFORMATION: amino acid sequence of ++'s complementary
      determining region

<400> SEQUENCE: 32

Tyr Tyr Ala Ile Gly Ser Cys Ile Ser Ser Arg Asp Gly Thr Thr His
1               5                   10                  15

Tyr Ala Asp Ser Val Lys Gly Cys Ala Thr Pro Trp Val Thr Tyr Cys
            20                  25                  30

Pro Glu Asn Leu Leu Phe Ser Tyr
        35                  40

<210> SEQ ID NO 33
<211> LENGTH: 42
<212> TYPE: PRT
<213> ORGANISM: artificial sequence
<220> FEATURE:
<223> OTHER INFORMATION: amino acid sequence of NG8's complementary
      determining region

<400> SEQUENCE: 33

Tyr Tyr Ala Ile Gly Ser Ala Ile Ser Asn Ile Asp Asp Asp Thr Tyr
1               5                   10                  15

Tyr Glu Asp Ser Val Lys Gly Cys Ala Ala Asp Lys Asp Val Val Val
            20                  25                  30

Val Arg Thr Gly Leu Ser Glu Ser Asp Tyr
        35                  40

<210> SEQ ID NO 34
<211> LENGTH: 37
<212> TYPE: PRT
<213> ORGANISM: artificial sequence
<220> FEATURE:
<223> OTHER INFORMATION: amino acid sequence of NG9's complementary
      determining region

<400> SEQUENCE: 34

Ile Asn Ala Met Ala Ala Val Ile Thr Ser Gly Gly Arg Thr Met Tyr
1               5                   10                  15

Ala Glu Ser Val Lys Gly Cys Asn Gly Asp Trp Gly Ser Glu Gly Arg
            20                  25                  30

Val Asp Leu Gly Pro
        35

<210> SEQ ID NO 35
<211> LENGTH: 46
<212> TYPE: PRT
<213> ORGANISM: artificial sequence
<220> FEATURE:
<223> OTHER INFORMATION: amino acid sequence of NG10's complementary
      determining region

<400> SEQUENCE: 35

Ile Gly Asp Met Glu Ala Ser Ile Ser Ala Gly Pro Glu Met Arg Ser
1               5                   10                  15

Ala Gly Thr Pro Thr Tyr Ala Lys Ser Val Glu Gly Cys Asn Ala Asp
            20                  25                  30

Val Leu Thr Tyr Tyr Asn Gly Arg Tyr Ser Arg Asp Val Tyr

```
                     35                  40                  45

<210> SEQ ID NO 36
<211> LENGTH: 35
<212> TYPE: PRT
<213> ORGANISM: artificial sequence
<220> FEATURE:
<223> OTHER INFORMATION: amino acid sequence of G12-1's complementary
      determining region

<400> SEQUENCE: 36

Ile Asn Met Ser Ala Thr Ile Thr Arg His Asp Ser Thr His Tyr Ser
1               5                  10                  15

Asp Ser Val Lys Gly Cys Ser Gly Phe Phe Leu Asp Gly Ser Thr Trp
            20                  25                  30

Arg Pro Tyr
        35

<210> SEQ ID NO 37
<211> LENGTH: 41
<212> TYPE: PRT
<213> ORGANISM: artificial sequence
<220> FEATURE:
<223> OTHER INFORMATION: amino acid sequence of complementary
      determining region

<400> SEQUENCE: 37

Gly Tyr Ala Val Ala Ala Ala Ile Ser Ser Ser Asp Asn Ser Ser Pro
1               5                  10                  15

Tyr Tyr Ala Asn Val Val Lys Gly Cys Ala Ala Arg Tyr Gly Thr Lys
            20                  25                  30

Arg Tyr Val Ala Arg Glu Tyr Asp Ser
        35                  40

<210> SEQ ID NO 38
<211> LENGTH: 39
<212> TYPE: PRT
<213> ORGANISM: artificial sequence
<220> FEATURE:
<223> OTHER INFORMATION: amino acid sequence of NG11's complementary
      determining region

<400> SEQUENCE: 38

Ile Asn Ala Met Ala Ala Tyr Ile Arg Ser Ser Gly Thr Thr Met Tyr
1               5                  10                  15

Ala Asp Ser Val Lys Gly Cys Asn Gly Asp Tyr Ser Pro Pro Gly Ser
            20                  25                  30

Thr Tyr Pro Asp Leu Gly Pro
        35

<210> SEQ ID NO 39
<211> LENGTH: 47
<212> TYPE: PRT
<213> ORGANISM: artificial sequence
<220> FEATURE:
<223> OTHER INFORMATION: amino acid sequence of G15(bi)'s complementary
      determining region

<400> SEQUENCE: 39

Asp Tyr Ala Ile Gly Ser Cys Ile Thr Ser Ser Asp Gly Ser Thr Tyr
1               5                  10                  15

Tyr Ala Asp Ser Val Lys Gly Cys Ala Thr Pro Trp Val Asn Tyr Cys
            20                  25                  30
```

Pro Glu Asn Leu Leu Phe Ser Tyr Phe Ser Thr Tyr Phe Met Ala
        35                  40                  45

<210> SEQ ID NO 40
<211> LENGTH: 33
<212> TYPE: PRT
<213> ORGANISM: artificial sequence
<220> FEATURE:
<223> OTHER INFORMATION: amino acid sequence of G11's complementary
      determining region

<400> SEQUENCE: 40

Ala Ala Ile Arg Trp Ser Asp Gly Val Pro His Tyr Thr Asp Ser Val
1               5                   10                  15

Lys Gly Cys Ala Ser Arg Gly Ile Ala Asp Gly Ser Asp Phe Gly Ser
            20                  25                  30

Tyr

<210> SEQ ID NO 41
<211> LENGTH: 32
<212> TYPE: PRT
<213> ORGANISM: artificial sequence
<220> FEATURE:
<223> OTHER INFORMATION: amino acid sequence of NG12's complementary
      determining region

<400> SEQUENCE: 41

Ile Asp Ala Met Gly Ala Arg Leu Gly Ser Asn Gly Phe Thr Gln Tyr
1               5                   10                  15

Asp Ile Ser Val Glu Gly Cys Phe Ala Trp Leu Gly Gln Asp Thr Val
            20                  25                  30

<210> SEQ ID NO 42
<211> LENGTH: 41
<212> TYPE: PRT
<213> ORGANISM: artificial sequence
<220> FEATURE:
<223> OTHER INFORMATION: amino acid sequence of NG14's complementary
      determining region

<400> SEQUENCE: 42

Asn Tyr Ala Met Gly Ala Ser Val Thr Arg Ser Gly Asp Asn Thr Tyr
1               5                   10                  15

Tyr Lys Asp Ser Ala Lys Gly Cys Ala Ala Asp Lys Ser Ser Phe Arg
            20                  25                  30

Leu Arg Gly Pro Gly Val Tyr Asp Tyr
            35                  40

<210> SEQ ID NO 43
<211> LENGTH: 43
<212> TYPE: PRT
<213> ORGANISM: artificial sequence
<220> FEATURE:
<223> OTHER INFORMATION: amino acid sequence of NG13's complementary
      determining region

<400> SEQUENCE: 43

Val Met Leu Met Gly Ala Ser Ile Thr Ser Ala Asp Tyr Thr Thr Tyr
1               5                   10                  15

Ala Glu Ser Val Glu Gly Cys Lys Val Ile Ala Ala Thr Val Trp Gly
            20                  25                  30

Gln Glu Thr Gln Val Arg Gln Gly Leu Thr Phe
            35                  40

```
<210> SEQ ID NO 44
<211> LENGTH: 37
<212> TYPE: PRT
<213> ORGANISM: artificial sequence
<220> FEATURE:
<223> OTHER INFORMATION: amino acid sequence of G21's complementary
      determining region

<400> SEQUENCE: 44

Ala Arg Ser Met Thr Ala Val Ile Met Gly Gly Gly Ser Thr Met Tyr
1               5                  10                  15

Ala Asp Ser Val Lys Gly Cys Asn Ala Asp Trp Gly Glu Val Gly Phe
            20                  25                  30

Pro Asn Leu Gly Pro
        35

<210> SEQ ID NO 45
<211> LENGTH: 41
<212> TYPE: PRT
<213> ORGANISM: artificial sequence
<220> FEATURE:
<223> OTHER INFORMATION: amino acid sequence of NG23's complementary
      determining region

<400> SEQUENCE: 45

Thr Tyr Ala Ile Gly Ala Ala Ile Ser Arg Arg Gly Asn Lys Thr Asp
1               5                  10                  15

Tyr Ala Glu Ser Val Lys Gly Cys Ala Ala Ser Ala Arg Asn Phe Ile
            20                  25                  30

Gly Thr Gln Pro Leu Asp Tyr Asp Tyr
        35                  40

<210> SEQ ID NO 46
<211> LENGTH: 39
<212> TYPE: PRT
<213> ORGANISM: artificial sequence
<220> FEATURE:
<223> OTHER INFORMATION: amino acid sequence of NG15's complementary
      determining region

<400> SEQUENCE: 46

Asn Tyr Ala Leu Gly Ala Ala Ile Asp Trp Arg His Ser Ser Tyr Tyr
1               5                  10                  15

Ala Asp Ser Val Lys Gly Cys Ala Ala Ser Ser Leu Phe Pro Ser Ser
            20                  25                  30

Ala Pro Arg Gln Tyr Asp Tyr
        35

<210> SEQ ID NO 47
<211> LENGTH: 40
<212> TYPE: PRT
<213> ORGANISM: artificial sequence
<220> FEATURE:
<223> OTHER INFORMATION: amino acid sequence of NG16's complementary
      determining region

<400> SEQUENCE: 47

Asn Tyr Ala Met Gly Ala Ala Ile Val Gly Ser Gly Asp Ser Thr Arg
1               5                  10                  15

Tyr Ala Asp Ser Val Lys Gly Cys Ala Ser Ser Ser Asp Pro Arg Val
            20                  25                  30

Tyr Ile Ala Ser Thr Leu Asp Tyr
        35                  40
```

```
<210> SEQ ID NO 48
<211> LENGTH: 36
<212> TYPE: PRT
<213> ORGANISM: artificial sequence
<220> FEATURE:
<223> OTHER INFORMATION: amino acid sequence of G23's complementary
      determining region

<400> SEQUENCE: 48

Met Phe Ile Met Gly Ala Ala Ile Ser Arg Asn Ser Asn Leu Thr Tyr
1               5                   10                  15

Tyr Phe Gln Ser Val Lys Gly Cys Asn Ala Asp Tyr Gly Pro Pro Val
            20                  25                  30

Ser Ile Gly Pro
        35

<210> SEQ ID NO 49
<211> LENGTH: 39
<212> TYPE: PRT
<213> ORGANISM: artificial sequence
<220> FEATURE:
<223> OTHER INFORMATION: amino acid sequence of NG17's complementary
      determining region

<400> SEQUENCE: 49

Ile Lys Ala Met Gly Ala Gly Ile Val Ser Ser Gly Asn Thr Asn Tyr
1               5                   10                  15

Ala Asp Phe Val Lys Gly Cys Asn Ala Leu Val Val Val Thr Ser Ala
            20                  25                  30

Ser Gly Pro Glu Leu Ala Ser
        35

<210> SEQ ID NO 50
<211> LENGTH: 39
<212> TYPE: PRT
<213> ORGANISM: artificial sequence
<220> FEATURE:
<223> OTHER INFORMATION: amino acid sequence of G1-3's complementary
      determining region

<400> SEQUENCE: 50

Thr Tyr Phe Met Ala Ala Tyr Ile Arg Ser Gly Gly Thr Thr Asn Tyr
1               5                   10                  15

Ala Asp Ser Val Lys Gly Cys Asn Ala Asp Tyr Ser Pro Pro Gly Ser
            20                  25                  30

Arg Phe Pro Asp Leu Gly Pro
        35

<210> SEQ ID NO 51
<211> LENGTH: 38
<212> TYPE: PRT
<213> ORGANISM: artificial sequence
<220> FEATURE:
<223> OTHER INFORMATION: amino acid sequence of NG18's complementary
      determining region

<400> SEQUENCE: 51

Asn Tyr Ala Ile Ala Ser Ser Thr Gly Ser Asp Gly Asn Leu Tyr Thr
1               5                   10                  15

Pro Ser Val Arg Gly Cys Val Ala Gly Lys Arg Pro Val Ile Thr Thr
            20                  25                  30

Trp Ile Ala Leu Asp Ala
```

<210> SEQ ID NO 52
<211> LENGTH: 32
<212> TYPE: PRT
<213> ORGANISM: artificial sequence
<220> FEATURE:
<223> OTHER INFORMATION: amino acid sequence of NG24's complementary
      determining region

<400> SEQUENCE: 52

Ile Asp Ser Met Arg Ala His Ile Thr Ser Thr Gly Arg Thr Asn Tyr
1               5                   10                  15

Ala Asp Ala Val Lys Gly Cys Asn Met Val Thr Thr Pro Tyr Met His
            20                  25                  30

<210> SEQ ID NO 53
<211> LENGTH: 32
<212> TYPE: PRT
<213> ORGANISM: artificial sequence
<220> FEATURE:
<223> OTHER INFORMATION: amino acid sequence of NG25's complementary
      determining region

<400> SEQUENCE: 53

Glu Asn Ala Met Gly Ala Ala Ile Thr Ser Ser Arg Ser Thr Leu Tyr
1               5                   10                  15

Ile Asp Ser Val Lys Gly Cys Asn Pro Tyr Pro Ser Pro Asn Ser Tyr
            20                  25                  30

<210> SEQ ID NO 54
<211> LENGTH: 33
<212> TYPE: PRT
<213> ORGANISM: artificial sequence
<220> FEATURE:
<223> OTHER INFORMATION: amino acid sequence of NG19's complementary
      determining region

<400> SEQUENCE: 54

Ala Asn Lys Met Gly Ala Arg Ile Ser Thr Asp Gly Arg Thr Asn Tyr
1               5                   10                  15

Ala Asp Ser Val Lys Gly Cys Asn Ala Asn Trp Leu Asp Lys Tyr Asp
            20                  25                  30

Tyr

<210> SEQ ID NO 55
<211> LENGTH: 37
<212> TYPE: PRT
<213> ORGANISM: artificial sequence
<220> FEATURE:
<223> OTHER INFORMATION: amino acid sequence of NG26(G21-1)'s
      complementary determining region

<400> SEQUENCE: 55

Ala Arg Ser Met Thr Ala Val Ile Thr Ser Gly Gly Ser Thr Met Tyr
1               5                   10                  15

Ala Asp Ser Val Lys Gly Cys Asn Ala Asp Trp Gly Glu Val Gly Phe
            20                  25                  30

Val Asn Leu Gly Pro
            35

<210> SEQ ID NO 56
<211> LENGTH: 39
<212> TYPE: PRT

```
<213> ORGANISM: artificial sequence
<220> FEATURE:
<223> OTHER INFORMATION: amino acid sequence of G18's complementary
      determining region

<400> SEQUENCE: 56

Phe Asn Gly Val Ala Ala Val Ile Arg Ser Gly Gly Asn Thr Leu Tyr
1               5                   10                  15

Ala Asp Ser Val Lys Gly Cys Asn Val Asp Tyr Ser Pro Pro Gly Ser
                20                  25                  30

Leu Val Pro Asp Leu Gly Pro
            35

<210> SEQ ID NO 57
<211> LENGTH: 40
<212> TYPE: PRT
<213> ORGANISM: artificial sequence
<220> FEATURE:
<223> OTHER INFORMATION: amino acid sequence of G16's complementary
      determining region

<400> SEQUENCE: 57

Ile Asn Ala Met Gly Ala Ala Ile Thr Arg Gly Gly Ser Thr Asn Tyr
1               5                   10                  15

Ala Asp Ser Val Lys Gly Cys Asn Gly Leu Cys Ser Asp Asp Arg Cys
                20                  25                  30

Tyr Gly Asp Ser Leu Phe Ala Pro
            35                  40

<210> SEQ ID NO 58
<211> LENGTH: 35
<212> TYPE: PRT
<213> ORGANISM: artificial sequence
<220> FEATURE:
<223> OTHER INFORMATION: amino acid sequence of G24's complementary
      determining region

<400> SEQUENCE: 58

Leu Asp Ala Val Gly Ala Arg Ile Asp Ser Arg Gly Ser Ala Tyr Tyr
1               5                   10                  15

Ala Asp Ser Val Glu Gly Cys Phe Ala Tyr Tyr Gly Ala Gln Ile Ser
                20                  25                  30

Phe Gly Pro
        35

<210> SEQ ID NO 59
<211> LENGTH: 33
<212> TYPE: PRT
<213> ORGANISM: artificial sequence
<220> FEATURE:
<223> OTHER INFORMATION: amino acid sequence of G19's complementary
      determining region

<400> SEQUENCE: 59

Leu Asp Ala Met Gly Ala His Ile Asp Asp Arg Gly Thr Ala Tyr
1               5                   10                  15

Tyr Ala Asp Phe Val Lys Gly Cys Phe Ala Trp Gln Gly Ala Glu Thr
                20                  25                  30

Tyr

<210> SEQ ID NO 60
<211> LENGTH: 37
<212> TYPE: PRT
```

<213> ORGANISM: artificial sequence
<220> FEATURE:
<223> OTHER INFORMATION: amino acid sequence of G5-1's complementary
      determining region

<400> SEQUENCE: 60

Val Asn Ala Val Ala Ala Tyr Ile Arg Arg Ser Gly Ser Thr Asn Tyr
1               5                   10                  15

Ala Asp Ser Val Lys Gly Cys Asn Ala Gly Arg Thr Gly Asp Arg Phe
            20                  25                  30

Asn Leu Val Ala Tyr
            35

<210> SEQ ID NO 61
<211> LENGTH: 40
<212> TYPE: PRT
<213> ORGANISM: artificial sequence
<220> FEATURE:
<223> OTHER INFORMATION: amino acid sequence of G26's complementary
      determining region

<400> SEQUENCE: 61

Thr Tyr Phe Met Ala Gly Gly Ile Arg Trp Ser Asp Gly Val Pro His
1               5                   10                  15

Tyr Ala Asp Ser Val Lys Gly Cys Asn Ala Asp Tyr Ser Pro Pro Gly
            20                  25                  30

Ser Arg Phe Pro Asp Leu Gly Pro
            35                  40

<210> SEQ ID NO 62
<211> LENGTH: 35
<212> TYPE: PRT
<213> ORGANISM: artificial sequence
<220> FEATURE:
<223> OTHER INFORMATION: amino acid sequence of G27's complementary
      determining region

<400> SEQUENCE: 62

Ile Lys Ala Met Ala Ala Tyr Ile Arg Ser Gly Gly Thr Asn Tyr Ala
1               5                   10                  15

Asp Ser Val Lys Gly Cys Ala Ser Arg Gly Ile Ala Asp Gly Ser Asp
            20                  25                  30

Phe Gly Ser
        35

<210> SEQ ID NO 63
<211> LENGTH: 39
<212> TYPE: PRT
<213> ORGANISM: artificial sequence
<220> FEATURE:
<223> OTHER INFORMATION: amino acid sequence of G1-2's complementary
      determining region

<400> SEQUENCE: 63

Leu Tyr Ala Met Gly Ala Tyr Ile Arg Ser Gly Gly Thr Thr Asn Tyr
1               5                   10                  15

Ala Asp Ser Val Lys Gly Cys Asn Ala Asp Tyr Ser Pro Pro Gly Ser
            20                  25                  30

Arg Phe Pro Asp Leu Gly Pro
            35

<210> SEQ ID NO 64
<211> LENGTH: 41

```
<212> TYPE: PRT
<213> ORGANISM: artificial sequence
<220> FEATURE:
<223> OTHER INFORMATION: amino acid sequence of G28's complementary
      determining region

<400> SEQUENCE: 64

Thr Tyr Ala Met Gly Ala Ala Ile Ser Arg Arg Gly Asn Lys Thr Asp
1               5                   10                  15

Tyr Ala Glu Ser Val Lys Gly Cys Ala Ala Ser Ala Arg Asn Phe Ile
            20                  25                  30

Gly Thr Gln Pro Leu Asp Tyr Asp Tyr
        35                  40

<210> SEQ ID NO 65
<211> LENGTH: 36
<212> TYPE: PRT
<213> ORGANISM: artificial sequence
<220> FEATURE:
<223> OTHER INFORMATION: amino acid sequence of G29's complementary
      determining region

<400> SEQUENCE: 65

Gly Tyr Phe Met Ala Gly Gly Ile Arg Trp Ser Asp Gly Val Pro His
1               5                   10                  15

Tyr Ala Asp Ser Val Lys Cys Ala Ser Arg Gly Ile Ala Asp Gly Ser
            20                  25                  30

Asp Phe Gly Ser
        35

<210> SEQ ID NO 66
<211> LENGTH: 39
<212> TYPE: PRT
<213> ORGANISM: artificial sequence
<220> FEATURE:
<223> OTHER INFORMATION: amino acid sequence of G2-1's complementary
      determining region

<400> SEQUENCE: 66

Ile Asn Ala Met Gly Ala Ala Ile Thr Lys Ser Asn Asn Ile Asn Tyr
1               5                   10                  15

Ala Asp Ser Asx Lys Gly Cys Asn Gly Phe Phe Thr Leu Pro Gly Tyr
            20                  25                  30

Ser Ser Glu Glu Phe Gly Pro
        35

<210> SEQ ID NO 67
<211> LENGTH: 120
<212> TYPE: PRT
<213> ORGANISM: artificial sequence
<220> FEATURE:
<223> OTHER INFORMATION: G3 amino acid sequence

<400> SEQUENCE: 67

Glu Val Gln Leu Gln Ala Ser Gly Gly Gly Leu Ala Gln Ala Gly Gly
1               5                   10                  15

Ser Leu Arg Leu Ser Cys Thr Ala Ser Gly Arg Thr Phe Ser Thr Tyr
            20                  25                  30

Phe Met Ala Trp Phe Arg Gln Pro Pro Gly Lys Glu Arg Glu Tyr Val
        35                  40                  45

Gly Gly Ile Arg Trp Ser Asp Gly Val Pro His Tyr Ala Asp Ser Val
    50                  55                  60
```

-continued

Lys Gly Arg Phe Thr Ile Ser Arg Asp Asn Ala Lys Asn Thr Val Tyr
 65                  70                  75                  80

Leu Gln Met Asn Ser Leu Lys Ser Glu Asp Thr Ala Val Tyr Phe Cys
                 85                  90                  95

Ala Ser Arg Gly Ile Ala Asp Gly Ser Asp Phe Gly Tyr Gly Gln
            100                 105                 110

Gly Thr Gln Val Thr Val Ser Ser
            115                 120

<210> SEQ ID NO 68
<211> LENGTH: 122
<212> TYPE: PRT
<213> ORGANISM: artificial sequence
<220> FEATURE:
<223> OTHER INFORMATION: G1 amino acid sequence

<400> SEQUENCE: 68

Gln Val Lys Leu Glu Glu Ser Gly Gly Gly Leu Val Gln Pro Gly Gly
  1               5                  10                  15

Ser Leu Arg Leu Ser Cys Ala Ala Ser Gly Ser Ile Phe Ser Ile Lys
                 20                  25                  30

Ala Met Ala Trp Tyr Arg Gln Ala Pro Gly Lys Gln Arg Glu Leu Val
             35                  40                  45

Ala Tyr Ile Arg Ser Gly Gly Thr Thr Asn Tyr Ala Asp Ser Val Lys
         50                  55                  60

Gly Arg Phe Thr Ile Ser Arg Asp Ile Ala Lys Asn Thr Val Tyr Leu
 65                  70                  75                  80

Gln Met Asn Ser Leu Lys Pro Glu Asp Thr Ala Val Tyr Tyr Cys Asn
                 85                  90                  95

Ala Asp Tyr Ser Pro Pro Gly Ser Arg Phe Pro Asp Leu Gly Pro Trp
            100                 105                 110

Gly Gln Gly Thr Gln Val Thr Val Ser Ser
            115                 120

<210> SEQ ID NO 69
<211> LENGTH: 116
<212> TYPE: PRT
<213> ORGANISM: artificial sequence
<220> FEATURE:
<223> OTHER INFORMATION: NG7 amino acid sequence

<400> SEQUENCE: 69

Gln Val Lys Leu Glu Glu Ser Gly Gly Gly Leu Ala Gln Pro Gly Gly
  1               5                  10                  15

Ser Leu Arg Leu Ser Cys Ala Ala Ser Gly Leu Val Phe Ser Ala Asn
                 20                  25                  30

Thr Met Ala Trp Tyr Arg Arg Ala Pro Gly Lys Gln Arg Glu Leu Val
             35                  40                  45

Ala Arg Ile Ser Thr Asp Gly Arg Thr Asn Tyr Ala Asp Ser Val Lys
         50                  55                  60

Gly Arg Phe Thr Ile Ser Arg Asp Asn Arg Glu Lys Thr Val Phe Leu
 65                  70                  75                  80

Gln Met Asn Arg Leu Asn Pro Asp Asp Thr Ala Val Tyr Tyr Cys Asn
                 85                  90                  95

Ala Asn Trp Leu Ser Lys Phe Asp Tyr Trp Gly Gln Gly Thr Gln Val
            100                 105                 110

Thr Val Ser Ser
            115

<210> SEQ ID NO 70
<211> LENGTH: 119
<212> TYPE: PRT
<213> ORGANISM: artificial sequence
<220> FEATURE:
<223> OTHER INFORMATION: G5 amino acid sequence

<400> SEQUENCE: 70

```
Asp Val Gln Leu Gln Ala Ser Gly Gly Gly Leu Val Gln Ala Gly Gly
1               5                   10                  15

Ser Leu Arg Leu Ser Cys Val Ala Ser Gly Ser Ile Phe Ser Val Asn
            20                  25                  30

Ala Val Ala Trp Tyr Arg Gln Ala Pro Gly Lys Gln Arg Glu Leu Val
        35                  40                  45

Ala Tyr Ile Arg Arg Ser Gly Ser Thr Asn Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Asn
                85                  90                  95

Ala Asp Phe Gly Ser Asp Tyr Val Val Leu Gly Ser Trp Gly Gln Gly
            100                 105                 110

Thr Gln Val Thr Val Ser Ser
        115
```

<210> SEQ ID NO 71
<211> LENGTH: 120
<212> TYPE: PRT
<213> ORGANISM: artificial sequence
<220> FEATURE:
<223> OTHER INFORMATION: G9 amino acid sequence

<400> SEQUENCE: 71

```
Gln Val Lys Leu Glu Glu Ser Gly Gly Gly Leu Val Gln Ala Gly Gly
1               5                   10                  15

Ser Leu Arg Leu Ser Cys Ala Ala Ser Gly Ser Ile Phe Ser Ile Lys
            20                  25                  30

Ala Leu Ala Trp Tyr Arg Gln Ala Pro Gly Lys Gln Arg Glu Leu Val
        35                  40                  45

Ala Tyr Ile Thr Ser Gly Gly Asn Thr Asn Tyr Ala Asp Ser Val Arg
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Asn
                85                  90                  95

Ala Asp Phe Gly Glu Gly Thr Ile Ile Ser Leu Gly Pro Trp Gly Gln
            100                 105                 110

Gly Thr Gln Val Thr Val Ser Ser
        115                 120
```

<210> SEQ ID NO 72
<211> LENGTH: 120
<212> TYPE: PRT
<213> ORGANISM: artificial sequence
<220> FEATURE:
<223> OTHER INFORMATION: G7 amino acid sequence

<400> SEQUENCE: 72

-continued

Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Glu Phe Ser Ile Asn
            20                  25                  30

Ala Met Ala Trp Tyr Arg Gln Ala Pro Gly Lys Gln Arg Glu Leu Val
        35                  40                  45

Ala Ala Leu Thr Ser Gly Gly Asn Thr His Tyr Ala Asp Ser Val Lys
    50                  55                  60

Gly Arg Phe Thr Ile Ser Arg Asp Asn Ala Lys Asn Thr Trp Tyr Leu
65                  70                  75                  80

Gln Met Asn Ser Leu Lys Pro Glu Asp Thr Ala Val Tyr Tyr Cys Asn
            85                  90                  95

Ala Asp Phe Gly Thr Ala Gly Leu Val Val Leu Gly Pro Trp Gly Gln
        100                 105                 110

Gly Thr Gln Val Thr Val Ser Ser
        115                 120

<210> SEQ ID NO 73
<211> LENGTH: 118
<212> TYPE: PRT
<213> ORGANISM: artificial sequence
<220> FEATURE:
<223> OTHER INFORMATION: G6-2 amino acid sequence

<400> SEQUENCE: 73

Glu Val Gln Leu Gln Ala Ser Gly Gly Gly Leu Val Gln Pro Gly Gly
1               5                   10                  15

Ser Leu Arg Leu Ser Cys Ala Ala Ser Gly Ser Ile Phe Ser Ile Asn
            20                  25                  30

Ala Met Ala Trp Tyr Arg Gln Ala Pro Gly Lys Gln Arg Glu Leu Val
        35                  40                  45

Ala Tyr Ile Arg Ser Asn Gly Arg Thr Asn Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Leu Glu Asp Thr Ala Val Tyr Tyr Cys Asn
            85                  90                  95

Ala Asp Tyr Gly Pro Pro Val Ser Ile Gly Pro Trp Gly Gln Gly Thr
        100                 105                 110

Gln Val Thr Val Ser Ser
        115

<210> SEQ ID NO 74
<211> LENGTH: 118
<212> TYPE: PRT
<213> ORGANISM: artificial sequence
<220> FEATURE:
<223> OTHER INFORMATION: G10 amino acid sequence

<400> SEQUENCE: 74

Glu Val Gln Leu Val Glu Ser Gly Gly Gly Leu Val Gln Ala Gly Gly
1               5                   10                  15

Ser Leu Arg Leu Ser Cys Val Val Ser Gly Ser Leu Leu Ser Ile Lys
            20                  25                  30

Ala Met Ala Trp Phe Arg Gln Pro Pro Gly Lys Gln Arg Glu Leu Val
        35                  40                  45

Ala Ala Val Thr Ser Gly Gly Ser Thr His Tyr Leu Asp Ser Val Lys
    50                  55                  60

Gly Arg Phe Thr Ile Ser Arg Asp Asn Ala Asn Thr Val His Leu Gln
65                  70                  75                  80

Met Asn Ser Leu Lys Pro Glu Asp Thr Ala Val Tyr Tyr Cys Asn Ala
                85                  90                  95

Asp Phe Gly Thr Asp Tyr Val Asp Leu Gly Pro Trp Gly Gln Gly Thr
            100                 105                 110

Gln Val Thr Val Ser Ser
        115

<210> SEQ ID NO 75
<211> LENGTH: 122
<212> TYPE: PRT
<213> ORGANISM: artificial sequence
<220> FEATURE:
<223> OTHER INFORMATION: G2 amino acid sequence

<400> SEQUENCE: 75

Asp Val Gln Leu Gln Ala Ser Gly Gly Gly Leu Val Gln Pro Gly Gly
1               5                   10                  15

Ser Leu Arg Leu Ser Cys Ala Val Ser Gly Ser Ile Phe Ser Ile Asn
            20                  25                  30

Ala Met Gly Trp Tyr Arg Gln Ala Pro Gly Lys Gln Arg Glu Leu Val
        35                  40                  45

Ala Ala Ile Thr Lys Ser Asn Asn Ile Asn Tyr Ala Asp Ser Val Lys
    50                  55                  60

Gly Arg Phe Thr Ile Ser Thr Asp Asn Ala Lys Asn Thr Val Tyr Leu
65                  70                  75                  80

Gln Met Asn Ser Leu Lys Pro Glu Asp Thr Ala Val Tyr Tyr Cys Asn
                85                  90                  95

Gly Phe Phe Ala Leu Pro Gly Tyr Ser Ser Glu Glu Phe Gly Pro Trp
            100                 105                 110

Gly Gln Gly Thr Gln Val Thr Val Ser Ser
        115                 120

<210> SEQ ID NO 76
<211> LENGTH: 120
<212> TYPE: PRT
<213> ORGANISM: artificial sequence
<220> FEATURE:
<223> OTHER INFORMATION: G8 amino acid sequence

<400> SEQUENCE: 76

Glu Val Gln Leu Val Glu Ser Gly Gly Gly Leu Val Gln Pro Gly Gly
1               5                   10                  15

Ser Leu Arg Leu Ser Cys Val Ala Ser Gly Asn Ile Phe Asp Met Asn
            20                  25                  30

Arg Met Gly Trp Tyr Arg Gln Pro Pro Gly Lys Gln Arg Glu Leu Val
        35                  40                  45

Ala Asp Ile Arg Asp Gly Gly Ser Thr Ile Tyr Ser Asp Ser Val Lys
    50                  55                  60

Gly Arg Phe Thr Ile Ser Arg Asp Asn Ala Lys Asn Thr Leu Tyr Leu
65                  70                  75                  80

Gln Met Asn Ser Leu Lys Pro Asp Asp Thr Ala Val Tyr Tyr Cys Asn
                85                  90                  95

Ala Gly Arg Thr Gly Asp Arg Phe Asn Leu Val Ala Tyr Trp Gly Gln
            100                 105                 110

Gly Thr Gln Val Thr Val Ser Ser
        115                 120

```
            115                 120
```

<210> SEQ ID NO 77
<211> LENGTH: 124
<212> TYPE: PRT
<213> ORGANISM: artificial sequence
<220> FEATURE:
<223> OTHER INFORMATION: G17 amino acid sequence

<400> SEQUENCE: 77

```
Asp Val Gln Leu Gln Ala Ser Gly Gly Gly Leu Val Gln His Gly Gly
1               5                   10                  15

Ser Leu Arg Leu Ser Cys Glu Ala Ser Gly Arg Thr Phe Ser Gly Tyr
            20                  25                  30

Ala Met Ala Trp Phe Arg Gln Ala Pro Gly Lys Glu His Glu Phe Val
        35                  40                  45

Ala Ala Ile Ser Ser Ser Ser Asn Ser Ala Pro Tyr Tyr Ala Asn Ser
    50                  55                  60

Val Lys Gly Arg Phe Thr Ile Ser Arg Asp Asn Ala Lys Asn Thr Val
65                  70                  75                  80

Tyr Leu Gln Met Asn Asn Leu Gln Thr Glu Asp Thr Ala Val Tyr Tyr
                85                  90                  95

Cys Ala Ala Arg Tyr Gly Thr Lys Arg Tyr Val Ala Arg Glu Tyr Asp
            100                 105                 110

Ser Trp Gly Gln Gly Thr Gln Val Thr Val Ser Ser
        115                 120
```

<210> SEQ ID NO 78
<211> LENGTH: 115
<212> TYPE: PRT
<213> ORGANISM: artificial sequence
<220> FEATURE:
<223> OTHER INFORMATION: G25 amino acid sequence

<400> SEQUENCE: 78

```
Asp Val Gln Leu Gln Ala Ser Gly Gly Gly Val Val Gln Ala Gly Gly
1               5                   10                  15

Ser Leu Arg Leu Ser Cys Thr Ala Ser Gly Ser Ile Arg Ser Ile Asn
            20                  25                  30

Gly Met Gly Trp Ser Arg Val Ala Pro Gly Lys Gln Arg Asp Phe Val
        35                  40                  45

Ala Arg Ile Asp Ser Arg Gly Ser Ala Tyr Tyr Ala Asp Ser Val Glu
    50                  55                  60

Gly Arg Phe Thr Ile Ser Arg Asp Asn Ala Lys Asn Thr Val Tyr Leu
65                  70                  75                  80

Gln Val Asp Thr Leu Lys Pro Glu Asp Thr Ala Val Tyr Tyr Cys Phe
                85                  90                  95

Ala Trp Gln Gly Ala Glu Thr Tyr Trp Gly Leu Gly Thr Gln Val Thr
            100                 105                 110

Val Ser Ser
    115
```

<210> SEQ ID NO 79
<211> LENGTH: 118
<212> TYPE: PRT
<213> ORGANISM: artificial sequence
<220> FEATURE:
<223> OTHER INFORMATION: NG1 amino acid sequence

<400> SEQUENCE: 79

```
Gln Val Lys Leu Glu Glu Ser Gly Gly Gly Leu Val Gln Pro Gly Gly
1               5                   10                  15

Ser Leu Arg Leu Ser Cys Ala Ala Ser Gly Ser Ile Gly Asp Thr Tyr
            20                  25                  30

Ala Met Ala Trp Tyr Arg Gln Ala Pro Gly Lys Gln Arg Asp Leu Val
        35                  40                  45

Ala Tyr Ile Thr Asn Gly Gly Ser Thr Asp Tyr Ala Ala Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Asn
                85                  90                  95

Gly Ala Thr Arg Gly Ala Gln Leu Val Phe Asp Trp Gly Gln Gly Thr
            100                 105                 110

Gln Val Thr Val Ser Ser
        115
```

<210> SEQ ID NO 80
<211> LENGTH: 124
<212> TYPE: PRT
<213> ORGANISM: artificial sequence
<220> FEATURE:
<223> OTHER INFORMATION: NG20 amino acid sequence

<400> SEQUENCE: 80

```
Gln Val Lys Leu Glu Glu Ser Gly Gly Gly Leu Val Gln His Gly Gly
1               5                   10                  15

Ser Leu Arg Leu Ser Cys Ala Ala Ser Gly Gly Thr Phe Ser Asn Tyr
            20                  25                  30

Ala Met Ala Trp Phe Arg Gln Ala Pro Gly Lys Glu Arg Glu Phe Val
        35                  40                  45

Ala Ala Ile Ser Val Ser Ala Asn Ser Ala Pro Tyr Tyr Ala Asn Ser
    50                  55                  60

Val Lys Gly Arg Phe Thr Ile Ser Arg Asp Asn Ala Lys Asn Thr Val
65                  70                  75                  80

Tyr Leu Gln Met Asn Ser Leu Lys Thr Glu Asp Thr Ala Val Tyr Tyr
                85                  90                  95

Cys Ala Ala Arg Tyr Gly Thr Lys Arg Tyr Val Ala Arg Glu Tyr Asp
            100                 105                 110

Ser Trp Gly Gln Gly Thr Gln Val Thr Val Ser Ser
        115                 120
```

<210> SEQ ID NO 81
<211> LENGTH: 115
<212> TYPE: PRT
<213> ORGANISM: artificial sequence
<220> FEATURE:
<223> OTHER INFORMATION: NG21 amino acid sequence

<400> SEQUENCE: 81

```
Gln Val Lys Leu Glu Glu Ser Gly Gly Gly Leu Val Gln Pro Gly Gly
1               5                   10                  15

Ser Leu Arg Leu Ser Cys Ala Ala Ser Gly Ser Ser Val Ser Leu Asn
            20                  25                  30

Ala Met Gly Trp Ser Arg Val Gln Pro Gly Ser Thr Arg Asp Phe Val
        35                  40                  45

Ala Arg Ile Ala Ala Asp Gly Ser Thr His Tyr Ala Asp Ser Val Glu
```

```
                    50                  55                  60
Gly Arg Phe Thr Ile Ser Gly Asp Ala Ala Arg Asn Thr Val Tyr Leu
 65                  70                  75                  80

Gln Met Asp Ser Leu Lys Pro Glu Asp Thr Ala Val Tyr Tyr Cys Phe
                 85                  90                  95

Ala Trp Leu Gly Thr Asp Thr Tyr Trp Gly Gln Gly Thr Gln Val Thr
                100                 105                 110

Val Ser Ser
        115

<210> SEQ ID NO 82
<211> LENGTH: 114
<212> TYPE: PRT
<213> ORGANISM: artificial sequence
<220> FEATURE:
<223> OTHER INFORMATION: G14 amino acid sequence

<400> SEQUENCE: 82

Asp Val Gln Leu Gln Ala Ser Gly Gly Gly Leu Val Gln Ala Gly Gly
 1                   5                  10                  15

Ser Leu Thr Leu Ser Cys Ala Ala Ser Gly Ser Ile Gly Asp Asn Asn
                 20                  25                  30

Ala Met Gly Trp Ser Arg Thr Pro Gly Lys Gln Arg Glu Phe Val
             35                  40                  45

Ala Arg Ile Asp Ser Gly Gly Ile Thr Arg Tyr Ala Asp Ser Leu Lys
         50                  55                  60

Gly Arg Phe Thr Val Ser Arg Asp Thr Gly Lys Asn Thr Val Ser Leu
 65                  70                  75                  80

Gln Met Asn Ser Leu Lys Ala Glu Asp Thr Gly Val Tyr Tyr Cys Phe
                 85                  90                  95

Ala His Val Gly Gly Thr Ile Trp Gly Gln Gly Thr Gln Val Thr Val
                100                 105                 110

Ser Ser

<210> SEQ ID NO 83
<211> LENGTH: 124
<212> TYPE: PRT
<213> ORGANISM: artificial sequence
<220> FEATURE:
<223> OTHER INFORMATION: NGS1 amino acid sequence

<400> SEQUENCE: 83

Gln Val Gln Leu Val Glu Ser Gly Gly Gly Leu Val Gln Pro Gly Gly
 1                   5                  10                  15

Ser Leu Arg Leu Ser Cys Leu Pro Ser Gly Gly Ile Phe Thr Ile Asn
                 20                  25                  30

Ser Met Gly Trp Tyr Arg Gln Ala Pro Gly Lys Gln Arg Glu Leu Val
             35                  40                  45

Ala Ser Ile Thr Gly Gly Gly Ser Ser Arg Tyr Ala Asp Ser Val Lys
         50                  55                  60

Gly Arg Phe Ile Met Ser Arg Asp Asn Ala Lys Asn Met Val Tyr Leu
 65                  70                  75                  80

Gln Met Asn Ser Leu Lys Pro Glu Asp Thr Ala Val Tyr Tyr Cys Asn
                 85                  90                  95

Thr Ile Pro Pro Ala Arg Thr Gln Ser Asp His Gly Glu Trp Tyr Asp
                100                 105                 110

Tyr Trp Gly Gln Gly Thr Gln Val Thr Val Ser Ser
```

```
<210> SEQ ID NO 84
<211> LENGTH: 118
<212> TYPE: PRT
<213> ORGANISM: artificial sequence
<220> FEATURE:
<223> OTHER INFORMATION: G12 amino acid sequence

<400> SEQUENCE: 84

Gln Val Lys Leu Glu Glu Ser Gly Gly Gly Leu Val Gln Ala Gly Gly
1               5                   10                  15

Ser Leu Arg Leu Ser Cys Ala Ala Ser Ser Ile Phe Ser Ile Asn
            20                  25                  30

Met Ser Trp Tyr Arg Gln Ala Pro Gly Asn Glu Arg Glu Leu Val Ala
        35                  40                  45

Thr Ile Thr Arg His Asp Ser Thr His Tyr Ser Asp Ser Val Lys Gly
    50                  55                  60

Arg Phe Thr Ile Ser Arg Asp Asp Lys Asn Thr Ile Tyr Leu Gln
65                  70                  75                  80

Met Asn Ser Leu Lys Pro Glu Asp Thr Ala Val Tyr Tyr Cys Ser Gly
                85                  90                  95

Phe Phe Leu Asp Gly Ser Thr Trp His Pro Tyr Trp Gly Gln Gly Thr
            100                 105                 110

Gln Val Thr Val Ser Ser
        115

<210> SEQ ID NO 85
<211> LENGTH: 122
<212> TYPE: PRT
<213> ORGANISM: artificial sequence
<220> FEATURE:
<223> OTHER INFORMATION: G6 amino acid sequence

<400> SEQUENCE: 85

Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Ile Val Ser Ile Asn
            20                  25                  30

Ala Met Ala Trp Tyr Arg Gln Ala Pro Gly Lys Gln Arg Glu Leu Val
        35                  40                  45

Ala Tyr Ile Arg Ser Asn Gly Ser Thr Asn Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Leu Glu Asp Thr Ala Val Tyr Tyr Cys Asn
                85                  90                  95

Gly Phe Phe Thr Leu Pro Gly Tyr Ser Ser Glu Glu Phe Gly Pro Trp
            100                 105                 110

Gly Gln Gly Thr Gln Val Thr Val Ser Ser
        115                 120

<210> SEQ ID NO 86
<211> LENGTH: 123
<212> TYPE: PRT
<213> ORGANISM: artificial sequence
<220> FEATURE:
<223> OTHER INFORMATION: G22# amino acid sequence

<400> SEQUENCE: 86
```

```
Glu Val Gln Leu Val Glu Ser Gly Gly Gly Leu Val Gln Pro Gly Gly
 1               5                  10                  15

Ser Leu Arg Leu Ser Cys Ala Ala Ser Glu Ser Ile Phe Ser Ile Asn
            20                  25                  30

Ala Met Gly Trp Tyr Arg Gln Ala Pro Gly Lys Gln Arg Glu Tyr Val
        35                  40                  45

Ala Gly Ile Thr Lys Gly Gly Arg Thr Asn Tyr Ala Asp Ser Val Lys
    50                  55                  60

Gly Arg Phe Thr Ile Ser Arg Asp Asp Ala Lys Asn Thr Val Tyr Leu
65                  70                  75                  80

Gln Met Asn Ser Leu Lys Pro Glu Asp Thr Ala Val Tyr Tyr Cys Asn
                85                  90                  95

Gly Leu Cys Ser Gly Arg Glu Cys Tyr Gly Asp Ser Leu Phe Ala Ala
            100                 105                 110

Trp Gly Gln Gly Thr Gln Val Thr Val Ser Ser
        115                 120
```

<210> SEQ ID NO 87
<211> LENGTH: 119
<212> TYPE: PRT
<213> ORGANISM: artificial sequence
<220> FEATURE:
<223> OTHER INFORMATION: G6-1 amino acid sequence

<400> SEQUENCE: 87

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Ser Ile Val Ser Ile Asn
            20                  25                  30

Ala Met Ala Trp Tyr Arg Gln Ala Pro Gly Lys Gln Arg Glu Leu Val
        35                  40                  45

Ala Tyr Ile Arg Ser Asn Gly Arg Thr Asn Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Leu Glu Asp Thr Ala Val Tyr Tyr Cys Ser
                85                  90                  95

Gly Phe Phe Leu Asp Gly Ser Thr Trp His Pro Tyr Trp Gly Gln Gly
            100                 105                 110

Thr Gln Val Thr Val Ser Ser
        115
```

<210> SEQ ID NO 88
<211> LENGTH: 123
<212> TYPE: PRT
<213> ORGANISM: artificial sequence
<220> FEATURE:
<223> OTHER INFORMATION: G13# amino acid sequence

<400> SEQUENCE: 88

```
Glu Val Gln Leu Val Glu Ser Gly Gly Gly Leu Ala Gln Ala Gly Gly
 1               5                  10                  15

Ser Leu Arg Leu Ser Cys Ala Ala Ser Gly Phe Thr Phe Asp Asp Tyr
            20                  25                  30

Ala Ile Gly Trp Phe Arg Gln Ala Pro Gly Lys Glu Arg Glu Gly Val
        35                  40                  45

Ser Cys Ile Ser Ser Ser Asp Gly Ser Thr His Tyr Ala Asp Ser Val
```

```
                50              55              60
Lys Gly Arg Phe Thr Ile Ser Arg Asp Asn Ala Arg Asn Thr Val Thr
 65                  70                  75                  80

Leu Gln Ile Asn Ser Leu Lys Pro Glu Asp Thr Ala Val Tyr Tyr Cys
                 85                  90                  95

Ala Thr Pro Trp Val Thr Tyr Cys Pro Glu Asn Leu Leu Phe Ser Tyr
                100                 105                 110

Trp Gly Gln Gly Thr Gln Val Thr Val Ser Ser
            115                 120

<210> SEQ ID NO 89
<211> LENGTH: 123
<212> TYPE: PRT
<213> ORGANISM: artificial sequence
<220> FEATURE:
<223> OTHER INFORMATION: G13-# amino acid sequence

<400> SEQUENCE: 89

Gln Val Lys Leu Glu Glu Ser Gly Gly Gly Leu Val Gln Pro Gly Gly
  1               5                  10                  15

Ser Leu Arg Leu Ser Cys Ala Ala Ser Gly Phe Thr Phe Asp Asp Tyr
                 20                  25                  30

Ala Ile Gly Trp Phe Arg Gln Ala Pro Gly Lys Glu Arg Glu Gly Val
             35                  40                  45

Ser Cys Ile Thr Ser Ser Asp Gly Ser Thr Tyr Tyr Ala Asp Ser Val
 50                  55                  60

Lys Gly Arg Phe Thr Ile Ser Arg Asp Asn Ala Asn Asn Thr Val His
 65                  70                  75                  80

Leu Gln Ile Ser Asn Leu Lys Pro Glu Asp Thr Ala Val Tyr Tyr Cys
                 85                  90                  95

Ala Thr Pro Trp Val Thr Tyr Cys Pro Glu Asn Leu Leu Phe Ser Tyr
                100                 105                 110

Trp Gly Gln Gly Thr Gln Val Thr Val Ser Ser
            115                 120

<210> SEQ ID NO 90
<211> LENGTH: 120
<212> TYPE: PRT
<213> ORGANISM: artificial sequence
<220> FEATURE:
<223> OTHER INFORMATION: G31 amino acid sequence

<400> SEQUENCE: 90

Glu Val Gln Leu Val Glu Ser Gly Gly Gly Leu Val Gln Ala Gly Gly
  1               5                  10                  15

Ser Leu Thr Leu Ser Cys Ala Val Ser Gly Ser Ser Phe Ser Ile Lys
                 20                  25                  30

Ala Met Gly Trp Tyr Arg Leu Ala Pro Gly Lys Gln Arg Glu Leu Val
             35                  40                  45

Ala Ala Ile Thr Ser Gly Gly Ser Thr Asn Tyr Ala Asp Ser Val Lys
 50                  55                  60

Gly Arg Phe Thr Ile Ser Arg Asp Ser Ala Lys Asn Thr Val Tyr Leu
 65                  70                  75                  80

Gln Met Asn Ser Leu Lys Pro Glu Asp Thr Ala Val Tyr Tyr Cys Asn
                 85                  90                  95

Gly Phe Phe Glu Tyr Arg Gly Leu Glu Gln Leu Gly Pro Trp Gly Gln
                100                 105                 110
```

Gly Thr Gln Val Thr Val Ser Ser
        115                 120

<210> SEQ ID NO 91
<211> LENGTH: 120
<212> TYPE: PRT
<213> ORGANISM: artificial sequence
<220> FEATURE:
<223> OTHER INFORMATION: G4 amino acid sequence

<400> SEQUENCE: 91

Asp Val Gln Leu Gln Ala Ser Gly Gly Gly Leu Val Gln Pro Gly Gly
1               5                   10                  15

Ser Leu Arg Leu Ser Cys Ala Ala Ser Gly Ser Ile Val Gly Ile Arg
            20                  25                  30

Ala Met Thr Trp Tyr Arg Gln Ala Pro Gly Lys Gln Arg Glu Leu Val
        35                  40                  45

Ala Val Leu Thr Ser Ala Gly Lys Pro Met Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Asn
                85                  90                  95

Ala Asp Phe Gly Thr Pro Gly Ser Val Val Leu Gly Pro Trp Gly Gln
            100                 105                 110

Gly Thr Gln Val Thr Val Ser Ser
        115                 120

<210> SEQ ID NO 92
<211> LENGTH: 122
<212> TYPE: PRT
<213> ORGANISM: artificial sequence
<220> FEATURE:
<223> OTHER INFORMATION: NG2 amino acid sequence

<400> SEQUENCE: 92

Gln Val Lys Leu Glu Glu Ser Gly Gly Gly Leu Val Gln Pro Gly Gly
1               5                   10                  15

Ser Leu Arg Leu Ser Cys Ala Ala Ser Gly Ser Ile Leu Ser Ile Glu
            20                  25                  30

Ala Met Gly Trp Tyr Arg Gln Thr Leu Gly Lys Gln Arg Glu Leu Val
        35                  40                  45

Ala Ala Ile Thr Ser Gly Asp Ser Thr Asn Tyr Ala Asp Phe Val Lys
    50                  55                  60

Gly Arg Phe Thr Ile Ser Arg Asp Lys Ala Lys Asn Met Val Tyr Leu
65                  70                  75                  80

Gln Met Asn Ser Leu Lys Pro Glu Asp Thr Ala Val Tyr Phe Cys Asn
                85                  90                  95

Ala Leu Met Val Val Arg Ala Gly Ser Asn Pro Glu Ile Gly Pro Trp
            100                 105                 110

Gly Gln Gly Thr Gln Val Thr Val Ser Ser
        115                 120

<210> SEQ ID NO 93
<211> LENGTH: 123
<212> TYPE: PRT
<213> ORGANISM: artificial sequence
<220> FEATURE:
<223> OTHER INFORMATION: G13-# amino acid sequence

<400> SEQUENCE: 93

Gln Val Lys Leu Glu Glu Ser Gly Gly Gly Leu Val Gln Pro Gly Gly
1               5                   10                  15

Ser Leu Arg Leu Ser Cys Ala Ala Ser Gly Phe Thr Phe Asp Asp Tyr
            20                  25                  30

Ala Ile Gly Trp Phe Arg Gln Ala Pro Gly Lys Glu Arg Glu Gly Val
        35                  40                  45

Ser Cys Ile Ser Ser Ser Asp Gly Ser Thr Tyr Tyr Ala Asp Ser Val
    50                  55                  60

Lys Gly Arg Phe Thr Ile Ser Arg Asp Asn Ala Asn Asn Thr Val His
65                  70                  75                  80

Leu Gln Ile Ser Asn Leu Lys Pro Glu Asp Thr Ala Val Tyr Tyr Cys
                85                  90                  95

Ala Thr Pro Trp Val Thr Tyr Cys Pro Glu Asn Leu Leu Phe Ser Tyr
            100                 105                 110

Trp Gly Gln Gly Thr Gln Val Thr Val Ser Ser
        115                 120

<210> SEQ ID NO 94
<211> LENGTH: 115
<212> TYPE: PRT
<213> ORGANISM: artificial sequence
<220> FEATURE:
<223> OTHER INFORMATION: G20 amino acid sequence

<400> SEQUENCE: 94

Glu Val Gln Leu Val Glu Ser Gly Gly Gly Leu Val Gln Pro Gly Gly
1               5                   10                  15

Ser Leu Arg Leu Ser Cys Val Val Ser Ala Arg Gly Val Ser Leu Asp
            20                  25                  30

Ala Val Gly Trp Ser Arg Val Ala Pro Gly Lys Gln Arg Asp Phe Val
        35                  40                  45

Ala Arg Ile Asp Arg Arg Gly Ser Thr Tyr Tyr Ala Val Ser Val Glu
    50                  55                  60

Gly Arg Ser Thr Ile Ser Arg Asp Asn Ala Lys Asn Thr Val Tyr Leu
65                  70                  75                  80

Gln Leu Asp Thr Leu Lys Pro Glu Asp Thr Ala Val Tyr Tyr Cys Phe
                85                  90                  95

Ala Trp Gln Gly Ala Glu Thr His Trp Gly Leu Gly Thr Gln Val Thr
            100                 105                 110

Val Ser Ser
        115

<210> SEQ ID NO 95
<211> LENGTH: 115
<212> TYPE: PRT
<213> ORGANISM: artificial sequence
<220> FEATURE:
<223> OTHER INFORMATION: NG3 amino acid sequence

<400> SEQUENCE: 95

Gln Val Lys Leu Glu Glu Ser Gly Gly Gly Leu Val Gln Ala Gly Gly
1               5                   10                  15

Ser Leu Thr Leu Ser Cys Val Ala Ser Gly Ser His Phe Ser Phe Asn
            20                  25                  30

Asp Met Gly Trp Tyr Arg Gln Asp Pro Trp Lys Gly Arg Asp Leu Val
        35                  40                  45

Ala Ala Ile Thr Ser Ser Arg Asn Thr Leu Tyr Val Asp Ser Val Lys
            50                  55                  60

Gly Arg Phe Thr Ile Ser Arg Asp Asp Ala Lys Asn Thr Val Tyr Leu
65                  70                  75                  80

Gln Met Asn Asn Leu Lys Pro Glu Asp Thr Ala Val Tyr Tyr Cys Asn
                85                  90                  95

Pro Tyr Pro Ser Pro Asn Asn Tyr Trp Gly Gln Gly Thr Gln Val Thr
                100                 105                 110

Val Ser Ser
        115

<210> SEQ ID NO 96
<211> LENGTH: 116
<212> TYPE: PRT
<213> ORGANISM: artificial sequence
<220> FEATURE:
<223> OTHER INFORMATION: NG4 amino acid sequence

<400> SEQUENCE: 96

Gln Val Lys Leu Glu Glu Ser Gly Gly Gly Leu Val Gln Pro Gly Gly
1               5                   10                  15

Ser Leu Arg Leu Ser Cys Ala Ala Ser Gly Ser Pro Phe Thr Ile Asn
                20                  25                  30

Ala Met Gly Trp Tyr Arg Gln Ala Pro Gly Lys Gln Arg Glu Leu Val
            35                  40                  45

Ala Ala Ile Thr Arg Ser Gly Lys Thr Asn Tyr Ala Asp Ser Val Lys
        50                  55                  60

Gly Arg Phe Thr Ile Ser Gly Asp Asn Ala Leu Thr Thr Val Tyr Leu
65                  70                  75                  80

Gln Met Asn Asn Leu Gln Pro Glu Asp Thr Ala Val Tyr Tyr Cys Asn
                85                  90                  95

Gly Phe Tyr Gly Ser Glu Phe Gly Pro Trp Gly Gln Gly Thr Gln Val
                100                 105                 110

Thr Val Ser Ser
        115

<210> SEQ ID NO 97
<211> LENGTH: 124
<212> TYPE: PRT
<213> ORGANISM: artificial sequence
<220> FEATURE:
<223> OTHER INFORMATION: NG5 amino acid sequence

<400> SEQUENCE: 97

Gln Val Lys Leu Glu Glu Ser Gly Gly Gly Leu Val Gln Ala Gly Gly
1               5                   10                  15

Ser Ala Thr Leu Ser Cys Ser Ala Pro Gly Asp Thr Leu Ser Arg Tyr
                20                  25                  30

Ala Val Gly Trp Phe Arg Gln Gly Pro Gly Gln Glu Arg Asp Phe Val
            35                  40                  45

Ala Ser Ile Thr Trp Ser Gly Asp Tyr Thr Tyr Tyr Lys Asp Ser Val
        50                  55                  60

Lys Gly Arg Phe Thr Ile Ser Arg Asp Ser Val Asn Asn Met Val Tyr
65                  70                  75                  80

Leu Arg Met Asn Ser Leu Lys Pro Glu Asp Thr Ala Leu Tyr Tyr Cys
                85                  90                  95

Ala Ala Asp Lys Ser Ser Phe Arg Leu Arg Gly Pro Gly Leu Tyr Asp
                100                 105                 110

```
Tyr Arg Gly Gln Gly Thr Gln Val Thr Val Ser Ser
        115                 120
```

<210> SEQ ID NO 98
<211> LENGTH: 123
<212> TYPE: PRT
<213> ORGANISM: artificial sequence
<220> FEATURE:
<223> OTHER INFORMATION: NG6# amino acid sequence

<400> SEQUENCE: 98

```
Gln Val Lys Leu Glu Glu Ser Gly Gly Leu Val Gln Pro Gly Gly
1               5                   10                  15

Ser Leu Arg Leu Ser Cys Ala Ala Ser Gly Phe Thr Phe Asp Tyr Tyr
            20                  25                  30

Ala Ile Gly Trp Phe Arg Gln Ala Pro Gly Lys Glu Arg Glu Gly Val
        35                  40                  45

Ser Cys Ile Ser Ser Arg Asp Gly Thr Thr His Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Ile Asp Ser Leu Lys Pro Glu Asp Thr Ala Val Tyr Tyr Cys
                85                  90                  95

Ala Thr Pro Trp Val Thr Tyr Cys Pro Glu Asn Leu Leu Phe Ser Tyr
            100                 105                 110

Trp Gly Gln Gly Thr Gln Val Thr Val Ser Ser
        115                 120
```

<210> SEQ ID NO 99
<211> LENGTH: 125
<212> TYPE: PRT
<213> ORGANISM: artificial sequence
<220> FEATURE:
<223> OTHER INFORMATION: NG8 amino acid sequence

<400> SEQUENCE: 99

```
Gln Val Lys Leu Glu Glu Ser Gly Gly Gly Phe Val Gln Pro Gly Gly
1               5                   10                  15

Ser Leu Arg Leu Ser Cys Ala Ala Ser Gly Phe Ser Leu His Tyr Tyr
            20                  25                  30

Ala Ile Gly Trp Phe Arg Gln Ala Pro Gly Lys Glu Arg Glu Trp Val
        35                  40                  45

Ser Ala Ile Ser Asn Ile Asp Asp Thr Tyr Tyr Glu Asp Ser Val
    50                  55                  60

Lys Gly Arg Phe Thr Ile Ser Arg Asp Asn Ala Lys Asn Thr Ala Tyr
65                  70                  75                  80

Leu Gln Met Asn Asn Leu Lys Pro Glu Asp Thr Ala Val Tyr Tyr Cys
                85                  90                  95

Ala Ala Asp Lys Asp Val Val Val Arg Thr Gly Leu Ser Glu Ser
            100                 105                 110

Asp Tyr Trp Gly Gln Gly Thr Gln Val Thr Val Ser Ser
        115                 120                 125
```

<210> SEQ ID NO 100
<211> LENGTH: 120
<212> TYPE: PRT
<213> ORGANISM: artificial sequence
<220> FEATURE:
<223> OTHER INFORMATION: NG9 amino acid sequence

<400> SEQUENCE: 100

Gln Val Lys Leu Glu Glu Ser Gly Gly Gly Leu Val Gln Ala Gly Gly
1               5                   10                  15

Ser Leu Arg Leu Ser Cys Ala Ala Ser Gly Ser Ile Phe Gly Ile Asn
            20                  25                  30

Ala Met Ala Trp Tyr Arg Gln Ala Pro Gly Lys Gln Arg Glu Leu Val
        35                  40                  45

Ala Val Ile Thr Ser Gly Gly Arg Thr Met Tyr Ala Glu Ser Val Lys
    50                  55                  60

Gly Arg Phe Ala Ile Ser Arg Asp Val Ala Lys Asn Thr Val Tyr Leu
65                  70                  75                  80

Gln Met Asn Ser Leu Lys Pro Glu Asp Thr Ala Val Tyr Tyr Cys Asn
                85                  90                  95

Gly Asp Trp Gly Ser Glu Gly Arg Val Asp Leu Gly Pro Trp Gly Gln
            100                 105                 110

Gly Thr Gln Val Thr Val Ser Ser
        115                 120

<210> SEQ ID NO 101
<211> LENGTH: 129
<212> TYPE: PRT
<213> ORGANISM: artificial sequence
<220> FEATURE:
<223> OTHER INFORMATION: NG10 amino acid sequence

<400> SEQUENCE: 101

Gln Val Lys Leu Glu Glu Ser Gly Gly Gly Leu Val Gln Pro Gly Gly
1               5                   10                  15

Thr Leu Arg Leu Ser Cys Ala Ala Ser Gly Ser Ile Arg Ser Ile Gly
            20                  25                  30

Asp Met Glu Trp Tyr Arg Gln Ala Pro Gly Gln Gln Arg Glu Leu Val
        35                  40                  45

Ala Ser Ile Ser Ala Gly Pro Glu Met Arg Ser Ala Gly Thr Pro Thr
    50                  55                  60

Tyr Ala Lys Ser Val Glu Gly Arg Phe Thr Ile Ser Arg Asp Asn Ile
65                  70                  75                  80

Lys Asn Met Met Trp Leu Gln Met Asn Ser Leu Arg Pro Glu Asp Thr
                85                  90                  95

Ala Val Tyr Ser Cys Asn Ala Asp Val Leu Thr Tyr Tyr Asn Gly Arg
            100                 105                 110

Tyr Ser Arg Asp Val Tyr Trp Gly Gln Gly Thr Gln Val Thr Val Ser
        115                 120                 125

Ser

<210> SEQ ID NO 102
<211> LENGTH: 118
<212> TYPE: PRT
<213> ORGANISM: artificial sequence
<220> FEATURE:
<223> OTHER INFORMATION: G12-1 amino acid sequence

<400> SEQUENCE: 102

Gln Val Lys Leu Glu Glu Ser Gly Gly Gly Leu Val Gln Ala Gly Gly
1               5                   10                  15

Ser Leu Arg Leu Ser Cys Ala Ala Ser Ser Ser Ile Phe Ser Ile Asn
            20                  25                  30

```
Met Ser Trp Tyr Arg Gln Ala Pro Gly Asn Glu Arg Glu Leu Val Ala
         35                  40                  45

Thr Ile Thr Arg His Asp Ser Thr His Tyr Ser Asp Ser Val Lys Gly
 50                  55                  60

Arg Phe Ala Ile Ser Arg Asp Asp Lys Asn Thr Ile Tyr Leu Gln
 65                  70                  75                  80

Met Asn Ser Leu Lys Pro Glu Asp Thr Ala Val Tyr Tyr Cys Ser Gly
                 85                  90                  95

Phe Phe Leu Asp Gly Ser Thr Trp Arg Pro Tyr Trp Gly Gln Gly Thr
                100                 105                 110

Gln Val Thr Val Ser Ser
        115
```

<210> SEQ ID NO 103
<211> LENGTH: 124
<212> TYPE: PRT
<213> ORGANISM: artificial sequence
<220> FEATURE:
<223> OTHER INFORMATION: G17-1 amino acid sequence

<400> SEQUENCE: 103

```
Asp Val Gln Leu Gln Ala Ser Gly Gly Gly Leu Val Gln Pro Gly Gly
 1               5                  10                  15

Ser Leu Arg Leu Ser Cys Ala Ala Ser Gly Arg Thr Leu Ser Gly Tyr
                 20                  25                  30

Ala Val Ala Trp Phe Arg Gln Ala Pro Gly Lys Glu Arg Glu Phe Val
                 35                  40                  45

Ala Ala Ile Ser Ser Ser Asp Asn Ser Ser Pro Tyr Tyr Ala Asn Val
         50                  55                  60

Val Lys Gly Arg Phe Thr Ile Ser Arg Asp Asn Ala Lys Asn Thr Val
 65                  70                  75                  80

Tyr Leu Gln Met Asn Ser Leu Gln Thr Glu Asp Thr Ala Leu Tyr Tyr
                 85                  90                  95

Cys Ala Ala Arg Tyr Gly Thr Lys Arg Tyr Val Ala Arg Glu Tyr Asp
                100                 105                 110

Ser Trp Gly Gln Gly Thr Gln Val Thr Val Ser Ser
        115                 120
```

<210> SEQ ID NO 104
<211> LENGTH: 122
<212> TYPE: PRT
<213> ORGANISM: artificial sequence
<220> FEATURE:
<223> OTHER INFORMATION: NG11 amino acid sequence

<400> SEQUENCE: 104

```
Gln Val Lys Leu Glu Glu Ser Gly Gly Gly Leu Val Gln Pro Gly Gly
 1               5                  10                  15

Ser Leu Arg Leu Ser Cys Ala Ala Ser Arg Ser Ile Phe Ser Ile Asn
                 20                  25                  30

Ala Met Ala Trp Tyr Arg Gln Ala Pro Gly Lys Gln Arg Glu Leu Val
                 35                  40                  45

Ala Tyr Ile Arg Ser Ser Gly Thr Thr Met Tyr Ala Asp Ser Val Lys
         50                  55                  60

Gly Arg Phe Thr Ile Ser Arg Asp Asn Ala Lys Asn Thr Val Tyr Leu
 65                  70                  75                  80

Gln Met Asn Ser Leu Lys Pro Glu Asp Thr Ala Val Tyr Tyr Cys Asn
                 85                  90                  95
```

-continued

```
Gly Asp Tyr Ser Pro Pro Gly Ser Thr Tyr Pro Asp Leu Gly Pro Trp
            100                 105                 110

Gly Gln Gly Thr Gln Val Thr Val Ser Ser
        115                 120

<210> SEQ ID NO 105
<211> LENGTH: 245
<212> TYPE: PRT
<213> ORGANISM: artificial sequence
<220> FEATURE:
<223> OTHER INFORMATION: G15(bi) amino acid sequence

<400> SEQUENCE: 105

Glu Val Gln Leu Gln Ala Ser Gly Gly Gly Leu Val Gln Pro Gly Gly
1               5                   10                  15

Ser Leu Arg Leu Ser Cys Ala Ala Ser Gly Phe Thr Phe Asp Asp Tyr
            20                  25                  30

Ala Ile Gly Trp Phe Arg Gln Ala Pro Gly Lys Glu Arg Glu Gly Val
        35                  40                  45

Ser Cys Ile Thr Ser Ser Asp Gly Ser Thr Tyr Tyr Ala Asp Ser Val
    50                  55                  60

Lys Gly Arg Phe Thr Ile Ser Arg Asp Asn Ala Asn Asn Thr Val His
65                  70                  75                  80

Leu Gln Ile Ser Asn Leu Lys Pro Glu Asp Thr Ala Val Tyr Tyr Cys
                85                  90                  95

Ala Thr Pro Trp Val Asn Tyr Cys Pro Glu Asn Leu Leu Phe Ser Tyr
            100                 105                 110

Trp Gly Gln Gly Thr Gln Val Thr Val Ser Ser Gln Ala Gln Val Gln
        115                 120                 125

Leu Val Glu Ser Gly Gly Gly Leu Ala Gln Ala Gly Gly Ser Leu Arg
    130                 135                 140

Leu Ser Cys Thr Ala Ser Gly Arg Thr Phe Ser Thr Tyr Phe Met Ala
145                 150                 155                 160

Trp Phe Arg Gln Pro Pro Gly Lys Glu Arg Glu Tyr Val Gly Gly Ile
                165                 170                 175

Arg Trp Ser Asp Gly Val Pro His Tyr Thr Asp Ser Val Lys Gly Arg
            180                 185                 190

Phe Thr Ile Ser Arg Asp Asn Ala Lys Asn Thr Val Tyr Leu Gln Met
        195                 200                 205

Asn Ser Leu Lys Ser Glu Asp Thr Ala Val Tyr Phe Cys Ala Ser Arg
    210                 215                 220

Gly Ile Ala Asp Gly Ser Asp Phe Gly Ser Tyr Gly Gln Gly Thr Gln
225                 230                 235                 240

Val Thr Val Ser Ser
                245

<210> SEQ ID NO 106
<211> LENGTH: 116
<212> TYPE: PRT
<213> ORGANISM: artificial sequence
<220> FEATURE:
<223> OTHER INFORMATION: G11 amino acid sequence

<400> SEQUENCE: 106

Gln Val Lys Leu Glu Glu Ser Gly Gly Gly Leu Val Gln Ala Gly Gly
1               5                   10                  15

Ser Leu Arg Leu Ser Cys Gly Ala Ser Gly Ile Ile Phe Ser Ala Thr
```

-continued

```
                20                  25                  30
Thr Met Ala Trp Tyr Arg Gln Ala Pro Gly Lys Gln Arg Glu Leu Val
                35                  40                  45
Ala Leu Ile Thr Ser Asp Trp His Thr Lys Tyr Ala Asp Ser Val Lys
    50                  55                  60
Asp Arg Phe Ser Ile Ser Arg Asp Asn Ala Lys Ser Thr Val His Leu
65                  70                  75                  80
Gln Met Asn Ser Leu Arg Ser Glu Asp Thr Ala Val Tyr Phe Cys Tyr
                85                  90                  95
Ala Arg Gln Ala Phe Ser Glu Pro Arg Trp Gly Gln Gly Thr Gln Val
                100                 105                 110
Thr Val Ser Ser
        115

<210> SEQ ID NO 107
<211> LENGTH: 115
<212> TYPE: PRT
<213> ORGANISM: artificial sequence
<220> FEATURE:
<223> OTHER INFORMATION: NG12 amino acid sequence

<400> SEQUENCE: 107

Gln Val Gln Leu Val Asp Ser Gly Gly Gly Leu Val Gln Pro Gly Gly
1               5                   10                  15
Ser Leu Arg Leu Ser Cys Ala Ala Ser Gly Ser Ser Gly Arg Ile Asp
                20                  25                  30
Ala Met Gly Trp Ser Arg Val Ala Pro Gly Lys Gln Arg Asp Phe Val
                35                  40                  45
Ala Arg Leu Gly Ser Asn Gly Phe Thr Gln Tyr Asp Ile Ser Val Glu
    50                  55                  60
Gly Arg Phe Thr Ile Ser Gly Asp Val Ala Lys Asn Thr Ile Tyr Leu
65                  70                  75                  80
Gln Met Asp Thr Leu Lys Pro Glu Asp Thr Ala Val Tyr Tyr Cys Phe
                85                  90                  95
Ala Trp Leu Gly Gln Asp Thr Val Trp Gly Gln Gly Thr Gln Val Thr
                100                 105                 110
Val Ser Ser
        115

<210> SEQ ID NO 108
<211> LENGTH: 124
<212> TYPE: PRT
<213> ORGANISM: artificial sequence
<220> FEATURE:
<223> OTHER INFORMATION: NG14 amino acid sequence

<400> SEQUENCE: 108

Gln Val Gln Leu Val Asp Ser Gly Gly Gly Leu Val Lys Ala Gly Ala
1               5                   10                  15
Ser Leu Arg Leu Ser Cys Ala Ala Ser Gly Asp Ala Leu Phe Asn Tyr
                20                  25                  30
Ala Met Gly Trp Phe Arg Gln Gly Pro Gly Lys Glu Arg Asp Phe Val
                35                  40                  45
Ala Ser Val Thr Arg Ser Gly Asp Asn Thr Tyr Tyr Lys Asp Ser Ala
    50                  55                  60
Lys Gly Arg Phe Thr Ile Ser Arg Asp Ala Lys Asn Thr Val Tyr
65                  70                  75                  80
```

```
Leu Gln Met Asn Ser Leu Lys Pro Glu Asp Thr Ala Val Tyr Phe Cys
                85                  90                  95

Ala Ala Asp Lys Ser Ser Phe Arg Leu Arg Gly Pro Gly Val Tyr Asp
            100                 105                 110

Tyr Arg Gly Gln Gly Thr Gln Val Thr Val Ser Ser
        115                 120

<210> SEQ ID NO 109
<211> LENGTH: 126
<212> TYPE: PRT
<213> ORGANISM: artificial sequence
<220> FEATURE:
<223> OTHER INFORMATION: NG13 amino acid sequence

<400> SEQUENCE: 109

Asp Val Gln Leu Val Asp Ser Gly Gly Gly Leu Val Gln Ala Gly Gly
1               5                   10                  15

Ser Leu Arg Leu Ser Cys Ala Val Ser Gly Ser Asp Gly Arg Val Met
            20                  25                  30

Leu Met Gly Trp Tyr Arg Gln Ala Pro Gly Gln Gln Arg Asp Leu Val
        35                  40                  45

Ala Ser Ile Thr Ser Ala Asp Tyr Thr Thr Tyr Ala Glu Ser Val Glu
    50                  55                  60

Gly Arg Phe Thr Ile Ser Thr Asp Asn Asn Lys Asn Thr Val Tyr Leu
65                  70                  75                  80

Gln Met Asn Ser Leu Lys Pro Glu Asp Thr Ala Val Tyr Phe Cys Lys
                85                  90                  95

Val Ile Ala Ala Thr Val Trp Gly Gln Glu Thr Gln Val Arg Gln Gly
            100                 105                 110

Leu Thr Phe Trp Gly Gln Gly Thr Gln Val Thr Val Ser Ser
        115                 120                 125

<210> SEQ ID NO 110
<211> LENGTH: 120
<212> TYPE: PRT
<213> ORGANISM: artificial sequence
<220> FEATURE:
<223> OTHER INFORMATION: G21 amino acid sequence

<400> SEQUENCE: 110

Glu Val Gln Leu Val Glu Ser Gly Gly Gly Leu Val Gln Pro Gly Gly
1               5                   10                  15

Ser Leu Arg Leu Ser Cys Val Ala Ser Gly Ser Ile Ser Ser Ala Arg
            20                  25                  30

Ser Met Thr Trp Tyr Arg Gln Ala Leu Gly Lys Gln Arg Glu Leu Val
        35                  40                  45

Ala Val Ile Met Gly Gly Gly Ser Thr Met Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Asn
                85                  90                  95

Ala Asp Trp Gly Gly Val Gly Phe Pro Asn Leu Gly Trp Gly Gln
            100                 105                 110

Gly Thr Gln Val Thr Val Ser Ser
        115                 120

<210> SEQ ID NO 111
```

```
<211> LENGTH: 123
<212> TYPE: PRT
<213> ORGANISM: artificial sequence
<220> FEATURE:
<223> OTHER INFORMATION: NG23 amino acid sequence

<400> SEQUENCE: 111

Asp Val Gln Leu Gln Ala Ser Gly Gly Gly Leu Val Gln Ile Gly Asp
1               5                   10                  15

Ser Val Arg Leu Ser Cys Ile Ala Ser Gly Gly Thr Phe Arg Thr Tyr
            20                  25                  30

Ala Ile Gly Trp Phe Arg Gln Ala Pro Gly Ala Glu Arg Glu Phe Val
        35                  40                  45

Ala Ala Ile Ser Arg Arg Gly Asn Lys Asp Tyr Ala Glu Ser Val Lys
    50                  55                  60

Gly Arg Phe Thr Val Ser Arg Asp Asn Ala Glu Asn Thr Val Tyr Leu
65                  70                  75                  80

Gln Met Asn Ser Leu Lys Pro Asp Asp Met Gly Val Tyr Tyr Cys Ala
                85                  90                  95

Ala Ser Ala Arg Asn Phe Ile Gly Thr Gln Pro Leu Asp Tyr Asp Tyr
            100                 105                 110

Trp Gly Gln Gly Thr Gln Val Thr Val Ser Ser
        115                 120

<210> SEQ ID NO 112
<211> LENGTH: 122
<212> TYPE: PRT
<213> ORGANISM: artificial sequence
<220> FEATURE:
<223> OTHER INFORMATION: NG15 amino acid sequence

<400> SEQUENCE: 112

Gln Val Lys Leu Glu Glu Ser Gly Gly Gly Leu Val Gln Ala Gly Gly
1               5                   10                  15

Ser Leu Arg Leu Ser Cys Ala Ala Ser Gly Trp Asn Leu Gly Asn Tyr
            20                  25                  30

Ala Leu Gly Trp Phe Arg Gln Ala Pro Gly Lys Glu Arg Glu Phe Val
        35                  40                  45

Ala Ala Ile Asp Trp Arg His Ser Ser Tyr Tyr Ala Asp Ser Val Lys
    50                  55                  60

Gly Arg Phe Thr Ile Ser Arg Asp Asn Thr Lys Asn Met Val Tyr Leu
65                  70                  75                  80

Gln Met Ser Ser Leu Lys Leu Glu Asp Thr Arg Leu Tyr Tyr Cys Ala
                85                  90                  95

Ala Ser Ser Leu Phe Pro Ser Ser Ala Pro Arg Gln Tyr Asp Tyr Trp
            100                 105                 110

Gly Gln Gly Thr Gln Val Thr Val Ser Ser
        115                 120

<210> SEQ ID NO 113
<211> LENGTH: 123
<212> TYPE: PRT
<213> ORGANISM: artificial sequence
<220> FEATURE:
<223> OTHER INFORMATION: NG16 amino acid sequence

<400> SEQUENCE: 113

Asp Val Gln Leu Val Asp Ser Gly Gly Gly Leu Val Gln Ala Gly Gly
1               5                   10                  15
```

Ser Leu Arg Leu Ser Cys Val Ala Ser Gly Arg Thr Phe Ser Asn Tyr
            20                  25                  30

Ala Met Gly Trp Tyr Arg Arg Pro Gly Leu Glu Arg Glu Phe Val
        35                  40                  45

Ala Ala Ile Val Gly Ser Gly Asp Ser Thr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Thr Leu Lys Pro Glu Asp Thr Ala Val Tyr Tyr Cys
                85                  90                  95

Ala Ser Ser Ser Asp Pro Arg Val Tyr Ile Ala Ser Thr Leu Asp Tyr
            100                 105                 110

Trp Gly Gln Gly Thr Gln Val Thr Val Ser Ser
        115                 120

<210> SEQ ID NO 114
<211> LENGTH: 119
<212> TYPE: PRT
<213> ORGANISM: artificial sequence
<220> FEATURE:
<223> OTHER INFORMATION: G23 amino acid sequence

<400> SEQUENCE: 114

Gln Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Ser Met Phe
            20                  25                  30

Ile Met Gly Trp Phe Arg Gln Ala Pro Gly Lys Glu Arg Glu Leu Val
        35                  40                  45

Ala Ala Ile Ser Arg Asn Ser Asn Leu Thr Tyr Tyr Phe Gln Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Leu Glu Asp Thr Ala Val Tyr Tyr Cys
                85                  90                  95

Asn Ala Asp Tyr Gly Pro Pro Val Ser Ile Gly Pro Trp Gly Gln Gly
            100                 105                 110

Thr Gln Val Thr Val Ser Ser
        115

<210> SEQ ID NO 115
<211> LENGTH: 122
<212> TYPE: PRT
<213> ORGANISM: artificial sequence
<220> FEATURE:
<223> OTHER INFORMATION: NG17 amino acid sequence

<400> SEQUENCE: 115

Gln Val Lys Leu Glu Glu Ser Gly Gly Gly Trp Val Gln Pro Gly Gly
1               5                   10                  15

Ser Leu Arg Leu Ser Cys Val Val Ser Gly Arg Ile Leu Ser Ile Lys
            20                  25                  30

Ala Met Gly Trp Tyr Arg Gln Ala Pro Gly Lys Gln Arg Glu Tyr Val
        35                  40                  45

Ala Gly Ile Val Ser Ser Gly Asn Thr Asn Tyr Ala Asp Phe Val Lys
    50                  55                  60

Gly Arg Phe Thr Ile Ser Gly Asp Asn Ala Lys Asn Thr Val Phe Leu
65                  70                  75                  80

Gln Met Asn Ser Leu Lys Pro Glu Asp Thr Ala Val Tyr Tyr Cys Asn
                85                  90                  95

Ala Leu Val Val Val Thr Ser Ala Ser Gly Pro Glu Leu Ala Ser Trp
            100                 105                 110

Gly Gln Gly Thr Gln Val Thr Val Ser Ser
        115                 120

<210> SEQ ID NO 116
<211> LENGTH: 122
<212> TYPE: PRT
<213> ORGANISM: artificial sequence
<220> FEATURE:
<223> OTHER INFORMATION: G1-3 amino acid sequence

<400> SEQUENCE: 116

Asp Val Gln Leu Val Asp Ser Gly Gly Leu Ala Gln Ala Gly Gly
1               5                   10                  15

Ser Leu Arg Leu Ser Cys Thr Ala Ser Gly Arg Thr Phe Ser Thr Tyr
            20                  25                  30

Phe Met Ala Trp Phe Arg Gln Pro Pro Gly Lys Gln Arg Glu Leu Val
            35                  40                  45

Ala Tyr Ile Arg Ser Gly Gly Thr Thr Asn Tyr Ala Asp Ser Val Lys
        50                  55                  60

Gly Arg Phe Thr Ile Ser Arg Asp Ile Ala Lys Asn Thr Val Tyr Leu
65                  70                  75                  80

Gln Met Asn Ser Leu Lys Pro Glu Asp Thr Ala Val Tyr Tyr Cys Asn
                85                  90                  95

Ala Asp Tyr Ser Pro Pro Gly Ser Arg Phe Pro Asp Leu Gly Pro Trp
            100                 105                 110

Gly Gln Gly Thr Gln Val Thr Val Ser Ser
        115                 120

<210> SEQ ID NO 117
<211> LENGTH: 121
<212> TYPE: PRT
<213> ORGANISM: artificial sequence
<220> FEATURE:
<223> OTHER INFORMATION: NG18 amino acid sequence

<400> SEQUENCE: 117

Gln Val Lys Leu Glu Glu Ser Gly Gly Gly Leu Val Gln Pro Gly Gly
1               5                   10                  15

Ser Leu Thr Leu Ser Cys Ala Ala Ser Gly Phe Thr Leu Asp Asn Tyr
            20                  25                  30

Ala Ile Ala Trp Phe Arg Gln Ala Pro Gly Arg Glu Arg Glu Trp Val
            35                  40                  45

Ser Ser Thr Gly Ser Asp Gly Asn Leu Tyr Thr Pro Ser Val Arg Gly
        50                  55                  60

Arg Phe Thr Ile Ser Arg Asp Asn Ala Lys Asn Thr Val Tyr Leu Gln
65                  70                  75                  80

Met Asn Ser Leu Lys Pro Glu Asp Thr Ala Val Tyr Tyr Cys Val Ala
                85                  90                  95

Gly Lys Arg Pro Val Ile Thr Thr Trp Ile Ala Leu Asp Ala Trp Gly
            100                 105                 110

Gln Gly Thr Gln Val Thr Val Ser Ser
        115                 120

```
<210> SEQ ID NO 118
<211> LENGTH: 115
<212> TYPE: PRT
<213> ORGANISM: artificial sequence
<220> FEATURE:
<223> OTHER INFORMATION: NG24 amino acid sequence

<400> SEQUENCE: 118
```

Asp Val Gln Leu Val Asp Ser Gly Gly Gly Leu Val Gln Ala Gly Gly
1               5                   10                  15

Ser Leu Arg Leu Ser Cys Ala Ala Ser Gly Thr Phe Ser Ile Asp
            20                  25                  30

Ser Met Arg Trp Phe Arg Arg Ala Pro Gly Lys Glu Arg Glu Phe Val
        35                  40                  45

Ala His Ile Thr Ser Thr Gly Arg Thr Asn Tyr Ala Asp Ala Val Lys
    50                  55                  60

Gly Arg Phe Thr Ile Ser Arg Asp Asn Ala Lys Asn Thr Met Trp Leu
65                  70                  75                  80

Gln Met Asp Asn Leu Lys Pro Asp Asp Thr Ala Val Tyr Tyr Cys Asn
                85                  90                  95

Met Val Thr Thr Pro Tyr Met His Trp Gly Gln Gly Thr Gln Val Thr
            100                 105                 110

Val Ser Ser
        115

```
<210> SEQ ID NO 119
<211> LENGTH: 115
<212> TYPE: PRT
<213> ORGANISM: artificial sequence
<220> FEATURE:
<223> OTHER INFORMATION: NG25 amino acid sequence

<400> SEQUENCE: 119
```

Gln Val Lys Leu Glu Glu Ser Gly Gly Gly Leu Val Gln Ala Gly Gly
1               5                   10                  15

Ser Leu Lys Leu Ser Cys Val Ala Ser Gly Ser Arg Phe Ser Glu Asn
            20                  25                  30

Ala Met Gly Trp Tyr His Gln Ala Pro Asp Lys Gln Arg Thr Leu Val
        35                  40                  45

Ala Ala Ile Thr Ser Ser Arg Ser Thr Leu Tyr Ile Asp Ser Val Lys
    50                  55                  60

Gly Arg Phe Thr Ile Ser Arg Asp Asn Ala Lys Asn Thr Val Tyr Leu
65                  70                  75                  80

Gln Met Ser Asn Leu Lys Pro Glu Asp Thr Gly Val Tyr Tyr Cys Asn
                85                  90                  95

Pro Tyr Pro Ser Pro Asn Ser Tyr Trp Gly Gln Gly Thr Gln Val Thr
            100                 105                 110

Val Ser Ser
        115

```
<210> SEQ ID NO 120
<211> LENGTH: 116
<212> TYPE: PRT
<213> ORGANISM: artificial sequence
<220> FEATURE:
<223> OTHER INFORMATION: NG19 amino acid sequence

<400> SEQUENCE: 120
```

Gln Val Lys Leu Glu Glu Ser Gly Gly Gly Leu Val Gln Pro Gly Gly
1               5                   10                  15

```
Ser Leu Arg Leu Ser Cys Ala Ala Ser Gly Leu Val Phe Ser Ala Asn
            20                  25                  30

Lys Met Gly Trp Tyr Arg Gln Ala Pro Gly Lys Gln Arg Glu Leu Val
            35                  40                  45

Ala Arg Ile Ser Thr Asp Gly Arg Thr Asn Tyr Ala Asp Ser Val Lys
        50                  55                  60

Gly Arg Phe Thr Ile Ser Arg Asp Asn Ala Glu Lys Thr Val Phe Leu
65                      70                  75                  80

Gln Met Asn Ser Leu Asn Pro Asp Asp Thr Ala Val Tyr Tyr Cys Asn
                85                  90                  95

Ala Asn Trp Leu Asp Lys Tyr Asp Tyr Trp Gly Gln Gly Thr Gln Val
            100                 105                 110

Thr Val Ser Ser
        115

<210> SEQ ID NO 121
<211> LENGTH: 120
<212> TYPE: PRT
<213> ORGANISM: artificial sequence
<220> FEATURE:
<223> OTHER INFORMATION: NG26(G21-1) amino acid sequence

<400> SEQUENCE: 121

Gln Val Lys Leu Glu Glu Ser Gly Gly Gly Leu Val Glu Pro Gly Gly
1               5                   10                  15

Ser Leu Arg Leu Ser Cys Val Ala Ser Gly Ser Ile Ser Ser Ala Arg
            20                  25                  30

Ser Met Thr Trp Tyr Arg Gln Ala His Gly Lys Gln Arg Glu Leu Val
            35                  40                  45

Ala Val Ile Thr Ser Gly Gly Ser Thr Met Tyr Ala Asp Ser Val Lys
        50                  55                  60

Gly Arg Phe Thr Ile Ser Arg Asp Ser Ala Lys Asn Thr Val Tyr Leu
65                      70                  75                  80

Gln Met Asn Ser Leu Lys Pro Glu Asp Thr Ala Val Tyr Tyr Cys Asn
                85                  90                  95

Ala Asp Trp Gly Glu Val Gly Phe Val Asn Leu Gly Pro Trp Gly Gln
            100                 105                 110

Gly Thr Gln Val Thr Val Ser Ser
        115                 120

<210> SEQ ID NO 122
<211> LENGTH: 121
<212> TYPE: PRT
<213> ORGANISM: artificial sequence
<220> FEATURE:
<223> OTHER INFORMATION: G18 amino acid sequence

<400> SEQUENCE: 122

Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Ile Phe Gly Phe Asn
            20                  25                  30

Gly Val Ala Trp Phe Arg Gln Ala Pro Gly Lys Gly Arg Glu Leu Val
            35                  40                  45

Ala Val Ile Arg Ser Gly Gly Asn Thr Tyr Ala Asp Ser Val Lys Gly
        50                  55                  60

Arg Phe Thr Ile Ser Arg Asp Asn Ala Lys Asn Thr Val Tyr Leu Gln
```

```
                65                  70                  75                  80
Met Asn Ser Leu Lys Pro Glu Asp Thr Ala Val Tyr Tyr Cys Asn Val
                    85                  90                  95

Asp Tyr Ser Pro Pro Gly Ser Leu Val Pro Asp Leu Gly Pro Trp Gly
                100                 105                 110

Gln Gly Thr Gln Val Thr Val Ser Ser
            115                 120

<210> SEQ ID NO 123
<211> LENGTH: 123
<212> TYPE: PRT
<213> ORGANISM: artificial sequence
<220> FEATURE:
<223> OTHER INFORMATION: G16# amino acid sequence

<400> SEQUENCE: 123

Glu Val Gln Leu Glu Glu Ser Gly Gly Gly Leu Val Gln Pro Gly Gly
1               5                   10                  15

Ser Leu Arg Leu Ser Cys Ala Ala Ser Gly Ser Ile Ala Ser Ile Asn
                20                  25                  30

Ala Met Gly Trp Tyr Arg Gln Ala Pro Gly Lys Gln Arg Glu Leu Val
            35                  40                  45

Ala Ala Ile Thr Arg Gly Gly Ser Thr Asn Tyr Ala Asp Ser Val Lys
        50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Ser Cys Asn
                85                  90                  95

Gly Leu Cys Ser Asp Asp Arg Cys Tyr Gly Asp Ser Leu Phe Ala Pro
                100                 105                 110

Trp Gly Pro Gly Thr Gln Val Thr Val Ser Ser
            115                 120

<210> SEQ ID NO 124
<211> LENGTH: 118
<212> TYPE: PRT
<213> ORGANISM: artificial sequence
<220> FEATURE:
<223> OTHER INFORMATION: G24 amino acid sequence

<400> SEQUENCE: 124

Glu Val Gln Leu Val Glu Ser Gly Gly Gly Leu Val Gln Pro Gly Gly
1               5                   10                  15

Ser Leu Arg Leu Ser Cys Leu Val Ser Gly Arg Gly Val Ser Leu Asp
                20                  25                  30

Ala Val Gly Trp Ser Arg Val Ala Pro Gly Lys Gln Arg Asp Phe Val
            35                  40                  45

Ala Arg Ile Asp Ser Arg Gly Ser Ala Tyr Tyr Ala Asp Ser Val Glu
        50                  55                  60

Gly Arg Phe Thr Ile Ser Arg Asp Asn Ala Lys Asn Thr Val Tyr Leu
65                  70                  75                  80

Gln Val Asp Thr Leu Lys Pro Glu Asp Thr Ala Val Tyr Tyr Cys Phe
                85                  90                  95

Ala Tyr Tyr Gly Ala Gln Ile Ser Phe Gly Pro Trp Gly Gln Gly Thr
                100                 105                 110

Gln Val Thr Val Ser Ser
            115
```

```
<210> SEQ ID NO 125
<211> LENGTH: 115
<212> TYPE: PRT
<213> ORGANISM: artificial sequence
<220> FEATURE:
<223> OTHER INFORMATION: G19 amino acid sequence

<400> SEQUENCE: 125

Asp Val Gln Leu Gln Ala Ser Gly Gly Gly Leu Val Gln Pro Gly Gly
1               5                   10                  15

Ser Leu Arg Leu Ser Cys Val Val Ser Gly Arg Gly Val Asn Leu Asp
            20                  25                  30

Ala Met Gly Trp Ser Arg Val Ala Pro Gly Lys Gln Arg Asp Phe Val
        35                  40                  45

Ala His Ile Asp Asp Arg Gly Thr Ala Tyr Tyr Ala Asp Phe Val Lys
    50                  55                  60

Gly Arg Ser Thr Ile Ser Arg Asp Asn Ala Lys Asn Thr Val Tyr Leu
65                  70                  75                  80

Gln Val Asp Thr Leu Lys Pro Glu Asp Thr Ala Val Tyr Tyr Cys Phe
                85                  90                  95

Ala Trp Gln Gly Ala Glu Thr Tyr Trp Gly Leu Gly Thr Arg Val Thr
            100                 105                 110

Val Ser Ser
        115

<210> SEQ ID NO 126
<211> LENGTH: 120
<212> TYPE: PRT
<213> ORGANISM: artificial sequence
<220> FEATURE:
<223> OTHER INFORMATION: G5-1 amino acid sequence

<400> SEQUENCE: 126

Glu Val Gln Leu Val Glu Ser Gly Gly Gly Leu Val Gln Ala Gly Gly
1               5                   10                  15

Ser Leu Arg Leu Ser Cys Val Ala Ser Gly Ser Ile Phe Ser Val Asn
            20                  25                  30

Ala Val Ala Trp Tyr Arg Gln Ala Pro Gly Lys Gln Arg Glu Leu Val
        35                  40                  45

Ala Tyr Ile Arg Arg Ser Gly Ser Thr Asn Tyr Ala Asp Ser Val Lys
    50                  55                  60

Gly Arg Phe Thr Ile Ser Arg Asp Asn Ala Lys Asn Thr Leu Tyr Leu
65                  70                  75                  80

Gln Met Asn Ser Leu Lys Pro Asp Asp Thr Ala Val Tyr Tyr Cys Asn
                85                  90                  95

Ala Gly Arg Thr Gly Asp Arg Phe Asn Leu Val Ala Tyr Trp Gly Gln
            100                 105                 110

Gly Thr Gln Val Thr Val Ser Ser
        115                 120

<210> SEQ ID NO 127
<211> LENGTH: 123
<212> TYPE: PRT
<213> ORGANISM: artificial sequence
<220> FEATURE:
<223> OTHER INFORMATION: G26 amino acid sequence

<400> SEQUENCE: 127

Glu Val Gln Leu Val Glu Ser Gly Gly Gly Leu Ala Gln Ala Gly Gly
```

-continued

```
1               5                   10                  15
Ser Leu Arg Leu Ser Cys Thr Ala Ser Gly Arg Thr Phe Ser Thr Tyr
            20                  25                  30

Phe Met Ala Trp Phe Arg Gln Pro Pro Gly Lys Glu Arg Glu Tyr Val
            35                  40                  45

Gly Gly Ile Arg Trp Ser Asp Gly Val Pro His Tyr Ala Asp Ser Val
            50                  55                  60

Lys Gly Arg Phe Thr Ile Ser Arg Asp Asn Ala Lys Asn Thr Val Tyr
65                      70                  75                  80

Leu Gln Met Asn Ser Leu Lys Pro Glu Asp Thr Ala Val Tyr Tyr Cys
                    85                  90                  95

Asn Ala Asp Tyr Ser Pro Pro Gly Ser Arg Phe Pro Asp Leu Gly Pro
                    100                 105                 110

Trp Gly Gln Gly Thr Gln Val Thr Val Ser Ser
                    115                 120
```

<210> SEQ ID NO 128
<211> LENGTH: 119
<212> TYPE: PRT
<213> ORGANISM: artificial sequence
<220> FEATURE:
<223> OTHER INFORMATION: G27 amino acid sequence

<400> SEQUENCE: 128

```
Glu Val Gln Leu Gln Ala Ser Gly Gly Gly Leu Val Gln Pro Gly Gly
1               5                   10                  15

Ser Leu Arg Leu Ser Cys Val Ala Ser Gly Ser Ile Phe Ser Ile Lys
            20                  25                  30

Ala Met Ala Trp Tyr Arg Gln Ala Pro Gly Lys Gln Arg Glu Leu Val
            35                  40                  45

Ala Tyr Ile Arg Ser Gly Gly Thr Thr Asn Tyr Ala Asp Ser Val Lys
            50                  55                  60

Gly Arg Phe Thr Ile Ser Arg Asp Ile Ala Lys Asn Thr Val Tyr Leu
65                      70                  75                  80

Gln Met Asn Ser Leu Lys Ser Glu Asp Thr Ala Val Tyr Phe Cys Ala
                    85                  90                  95

Ser Arg Gly Ile Ala Asp Gly Ser Asp Phe Gly Ser Tyr Gly Gln Gly
                    100                 105                 110

Thr Gln Val Thr Val Ser Ser
                    115
```

<210> SEQ ID NO 129
<211> LENGTH: 122
<212> TYPE: PRT
<213> ORGANISM: artificial sequence
<220> FEATURE:
<223> OTHER INFORMATION: G1-2 amino acid sequence

<400> SEQUENCE: 129

```
Glu Val Gln Leu Val Glu Ser Gly Gly Gly Leu Val Gln Ala Gly Ala
1               5                   10                  15

Ser Val Arg Leu Ser Cys Ala Ala Ser Gly Arg Ala Asn Ser Leu Tyr
            20                  25                  30

Ala Met Gly Trp Phe Arg Gln Ala Pro Gly Lys Gln Arg Glu Leu Val
            35                  40                  45

Ala Tyr Ile Arg Ser Gly Gly Thr Thr Asn Tyr Ala Asp Ser Val Lys
            50                  55                  60
```

Gly Arg Phe Thr Ile Ser Arg Asp Ile Ala Lys Asn Thr Val Tyr Leu
65                  70                  75                  80

Gln Met Asn Ser Leu Lys Pro Glu Asp Thr Ala Val Tyr Tyr Cys Asn
                85                  90                  95

Ala Asp Tyr Ser Pro Pro Gly Ser Arg Phe Pro Asp Leu Gly Pro Trp
            100                 105                 110

Gly Gln Gly Thr Gln Val Thr Val Ser Ser
            115                 120

<210> SEQ ID NO 130
<211> LENGTH: 124
<212> TYPE: PRT
<213> ORGANISM: artificial sequence
<220> FEATURE:
<223> OTHER INFORMATION: G28 amino acid sequence

<400> SEQUENCE: 130

Glu Val Gln Leu Val Glu Ser Gly Gly Gly Leu Val Gln Ile Gly Asp
1               5                   10                  15

Ser Val Arg Leu Ser Cys Ile Ala Ser Gly Gly Thr Phe Arg Thr Tyr
            20                  25                  30

Ala Met Gly Trp Phe Arg Gln Ala Pro Gly Ala Glu Arg Glu Phe Val
        35                  40                  45

Ala Ala Ile Ser Arg Arg Gly Asn Lys Thr Asp Tyr Ala Glu Ser Val
    50                  55                  60

Lys Gly Arg Phe Thr Val Ser Arg Asp Asn Ala Glu Asn Thr Val Tyr
65                  70                  75                  80

Leu Gln Met Asn Ser Leu Lys Pro Asp Asp Met Gly Val Tyr Tyr Cys
                85                  90                  95

Ala Ala Ser Ala Arg Asn Phe Ile Gly Thr Gln Pro Leu Asp Tyr Asp
            100                 105                 110

Tyr Trp Gly Gln Gly Thr Gln Val Thr Val Ser Ser
        115                 120

<210> SEQ ID NO 131
<211> LENGTH: 120
<212> TYPE: PRT
<213> ORGANISM: artificial sequence
<220> FEATURE:
<223> OTHER INFORMATION: G29 amino acid sequence

<400> SEQUENCE: 131

Gln Val Lys Leu Glu Glu Ser Gly Gly Gly Met Val Gln Ala Gly Gly
1               5                   10                  15

Ser Leu Arg Leu Ser Cys Val Ala Ser Gly Arg Ser Phe Val Gly Tyr
            20                  25                  30

Phe Met Ala Trp Phe Arg Gln Pro Pro Gly Lys Glu Arg Glu Tyr Val
        35                  40                  45

Gly Gly Ile Arg Trp Ser Asp Gly Val Pro His Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Ser Glu Asp Thr Ala Val Tyr Phe Cys
                85                  90                  95

Ala Ser Arg Gly Ile Ala Asp Gly Ser Asp Phe Gly Ser Tyr Gly Gln
            100                 105                 110

Gly Thr Gln Val Thr Val Ser Ser
        115                 120

<210> SEQ ID NO 132
<211> LENGTH: 122
<212> TYPE: PRT
<213> ORGANISM: artificial sequence
<220> FEATURE:
<223> OTHER INFORMATION: G2-1 amino acid sequence

<400> SEQUENCE: 132

```
Gln Val Lys Leu Val Glu Ser Gly Gly Gly Leu Val Gln Pro Gly Gly
1               5                   10                  15

Ser Leu Arg Leu Ser Cys Ala Ala Ser Gly Ser Ile Phe Ser Ile Asn
            20                  25                  30

Ala Met Gly Trp Tyr Arg Gln Ala Pro Gly Lys Gln Arg Glu Leu Val
        35                  40                  45

Ala Ala Ile Thr Lys Ser Asn Asn Ile Asn Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Asn
                85                  90                  95

Gly Phe Phe Thr Leu Pro Gly Tyr Ser Ser Glu Glu Phe Gly Pro Trp
            100                 105                 110

Gly Gln Gly Thr Gln Val Thr Val Ser Ser
        115                 120
```

<210> SEQ ID NO 133
<211> LENGTH: 360
<212> TYPE: DNA
<213> ORGANISM: Artificial Sequence
<220> FEATURE:
<223> OTHER INFORMATION: G3 nucleotide sequence

<400> SEQUENCE: 133

```
gaggtacagc tggtggaatc tgggggagga ttggcgcagg ctgggggctc tctgagactc      60
tcctgtacag cctctggacg caccttcagt acctatttca tggcctggtt ccgccagcct     120
ccagggaaag agcgtgaata cgtaggcggt attaggtgga gtgatggtgt tccacactat     180
gcagactccg tgaagggccg attcaccatc tccagagaca acgccaagaa cacggtgtat     240
ttgcaaatga acagcctgaa atctgaggac acggccgttt attttgtgc atcacggggt      300
attgcggatg gatctgactt tggttcctac ggccagggga cccaggtcac cgtctcctca     360
```

<210> SEQ ID NO 134
<211> LENGTH: 360
<212> TYPE: DNA
<213> ORGANISM: artificial sequence
<220> FEATURE:
<223> OTHER INFORMATION: G1 nucleotide sequence

<400> SEQUENCE: 134

```
gaggtacagc tggtggaatc tgggggagga ttggcgcagg ctgggggctc tctgagactc      60
tcctgtacag cctctggacg caccttcagt acctatttca tggcctggtt ccgccagcct     120
ccagggaaag agcgtgaata cgtaggcggt attaggtgga gtgatggtgt tccacactat     180
gcagactccg tgaagggccg attcaccatc tccagagaca acgccaagaa cacggtgtat     240
ttgcaaatga acagcctgaa atctgaggac acggccgttt attttgtgc atcacggggt      300
attgcggatg gatctgactt tggttcctac ggccagggga cccaggtcac cgtctcctca     360
```

<210> SEQ ID NO 135
<211> LENGTH: 348
<212> TYPE: DNA
<213> ORGANISM: artificial sequence
<220> FEATURE:
<223> OTHER INFORMATION: NG7 nucleotide sequence

<400> SEQUENCE: 135

| | | | | | |
|---|---|---|---|---|---|
| caggtaaagc | tggaggagtc | tgggggaggc | ttggtgcagc | ctgggggtc | tctaagactc | 60 |
| tcctgtgcag | cctctggact | cgtcttcagt | gccaatacca | tggcctggta | ccgccgggct | 120 |
| ccagggaagc | agcgcgagtt | ggtcgcacgt | attagcactg | acggacgtac | aaactacgcg | 180 |
| gactccgtga | agggccgatt | caccatctcc | agagacaacc | gcgagaagac | ggtgtttctg | 240 |
| caaatgaaca | ggctgaaccc | tgacgacacg | gccgtctatt | actgtaatgc | aaactggctc | 300 |
| agtaaatttg | actactgggg | ccaggggacc | caggtcaccg | tctcctca | | 348 |

<210> SEQ ID NO 136
<211> LENGTH: 357
<212> TYPE: DNA
<213> ORGANISM: artificial sequence
<220> FEATURE:
<223> OTHER INFORMATION: G5 nucleotide sequence

<400> SEQUENCE: 136

| | | | | | |
|---|---|---|---|---|---|
| caggtaaagc | tggaggagtc | tgggggaggc | ttggtgcagg | ctgggggtc | tctgagactc | 60 |
| tcctgtgtag | cctctggaag | catcttcagt | gtcaatgccg | tggcctggta | ccgccaggct | 120 |
| ccagggaaac | agcgcgagtt | ggtcgcatat | atacgtcgta | gtggtagcac | aaactatgca | 180 |
| gactccgtga | agggccgatt | caccatctcc | agagacaacg | ccaagaacac | ggtgtatctg | 240 |
| caaatgaaca | gcctgaaacc | tgaggacaca | gccgtctatt | actgtaatgc | agatttcggt | 300 |
| agcgactatg | tcgtcctcgg | ttcctggggc | caggggaccc | aggtcaccgt | ctcctca | 357 |

<210> SEQ ID NO 137
<211> LENGTH: 360
<212> TYPE: DNA
<213> ORGANISM: artificial sequence
<220> FEATURE:
<223> OTHER INFORMATION: G9 nucleotide sequence

<400> SEQUENCE: 137

| | | | | | |
|---|---|---|---|---|---|
| caggtaaagc | tggaggagtc | tgggggaggc | ttggtgcagg | ctgggggtc | tctgagactc | 60 |
| tcctgtgcag | cctctggaag | catcttcagt | atcaaagcct | tggcctggta | ccgccaggct | 120 |
| ccagggaagc | agcgcgagtt | ggtcgcatat | attactagtg | gtggtaacac | aaactatgca | 180 |
| gactccgtga | ggggccgatt | caccatctcc | agagacaacg | ccaagaacac | ggtatatctg | 240 |
| caaatgaaca | gcctgaaacc | tgaggacaca | gccgtctatt | actgtaatgc | agatttcgga | 300 |
| gaagggacta | tcatatccct | tggaccctgg | ggccagggga | cccaggtcac | cgtctcctca | 360 |

<210> SEQ ID NO 138
<211> LENGTH: 360
<212> TYPE: DNA
<213> ORGANISM: artificial sequence
<220> FEATURE:
<223> OTHER INFORMATION: G7 nucleotide sequence

<400> SEQUENCE: 138

| | | | | | |
|---|---|---|---|---|---|
| caggtaaagc | tggaggagtc | tgggggaggc | ttggtgcagc | ctgggggtc | tctgagactc | 60 |
| tcctgtgcag | cctctggaag | cgaattcagt | atcaatgcca | tggcgtggta | ccgccaggct | 120 |

```
ccagggaagc agcgcgagtt ggtcgcagca cttactagtg gtggtaacac tcactatgcg    180
gactccgtga agggccgatt caccatctcc agagacaacg ccaagaacac gtggtatctg    240
caaatgaaca gcctgaaacc tgaggacacg gccgtctatt actgtaatgc agatttcgga    300
actgcgggtt tggtagtgct gggtccctgg ggccagggga cccaggtcac cgtctcctca    360
```

<210> SEQ ID NO 139
<211> LENGTH: 354
<212> TYPE: DNA
<213> ORGANISM: artificial sequence
<220> FEATURE:
<223> OTHER INFORMATION: G6-2 nucleotide sequence

<400> SEQUENCE: 139

```
caggtaaagc tggaggagtc tggggaggc ttggtgcagc ctgggggtc tctgagactc    60 tcctgtgcag cctctggaag catcgtcagt atcaatgcca tggcctggta ccgccaggct    120
ccagggaagc agcgcgagtt ggtcgcatat attcgtagta atggccgcac aaactatgca    180
gactccgtga agggccgatt caccatttcc agagacaacg ccaagaacac ggtgtatctg    240
caaatgaaca gcctgaaact tgaggacacg gccgtctatt actgtaatgc agactacggg    300
cctccagtat ccattggtcc ttggggccag gggacccagg tcaccgtctc ctca           354
```

<210> SEQ ID NO 140
<211> LENGTH: 354
<212> TYPE: DNA
<213> ORGANISM: artificial sequence
<220> FEATURE:
<223> OTHER INFORMATION: G10 nucleotide sequence

<400> SEQUENCE: 140

```
caggtaaagc tggaggagtc tggggaggc ttggtgcagg ctgggggtc tctgagactc    60 tcctgtgtag tctctggaag tctcctcagt atcaaagcca tggcctggtt ccgccagcct    120
ccagggaagc agcgcgagtt ggtcgcagct gttactagtg gtggaagcac acactattta    180
gactccgtga agggccgatt caccatctcc agagacaacg ccaacacggt gcatctgcaa    240
atgaacagcc tgaaacctga ggacacagct gtctattact gtaatgcaga tttcggtact    300
gactatgtcg acttagggcc ctggggccag gggacccagg tcaccgtctc ctca           354
```

<210> SEQ ID NO 141
<211> LENGTH: 366
<212> TYPE: DNA
<213> ORGANISM: artificial sequence
<220> FEATURE:
<223> OTHER INFORMATION: G2 nucleotide sequence

<400> SEQUENCE: 141

```
caggtaaagc tggaggagtc tggggaggc ttggtgcagc ctgggggtc tctgagactc    60 tcctgtgcag tctctggaag catcttcagt atcaatgcca tggctggta ccgccaggct    120 ccagggaaac agcgcgagtt ggtcgcagct attactaaaa gtaataacat aaactatgca    180
gactccgtga agggccgatt caccatctcc acagacaacg ccaagaacac ggtgtatctg    240
caaatgaaca gcctgaaacc tgaggacacg gccgtctatt actgtaatgg attcttcgct    300
ttgcctgggt acagtagtga agaatttggt ccctggggcc aggggaccca ggtcaccgtc    360
tcctca                                                               366
```

<210> SEQ ID NO 142

<210> SEQ ID NO 142
<211> LENGTH: 360
<212> TYPE: DNA
<213> ORGANISM: artificial sequence
<220> FEATURE:
<223> OTHER INFORMATION: G8 nucleotide sequence

<400> SEQUENCE: 142

| | | | | | |
|---|---|---|---|---|---|
| gaggtacagc | tggtggaatc | tgggggaggc | ttggtgcagc | ctggggggtc | tctgagactc | 60 |
| tcctgtgtag | cctctggaaa | catcttcgat | atgaatcgga | tgggctggta | ccgccagcct | 120 |
| ccagggaagc | agcgcgagtt | ggtcgcagat | attcgtgatg | gcggttctac | aatttattca | 180 |
| gattccgtga | agggccgatt | caccatctcc | agagacaacg | ccaagaacac | gctgtatctg | 240 |
| caaatgaaca | gcctgaaacc | tgacgacaca | gccgtgtatt | attgtaatgc | ggggcggaca | 300 |
| ggggatcgtt | ttaatttggt | ggcgtattgg | ggccagggga | cccaggtcac | cgtctcctca | 360 |

<210> SEQ ID NO 143
<211> LENGTH: 372
<212> TYPE: DNA
<213> ORGANISM: artificial sequence
<220> FEATURE:
<223> OTHER INFORMATION: G17 nucleotide sequence

<400> SEQUENCE: 143

| | | | | | |
|---|---|---|---|---|---|
| gatgtgcagc | tgcaggcgtc | tgggggaggc | ttggtgcagc | acggggctc | tctgagactc | 60 |
| tcctgtgaag | cctctggacg | caccttcagt | ggctatgcca | tggcctggtt | ccgccaggct | 120 |
| ccaggaaagg | aacatgaatt | tgtagcagct | attagctcaa | gtagtaatag | tgccccatac | 180 |
| tatgcaaatt | ccgtgaaggg | ccgattcacc | atctccagag | acaacgccaa | gaacacggtt | 240 |
| tatctacaaa | tgaacaacct | acaaactgag | gacacggccg | tttattactg | tgcagcccgg | 300 |
| tacggtacga | acggtacgt | cgcccgggag | tatgactcgt | ggggccaagg | gacccaggtc | 360 |
| accgtctcct | ca | | | | | 372 |

<210> SEQ ID NO 144
<211> LENGTH: 345
<212> TYPE: DNA
<213> ORGANISM: artificial sequence
<220> FEATURE:
<223> OTHER INFORMATION: G25 nucleotide sequence

<400> SEQUENCE: 144

| | | | | | |
|---|---|---|---|---|---|
| gatgtgcagc | tgcaggcgtc | tgggggaggc | gtcgtgcagg | ctggggggtc | tctgagactc | 60 |
| tcctgtacag | cctctggaag | catccgcagt | atcaatggca | tggctggtc | gcgcgtggct | 120 |
| ccagggaagc | agcgcgactt | cgtcgcacgt | attgatagta | ggggtagcgc | atactatgca | 180 |
| gactccgtag | agggccgatt | caccatctcc | agagacaacg | ccaagaacac | ggtgtatctg | 240 |
| caagtggaca | cgctgaaacc | tgaggacacg | gccgtctatt | attgctttgc | gtggcagggt | 300 |
| gcggaaacat | attggggcct | ggggacccag | gtcaccgtct | cctca | | 345 |

<210> SEQ ID NO 145
<211> LENGTH: 354
<212> TYPE: DNA
<213> ORGANISM: artificial sequence
<220> FEATURE:
<223> OTHER INFORMATION: NG1 nucleotide sequence

<400> SEQUENCE: 145

| | | | | | |
|---|---|---|---|---|---|
| caggtaaagc | tggaggagtc | tgggggaggc | ttggtgcagc | ctggggggtc | tctgcgactc | 60 |
| tcctgtgcag | cctctggaag | catcggcgat | acctatgcca | tggcctggta | ccgccaggct | 120 |

```
ccagggaagc agcgcgactt ggtcgcatat attactaatg gtggtagcac ggactacgca    180
gcctccgtga agggccgatt caccatctcc agagacaacg ccaagaacac ggtctatctg    240
caaatgaaca gcctgaaacc tgaggacacg gccgtctact actgtaatgg agctacccgt    300
ggtgcacagt tagtcttcga ctggggccag gggacccagg tcaccgtctc ctca          354
```

<210> SEQ ID NO 146
<211> LENGTH: 372
<212> TYPE: DNA
<213> ORGANISM: artificial sequence
<220> FEATURE:
<223> OTHER INFORMATION: NG20 nucleotide sequence

<400> SEQUENCE: 146

```
caggtaaagc tggaggagtc tgggggagga ttggtgcagc acgggggctc tctgagactc     60
tcctgtgcag cctctggagg cacgttcagt aactatgcca tggcctggtt ccgccaggct    120
ccaggaaagg agcgtgaatt tgtagcagct attagcgtga gtgctaatag tgccccatac    180
tatgcaaatt ccgtgaaggg ccgattcacc atctccagag acaacgccaa gaacacggtt    240
tatctgcaaa tgaacagcct aaaaactgag gacacggccg tttattactg tgcagcccgg    300
tacggtacga acgatacgt cgcccgggag tatgactcgt ggggccaggg gacccaggtc    360
accgtctcct ca                                                        372
```

<210> SEQ ID NO 147
<211> LENGTH: 344
<212> TYPE: DNA
<213> ORGANISM: artificial sequence
<220> FEATURE:
<223> OTHER INFORMATION: NG21 nucleotide sequence

<400> SEQUENCE: 147

```
caggtaaagc tggaggagtc tgggggaggc ttggtgcagc ctgggggtc tctgcgactc      60 tcctgcgcag cctctggaag tagcgtcagt ctcaatgcca tgggctggtc gcgcgtgcaa    120
ccaggaagta cgcgcgactt cgtcgcacgg attgctgccg atggtagcac tcactatgca    180
gactccgtga gggccggttc accatctccg ggacgccgc caggaacacg gtgtatctac    240
aaatggattc gctgaaaccc gaagacacgg ccgtctatta ctgttttgcg tggctgggta    300
cggacacgta ctggggccag gggacccagg tcaccgtctc ctca                     344
```

<210> SEQ ID NO 148
<211> LENGTH: 342
<212> TYPE: DNA
<213> ORGANISM: artificial sequence
<220> FEATURE:
<223> OTHER INFORMATION: G14 nucleotide sequence

<400> SEQUENCE: 148

```
caggtaaagc tggaggagtc tgggggaggc ttggtgcagg ctgggggtc tctgacactc      60 tcctgtgcag cctctggaag catcggcgat aacaatgcca tgggctggtc ccgcacgcct    120
ccagggaagc agcgcgagtt cgtcgcacgt atagatagtg ggggatcac acgtatgca     180 gactccctga agggccgatt cactgtctcc agagacaccg gcaagaacac ggtgtctctg    240
caaatgaaca gcctgaaagc tgaggacaca ggcgtctatt actgttttgc acatgtcggt    300
ggtactatct ggggccaggg gacccaggtc accgtctcct ca                       342
```

<210> SEQ ID NO 149

```
<211> LENGTH: 372
<212> TYPE: DNA
<213> ORGANISM: artificial sequence
<220> FEATURE:
<223> OTHER INFORMATION: NGS1 nucleotide sequence

<400> SEQUENCE: 149
caggtaaagc tggaggagtc tgggggaggc ttggtgcagc ctggggggtc tctgagactc    60
tcctgtttac cctctggagg catcttcact atcaatagca tgggctggta tcggcaggct   120
ccagggaaac agcgcgagtt ggtcgcaagt atcactggtg gtggtagttc acgttatgca   180
gactccgtga agggccgatt catcatgtcc agagacaacg ccaagaacat ggtgtatctg   240
caaatgaaca gcctgaaacc tgaggacacg gccgtctatt actgtaatac aatccccccg   300
gcccggaccc aaagcgatca tggggagtgg tatgactact ggggccaggg gacccaggtc   360
accgtctcct ca                                                      372

<210> SEQ ID NO 150
<211> LENGTH: 354
<212> TYPE: DNA
<213> ORGANISM: artificial sequence
<220> FEATURE:
<223> OTHER INFORMATION: G12 nucleotide sequence

<400> SEQUENCE: 150
caggtaaagc tggaggagtc tgggggaggc ttggtgcagg ctggagggtc tctgagactc    60
tcctgcgcag cctctagcag catcttcagt atcaatatga gctggtaccg ccaggctcca   120
gggaacgagc gcgagttggt cgcaactatt acacggcatg atagcacaca ctattcagac   180
tccgtgaagg gccgattcac catctccaga gacgacgaca agaacacgat atatctgcaa   240
atgaacagcc tgaaacctga ggacacggcc gtctattact gttctgggtt ttttctggac   300
ggtagtacct ggcacccata ttggggccag gggacccagg tcaccgtctc ctca         354

<210> SEQ ID NO 151
<211> LENGTH: 366
<212> TYPE: DNA
<213> ORGANISM: artificial sequence
<220> FEATURE:
<223> OTHER INFORMATION: G6 nucleotide sequence

<400> SEQUENCE: 151
gaggtacagc tggtggaatc tggggggaggc ttggtgcagc ctggggggtc tctgagactc    60
tcctgtgcag cctctggaag catcgtcagt atcaatgcca tggcctggta ccgccaggct   120
ccagggaagc agcgcgagtt ggtcgcatat attcgtagta atggcagcac aaactatgca   180
gactccgtga agggccgatt caccatttcc agagacaacg ccaagaacac ggtctacctg   240
caaatgaaca gcctgaaact tgaggacacg gccgtctatt attgtaatgg attcttcact   300
ttgcctgggt acagtagtga agaatttggt ccctggggcc aggggaccca ggtcaccgtc   360
tcctca                                                             366

<210> SEQ ID NO 152
<211> LENGTH: 429
<212> TYPE: DNA
<213> ORGANISM: artificial sequence
<220> FEATURE:
<223> OTHER INFORMATION: G22# nucleotide sequence

<400> SEQUENCE: 152
gaggtacagc tggtggaatc tgggggaggc ttggtgcagc ctggagggtc tctgagactc    60
```

```
tcctgtgcag cctctgagag catcttcagt atcaacgcca tgggctggta ccgccaggct    120
ccagggaagc agcgcgagta tgtcgcaggc attactaagg gtgggcgtac aaactatgca    180
gactccgtga agggccgatt caccatctcc agagacgacg ccaagaatac ggtgtatctg    240
caaatgaaca gcctgaaacc tgaagacacg gccgtctatt actgtaatgg tttgtgctca    300
ggcagagagt gttatgggga ctccctttt gccgcctggg gccaggggac ccaggtcacc    360
gtctcctcag gatccgaaca aaaactgatc agcgaagaag atctgaacca tcaccatcac    420
cattagtga                                                            429
```

<210> SEQ ID NO 153
<211> LENGTH: 357
<212> TYPE: DNA
<213> ORGANISM: artificial sequence
<220> FEATURE:
<223> OTHER INFORMATION: G6-1 nucleotide sequence

<400> SEQUENCE: 153

```
gaggtacagc tggtggaatc tggggagggc ttggtgcagc ctggggggtc tctgagactc     60
tcctgtgcag cctctggaag catcgtcagt atcaatgcca tggcctggta ccgccaggct    120
ccagggaagc agcgcgagtt ggtcgcatat attcgtagta atggccgcac aaactatgca    180
gactccgtga agggccgatt caccatttcc agagacaacg ccaagaacac ggtgtatctg    240
caaatgaaca gcctgaaact tgaggacacg gccgtctatt actgttctgg gttttttctg    300
gacggtagta cctggcaccc atattggggc cagggcaccc aggtcaccgt ctcctca       357
```

<210> SEQ ID NO 154
<211> LENGTH: 369
<212> TYPE: DNA
<213> ORGANISM: artificial sequence
<220> FEATURE:
<223> OTHER INFORMATION: G13# nucleotide sequence

<400> SEQUENCE: 154

```
gaggtacagc tggtggaatc tgggggagga ttggcgcagg ctgggggctc tctgagactc     60
tcctgtgcag cctctggatt cactttcgat gattatgcca taggctggtt ccgccaggcc    120
ccagggaagg agcgtgaggg ggtctcatgt attagtagta gtgatggtag cacacactat    180
gcagactccg tgaagggccg attcaccatc tccagagaca tgccaggaa cacggtgact     240 ctgcaaataa acagcctgaa acctgaggat acggccgttt attactgtgc gacccctgg     300 gtgacctatt gccccgagaa ccttctgttt agttactggg gccaggggac ccaggtcacc    360
gtctcctca                                                            369
```

<210> SEQ ID NO 155
<211> LENGTH: 369
<212> TYPE: DNA
<213> ORGANISM: artificial sequence
<220> FEATURE:
<223> OTHER INFORMATION: G13-2# nucleotide sequence

<400> SEQUENCE: 155

```
caggtaaagc tggaggagtc tgggggaggc ttggtgcagc ctggggggtc tctgagactc     60
tcctgtgcag cctctggatt cactttcgat gattatgcca taggctggtt ccgccaggcc    120
ccagggaagg agcgcgaggg ggtctcatgt attacgagta gtgatggtag cacatactat    180
gcagactctg tgaagggccg attcaccatc tccagagaca atgccaacaa cacggtgcat    240
```

```
ctgcaaataa gcaacctaaa acctgaggat acggccgttt attactgtgc gacccctgg    300 gtgacctact gccccgagaa ccttctgttt agttactggg ccaggggac ccaggtcacc    360 gtctcctca                                                           369
```

<210> SEQ ID NO 156
<211> LENGTH: 360
<212> TYPE: DNA
<213> ORGANISM: artificial sequence
<220> FEATURE:
<223> OTHER INFORMATION: G31 nucleotide sequence

<400> SEQUENCE: 156

```
gaggtacagc tggtggaatc tggggaggc ttggtgcagg ctggggggtc tctgacactc    60
tcctgtgcag tctctggaag cagcttcagt atcaaggcca tggctggta ccgcctggct    120 ccagggaagc agcgcgagtt ggtcgcagca attactagtg gtggtagcac gaactatgcg    180
gactccgtga agggccgatt caccatctcc agagacagcg ccaagaacac ggtgtatctg    240
caaatgaaca gcctgaaacc tgaggacaca gccgtctatt actgtaatgg tttttttcgag    300 tatagggggtc ttgaacaatt gggcccctgg ggccagggga cccaggtcac cgtctcctca    360
```

<210> SEQ ID NO 157
<211> LENGTH: 360
<212> TYPE: DNA
<213> ORGANISM: artificial sequence
<220> FEATURE:
<223> OTHER INFORMATION: G4 nucleotide sequence

<400> SEQUENCE: 157

```
gatgtgcagc tgcaggcgtc tggggaggc ttggtgcagc ctggggggtc tctgagactc    60
tcctgtgcag cctctggaag catcgtcggt atccgtgcca tgacgtggta ccgccaggct    120
ccagggaagc agcgcgagtt ggtcgcagtt cttactagtg ctggtaaacc tatgtatgcc    180
gactccgtga agggccgatt caccatctcc agagacaacg ccaagaacac ggtatatctg    240
caaatgaaca gcctgaaacc tgaggacacg gccgtctatt actgtaacgc agatttcggg    300
actccgggtt cagtagtact gggtccttgg ggccagggga cccaggtcac cgtctcctca    360
```

<210> SEQ ID NO 158
<211> LENGTH: 366
<212> TYPE: DNA
<213> ORGANISM: artificial sequence
<220> FEATURE:
<223> OTHER INFORMATION: NG2 nucleotide sequence

<400> SEQUENCE: 158

```
caggtaaagc tggaggagtc tgggggaggc ttggtgcagc ctggggggtc tctgagactc    60
tcctgtgcag cctctggaag catcctcagt atcgaggcca tgggctggta ccgccagact    120
cttgggaagc agcgcgaatt ggtcgcagct attactagtg gtgatagcac aaactatgca    180
gacttcgtga agggccgatt caccatctcc agagacaagg ccaagaacat ggtgtatctg    240
caaatgaaca gcctgaaacc tgaggacacg gccgtctatt tctgtaatgc cctaatggta    300
gttagggctg gctcgaatcc cgaaattggt ccctggggcc aggggaccca ggtcaccgtc    360
tcctca                                                              366
```

<210> SEQ ID NO 159
<211> LENGTH: 369
<212> TYPE: DNA
<213> ORGANISM: artificial sequence
<220> FEATURE:
<223> OTHER INFORMATION: G13-3# nucleotide sequence

<400> SEQUENCE: 159

```
caggtaaagc tggaggagtc tgggggaggc ttggtgcagg ctgggggtc tctgagactc      60
tcctgtgcag cctctggatt cactttcgat gattatgcca taggctggtt ccgccaggcc    120
ccagggaagg agcgtgaggg ggtctcatgt attagtagta gtgatggtag cacatactat    180
gcagactccg tgaagggccg attcaccatc tccagagaca atgccaagaa cacgtgtat    240
ctgcaaataa acagcctgaa acctgaggat acggccgttt attactgtgc gacccctgg    300
gtgacctact gccccgagaa ccttctgttt agttactggg gccaggggac ccaggtcacc    360
gtctcctca                                                           369
```

<210> SEQ ID NO 160
<211> LENGTH: 345
<212> TYPE: DNA
<213> ORGANISM: artificial sequence
<220> FEATURE:
<223> OTHER INFORMATION: G20 nucleotide sequence

<400> SEQUENCE: 160

```
gaggtacagc tggtggaatc tgggggagga ttggtgcagc ctgggggtc tctgagactg      60
tcctgtgtag tctctgcaag gggcgtcagt ctcgatgccg tgggctggtc gcgcgtggct    120
ccagggaagc agcgcgactt cgtcgcacgt attgatcgaa ggggtagtac atactatgca    180
gtgtccgtag agggccgatc caccatctcc agagacaacg ccaagaacac ggtgtatctg    240
caactggaca cgctgaaacc tgaggacacg gccgtctatt attgttttgc atggcaggt    300
gcggaaacac attggggcct ggggacccag gtcaccgtct cctca                   345
```

<210> SEQ ID NO 161
<211> LENGTH: 345
<212> TYPE: DNA
<213> ORGANISM: artificial sequence
<220> FEATURE:
<223> OTHER INFORMATION: NG3 nucleotide sequence

<400> SEQUENCE: 161

```
caggtaaagc tggaggagtc tgggggaggc ttggtgcagg ctgggggtc tctgaccctc      60
tcctgtgtag cctctggaag ccacttcagt ttcaatgaca tgggctggta tcgccaggat    120
ccgtggaagg ggcgcgactt ggtcgcggct attactagta gtcgtaacac actttatgta    180
gactccgtga agggccggtt caccatctcc agagacgacg ccaagaacac ggtgtatcta    240
caaatgaaca acctgaaacc tgaggacaca gccgtctatt actgtaaccc gtacccttcc    300
ccaaataact actggggcca ggggacccag gtcaccgtct cctca                   345
```

<210> SEQ ID NO 162
<211> LENGTH: 348
<212> TYPE: DNA
<213> ORGANISM: artificial sequence
<220> FEATURE:
<223> OTHER INFORMATION: NG4 nucleotide sequence

<400> SEQUENCE: 162

```
caggtaaagc tggaggagtc tgggggaggc ttggtgcagc ctgggggtc tctgagactc      60
tcctgtgcag cctctggaag ccccttcacg atcaatgcca tggctggta ccgccaggct     120
ccagggaagc agcgcgagtt ggtcgcagca attactcgta gtggtaagac gaactatgca    180
```

```
gactccgtga agggccgatt caccatctcc ggagacaacg ccctgaccac ggtgtatctg      240
caaatgaaca acctgcaacc tgaagacacg gccgtctatt actgtaatgg gttctacggg      300
tctgaatttg ggccctgggg ccaggggacc caggtcaccg tctcctca                   348

<210> SEQ ID NO 163
<211> LENGTH: 372
<212> TYPE: DNA
<213> ORGANISM: artificial sequence
<220> FEATURE:
<223> OTHER INFORMATION: NG5 nucleotide sequence

<400> SEQUENCE: 163
caggtaaagc tggaggagtc tgggggagga ttggtccagg ctgggggctc tgcgacgctc       60
tcctgttcag cccctggaga caccttaagt agatacgccg tgggctggtt ccgccagggg      120
ccagggcagg agcgtgattt tgtagcatcc attacctgga gtggtgatta cacatactat      180
aaagactccg tgaagggccg attcaccatc tccagagaca gtgtcaacaa catggtgtat      240
ctgcgaatga acagcctgaa acctgaggac acggccctgt attactgtgc agccgataag      300 agttcctta gactccgagg ccctggatta tatgactaca ggggccaggg gacccaggtc      360
accgtctcct ca                                                         372

<210> SEQ ID NO 164
<211> LENGTH: 369
<212> TYPE: DNA
<213> ORGANISM: artificial sequence
<220> FEATURE:
<223> OTHER INFORMATION: NG6# nucleotide sequence

<400> SEQUENCE: 164
caggtaaagc tggaggagtc tgggggaggc ttggtgcagc ctgggggtc tctgagactc        60 tcctgtgcag cctctggatt cactttcgat tattatgcca taggctggtt ccgccaggcc      120
ccagggaagg agcgcgaggg ggtctcatgt attagtagta gggatggtac acccactat      180 gcagactccg tgaagggccg attcaccatc tccagagaca atgccaagaa cacggtgtat      240
ctgcaaatag acagcctgaa acctgaggat acggccgttt attactgtgc gacccctgg      300 gtgacctact gccccgagaa ccttctgttt agttactggg ccaggggac ccaggtcacc      360 gtctcctca                                                             369

<210> SEQ ID NO 165
<211> LENGTH: 375
<212> TYPE: DNA
<213> ORGANISM: artificial sequence
<220> FEATURE:
<223> OTHER INFORMATION: NG8 nucleotide sequence

<400> SEQUENCE: 165
caggtaaagc tggaggagtc tgggggaggc ttcgtacagc ctgggggtc actgagactc        60 tcctgtgcag cctcgggatt cagtttgcat tattatgcca taggctggtt ccgccaggcc      120
ccagggaagg agcgcgagtg ggtctctgcc attagtaata ttgatgatga cacatactat      180
gaagactccg tgaagggccg attcaccatc tccagagaca acgccaagaa cacggcgtat      240
ctgcaaatga caacctgaa acctgaggac acggccgttt attactgtgc agcagataag      300
gatgtagtgg tagtgcgtac gggtctcagc gagtctgact attggggcca ggggacccag      360
gtcaccgtct cctca                                                       375
```

<210> SEQ ID NO 166
<211> LENGTH: 360
<212> TYPE: DNA
<213> ORGANISM: artificial sequence
<220> FEATURE:
<223> OTHER INFORMATION: NG9 nucleotide sequence

<400> SEQUENCE: 166

```
caggtaaagc tggaggagtc tgggggaggc ttggtgcagg ctgggggtc tctgagactc      60
tcctgtgcag cctctggaag catcttcggt atcaatgcca tggcctggta ccgccaggct    120
ccagggaagc agcgcgaact ggtcgcagtt attaccagtg gtggacgcac aatgtatgca    180
gagtccgtga agggccgatt cgccatctcc agagacgtcg ccaagaacac ggtgtatctg    240
caaatgaaca gcctgaaacc tgaagacaca gccgtctatt actgtaatgg agactggggg    300
tcggagggta gggtggacct tggaccctgg ggccagggga cccaggtcac cgtctcctca    360
```

<210> SEQ ID NO 167
<211> LENGTH: 387
<212> TYPE: DNA
<213> ORGANISM: artificial sequence
<220> FEATURE:
<223> OTHER INFORMATION: NG10 nucleotide sequence

<400> SEQUENCE: 167

```
caggtaaagc tggaggagtc tgggggaggc ttggtgcagc ctggggggac gctgagactc     60
tcctgtgccg cctcgggaag cattcgcagt atcggcgaca tggagtggta ccgccaggct    120
ccaggacagc agcgcgagtt ggtcgcaagt attagtgctg gccctgagat gcgtagtgct    180
ggtaccccaa cttatgcaaa gtccgtggag ggccgattca ccatctccag agacaacatc    240
aagaacatga tgtggctgca aatgaacagc ctgagacctg aagacacggc cgtctattcc    300
tgtaatgccg acgttctgac gtactataat ggtagatact cccgagatgt ctactggggc    360
caggggaccc aggtcaccgt ctcctca                                         387
```

<210> SEQ ID NO 168
<211> LENGTH: 354
<212> TYPE: DNA
<213> ORGANISM: artificial sequence
<220> FEATURE:
<223> OTHER INFORMATION: G12-1 nucleotide sequence

<400> SEQUENCE: 168

```
caggtaaagc tggaggagtc tgggggaggc ttggtgcagg ctgggggtc tctgagactc      60
tcctgcgcag cctctagcag catcttcagt atcaatatga gctggtaccg ccaggctcca    120
gggaacgagc gcgagttggt cgcaactatt acacgacatg atagtacaca ctattcagac    180
tccgtgaagg gccgattcgc catctccaga gacgacgaca gaacacgat atatctgcaa    240
atgaacagcc tgaaacctga ggacacggcc gtctattact gttctggatt ttttctggac    300
ggtagtacct ggcggccata ttggggccag gggacccagg tcaccgtctc ctca           354
```

<210> SEQ ID NO 169
<211> LENGTH: 372
<212> TYPE: DNA
<213> ORGANISM: artificial sequence
<220> FEATURE:
<223> OTHER INFORMATION: G17-1 nucleotide sequence

<400> SEQUENCE: 169

```
gatgtgcagc tgcaggcgtc tgggggaggc ttggtgcagc ctggggggtc tctgagactc     60
```

```
tcctgtgcag cctctggacg caccctcagt ggctatgccg tggcctggtt ccgccaggct    120
ccaggaaagg agcgtgagtt tgtagcagcc attagctcga gtgataatag tagcccatat    180
tatgcaaatg tcgtgaaggg tcgattcacc atctccagag acaacgccaa gaacacggtt    240
tatctgcaaa tgaacagcct gcaaactgag gacacggccc tttattactg tgcagcccgg    300
tacggtacga aacggtacgt cgcccgggag tatgactcgt ggggtcaggg gacccaggtc    360
accgtctcct ca                                                        372

<210> SEQ ID NO 170
<211> LENGTH: 366
<212> TYPE: DNA
<213> ORGANISM: artificial sequence
<220> FEATURE:
<223> OTHER INFORMATION: NG11 nucleotide sequence

<400> SEQUENCE: 170
caggtaaagc tggaggagtc tgggggaggc ttggtgcagc ctgggggtc tctgagactc       60 tcctgtgcag cctctagaag catcttcagt atcaatgcca tggcctggta ccgccaggct    120
ccagggaagc agcgcgagtt ggtcgcatat attcgtagta gtggtaccac aatgtatgcg    180
gattccgtga agggccgatt caccatctcc agagacaacg ccaagaacac ggtgtatctg    240
caaatgaaca gcctgaaacc tgaggacacg gccgtctatt attgtaacgg agattactcc    300
ccgcccggca gcacgtaccc tgacttaggt ccctggggcc agggaccca ggtcaccgtc    360 tcctca                                                                366

<210> SEQ ID NO 171
<211> LENGTH: 795
<212> TYPE: DNA
<213> ORGANISM: artificial sequence
<220> FEATURE:
<223> OTHER INFORMATION: G15(bi) nucleotide sequence

<400> SEQUENCE: 171
gaggtgcagc tgcaggcgtc tggggaggc ttggtgcagc ctgggggtc tctgagactc        60 tcctgtgcag cctctggatt cactttcgat gattatgcca taggctggtt ccgccaggcc    120
ccagggaagg agcgcgaggg ggtctcatgt attacgagta gtgatggtag cacatactat    180
gcagactctg tgaagggccg attcaccatc tctagagaca tgccaacaa cacggtgcat    240 ctgcaaataa gcaacctaaa acctgaggat acggccgttt attactgtgc gacccctgg    300 gtgaactact gccccgagaa ccttctgttt agttactggg gccaggggac ccaggtcacc    360
gtctcctcac aggcccaggt acagctggtg aatctgggg gaggattggc gcaggctggg    420
ggctctctga gactcctctg tacagcctct ggacgcacct tcagtaccta tttcatggcc    480
tggttccgcc agcctccagg gaaagagcgt gaatacgtag gcggtattag gtggagtgat    540
ggtgttccac actatacaga ctccgtgaag ggccgattca ccatctccag agacaacgcc    600
aagaacacgg tgtatttgca aatgaacagc ctgaaatctg aggacacggc cgtttatttt    660
tgtgcatcac ggggtattgc ggatggatct gactttggtt cctacggcca ggggacccag    720
gtcaccgtct cctcaggatc cgaacaaaaa ctgatcagcg aagaagatct gaaccatcac    780
catcaccatt agtga                                                      795

<210> SEQ ID NO 172
<211> LENGTH: 348
<212> TYPE: DNA
<213> ORGANISM: artificial sequence
```

```
<220> FEATURE:
<223> OTHER INFORMATION: G11 nucleotide sequence

<400> SEQUENCE: 172
caggtaaagc tggaggagtc tgggggaggc ttggtgcagg ctgggggtc tctgagactc     60 tcctgtggag catctggaat tattttagt gccactacca tggcctggta ccgccaggct    120
ccagggaagc agcgcgagtt ggtcgcactg attactagtg attggcacac aaagtatgca   180
gactccgtga aggaccgatt ctccatttcc agagacaacg ccaagagcac ggtgcacctg   240
caaatgaaca gcctgagatc tgaagacaca gcagtctatt tttgttatgc ccgccaagcc   300
ttcagtgagc tcgttggggg ccaggggacc caggtcaccg tctcctca                348

<210> SEQ ID NO 173
<211> LENGTH: 345
<212> TYPE: DNA
<213> ORGANISM: artificial sequence
<220> FEATURE:
<223> OTHER INFORMATION: NG12 nucleotide sequence

<400> SEQUENCE: 173
caggtacagc tggtggattc tgggggaggc ttggtgcagc ctgggggtc tctgagattg     60 tcctgtgcag cctctggaag cagcggcaga atcgatgcca tgggctggtc gcgcgtggct   120
ccagggaagc agcgcgactt cgtcgcacgt cttggcagta atggattcac acagtatgac   180
atctccgtgg agggccgatt caccatctcc ggggacgtcg ccaagaatac gatatatctg   240
caaatggaca cgctgaaacc tgaggacacg gccgtctatt actgttttgc gtggctgggg   300
caagataccg tgtggggcca ggggacccag gtcaccgtct cctca                   345

<210> SEQ ID NO 174
<211> LENGTH: 372
<212> TYPE: DNA
<213> ORGANISM: artificial sequence
<220> FEATURE:
<223> OTHER INFORMATION: NG14 nucleotide sequence

<400> SEQUENCE: 174
caggtacagc tggtggattc tgggggagga ttggtaaagg ctggggcatc tctgagactc     60
tcctgtgcag cctctggaga cgccttattt aactacgcca tgggctggtt tcgccagggg   120
ccagggaagg agcgtgactt tgtagcatct gttaccagga gtggtgataa tacatactat   180
aaagactccg cgaagggccg attcaccatc tccagagacg acgccaagaa cacggtatat   240
ctgcaaatga acagcctgaa acctgaggac acggccgttt atttctgtgc agcagataag   300
agttccttta ggctccgagg ccctggagta tatgactaca ggggccaggg gacccaggtc   360
accgtctcct ca                                                       372

<210> SEQ ID NO 175
<211> LENGTH: 378
<212> TYPE: DNA
<213> ORGANISM: artificial sequence
<220> FEATURE:
<223> OTHER INFORMATION: NG13 nucleotide sequence

<400> SEQUENCE: 175
caggtacagc tggtggattc tgggggaggc ttggtgcagg ctgggggtc tctgagactc     60 tcctgtgcag tctctggaag cgacggccga gtcatgctca tggctggta ccgccaggct   120 ccagggcagc agcgcgacct ggtcgcatct attactagtg cagattacac aacctatgca   180
```

```
gaatccgtcg agggccgatt caccatctcc acagacaaca acaagaacac agtgtatcta    240
caaatgaaca gcctgaagcc tgaagacaca gccgtctatt tttgtaaagt aattgcggcg    300
acggtctggg gccaggagac ccaggtcagg cagggtttga cattctgggg ccaggggacc    360
caggtcaccg tctcctca                                                  378

<210> SEQ ID NO 176
<211> LENGTH: 360
<212> TYPE: DNA
<213> ORGANISM: artificial sequence
<220> FEATURE:
<223> OTHER INFORMATION: G21 nucleotide sequence

<400> SEQUENCE: 176
gaggtacagc tggtggaatc tggggaggc ttggtgcagc ctgggggtc tctgagactc       60 tcctgtgtag cctctggaag catctccagt gccagatcca tgacctggta ccgccaggct    120
ctagggaagc agcgcgagtt ggtcgcagtg attatgggtg cggtagcac gatgtatgca     180 gactccgtga agggccgatt caccatctcc agagacaacg ccaagaacac ggtgtatcta    240
caaatgaaca gcctgaaacc tgaggacacg gccgtctatt attgtaatgc agactggggg    300
ggagtcgggt ttccgaactt aggtccctgg ggccagggga cccaggtcac cgtctcctca    360

<210> SEQ ID NO 177
<211> LENGTH: 372
<212> TYPE: DNA
<213> ORGANISM: artificial sequence
<220> FEATURE:
<223> OTHER INFORMATION: NG23 nucleotide sequence

<400> SEQUENCE: 177
gatgtgcagc tgcaggcgtc tggggagga ttggtgcaaa ttggggactc tgtgagactc      60
tcctgtatag cctctggagg caccttcaga acttatgcta tcggttggtt ccgccaggct    120
ccaggggctg agcgtgaatt tgtagctgcc attagccggc gcggtaataa gacagattat    180
gcagagtccg tgaagggccg attcacagtc tccagagaca acgccgagaa tacggtgtat    240
ttgcaaatga acagcctgaa acctgatgac atgggcgttt attactgtgc agcgtcggcg    300
cgtaatttca tcggcaccca gccacttgat tatgactact ggggccaggg gacccaggtc    360
accgtctcct ca                                                        372

<210> SEQ ID NO 178
<211> LENGTH: 366
<212> TYPE: DNA
<213> ORGANISM: artificial sequence
<220> FEATURE:
<223> OTHER INFORMATION: NG15 nucleotide sequence

<400> SEQUENCE: 178
caggtaaagc tggaggagtc tggggagga ttggtacagg ctgggggctc tctgagactc      60
tcctgtgcag cctctggatg gaaccttggt aattatgcct gggctggtt ccgccaggct    120 ccagggaagg agcgtgagtt tgtagcagct atcgactggc gtcatagttc atactatgca    180
gactccgtga agggccgatt caccatctcc agagacaaca ccaagaacat ggtgtatctg    240
caaatgagca gcctgaaact tgaggacacg cgcctttatt actgtgcagc atcaagccta    300
ttccctagta gtgctccccg tcagtatgac tactggggcc aggggaccca ggtcaccgtc    360
tcctca                                                               366
```

-continued

```
<210> SEQ ID NO 179
<211> LENGTH: 369
<212> TYPE: DNA
<213> ORGANISM: artificial sequence
<220> FEATURE:
<223> OTHER INFORMATION: NG16 nucleotide sequence

<400> SEQUENCE: 179
caggtacagc tggtggattc tgggggagga ttggtgcagg ctgggggctc tctgagactc      60
tcctgtgtag cctctggacg caccttcagt aattatgcca tgggctggta ccgccgacgt     120
ccagggctgg agcgtgaatt tgtagcagct attgttggga gtggtgatag cacaaggtat     180
gcagactccg tgaagggccg attcaccatc tccagagaca cgccaagaa cacggtgtat      240 ctgcaaatga acacgctgaa acctgaggac acggccgttt attactgtgc gtcatcctcc     300
gacccgcggg tttatatagc aagtactctc gattactggg gccaggggac ccaggtcacc     360
gtctcctca                                                             369

<210> SEQ ID NO 180
<211> LENGTH: 357
<212> TYPE: DNA
<213> ORGANISM: artificial sequence
<220> FEATURE:
<223> OTHER INFORMATION: G23 nucleotide sequence

<400> SEQUENCE: 180
caggtacagc tggtggaatc tgggggagga ttggtgcagg ctgggggctc tctgagactc      60
tcctgtgcag cctctggacg caccttcagt atgtttatca tgggctggtt ccgccaggct     120
ccagggaagg agcgtgaatt agtagcagct attagccgga atagtaatct cacatactat     180
tttcagtccg tgaaaggccg attcaccatc tccagagaca cgccaagaa cacggtgtat      240 ttgcaaatga acagcctgaa acttgaggac acggccgtct attactgtaa tgcagactac     300
gggcctccag tatccattgg tccttggggc caggggaccc aggtcaccgt ctcctca       357

<210> SEQ ID NO 181
<211> LENGTH: 366
<212> TYPE: DNA
<213> ORGANISM: artificial sequence
<220> FEATURE:
<223> OTHER INFORMATION: NG17 nucleotide sequence

<400> SEQUENCE: 181
caggtaaagc tggaggagtc tgggggaggc tgggtgcagc ctgggggtc tctgagactc       60 tcctgtgtag tctctggaag gatcctcagt atcaaggcca tgggctggta ccgccaggct     120
cctgggaagc agcgcgagta cgtcgcaggt attgttagca gtggtaatac aaactatgca     180
gacttcgtga agggccgatt caccatctcc ggagacaacg ccaagaacac ggtgtttctg     240
caaatgaaca gcctgaaacc tgaagacacg gccgtctatt actgtaatgc cctagtggtc     300
gttactagtg cctcgggtcc cgagttggct tcctggggcc aggggaccca ggtcaccgtc     360
tcctca                                                                 366

<210> SEQ ID NO 182
<211> LENGTH: 366
<212> TYPE: DNA
<213> ORGANISM: artificial sequence
<220> FEATURE:
<223> OTHER INFORMATION: G1-3 nucleotide sequence

<400> SEQUENCE: 182
```

| | |
|---|---|
| gatgtacagc tggtggattc tggggggagga ttggcgcagg ctgggggctc tctgagactc | 60 |
| tcctgtacag cctctggacg caccttcagt acctatttca tggcctggtt ccgccagcct | 120 |
| ccagggaagc agcgcgagtt ggtcgcatac attcgtagtg gtggtacgac aaactatgca | 180 |
| gactccgtga agggccgatt caccatctcc agagacatcg ccaagaacac ggtgtatctg | 240 |
| caaatgaaca gcctgaaacc tgaggacacg gccgtctatt actgcaatgc agattactcc | 300 |
| ccgcccggca gccggttccc tgacttaggt ccctggggcc aggggaccca ggtcaccgtc | 360 |
| tcctca | 366 |

<210> SEQ ID NO 183
<211> LENGTH: 363
<212> TYPE: DNA
<213> ORGANISM: artificial sequence
<220> FEATURE:
<223> OTHER INFORMATION: NG18 nucleotide sequence

<400> SEQUENCE: 183

| | |
|---|---|
| caggtaaagc tggaggagtc tgggggaggc ttggtgcagc ctggggggtc tctgacactc | 60 |
| tcctgcgcag cctctggatt caccttggat aattatgcca tagcgtggtt ccgccaggcc | 120 |
| ccagggaggg agcgcgagtg ggtctcatca actggtagtg atggtaactt atatacaccg | 180 |
| tccgtgaggg gccgattcac catttccaga caacgcca agaacacggt gtatctgcaa | 240 |
| atgaacagct gaaacctga ggacacggcc gtttattatt gtgtagcagg aagagaccg | 300 |
| gtaattacta catggattgc tttggacgca tggggccagg gacccaggt caccgtctcc | 360 |
| tca | 363 |

<210> SEQ ID NO 184
<211> LENGTH: 345
<212> TYPE: DNA
<213> ORGANISM: artificial sequence
<220> FEATURE:
<223> OTHER INFORMATION: NG24 nucleotide sequence

<400> SEQUENCE: 184

| | |
|---|---|
| gatgtacagc tggtggattc tgggggaggc ttggtgcagg ctgggggtc tctgagactc | 60 |
| tcctgtgcag cctctggaac attctccagt atcgattcca tgcgctggtt ccggcgggct | 120 |
| ccaggaaagg agcgcgaatt tgtcgcacat attactagca cgggtaggac aaactatgca | 180 |
| gacgccgtga agggccgatt taccatctct agagacaacg ccaagaacac gatgtggctg | 240 |
| caaatggaca acctgaaacc tgacgacacg gccgtctatt attgcaatat ggtgacgact | 300 |
| ccttatatgc actggggcca ggggacccag gtcaccgtct cctca | 345 |

<210> SEQ ID NO 185
<211> LENGTH: 345
<212> TYPE: DNA
<213> ORGANISM: artificial sequence
<220> FEATURE:
<223> OTHER INFORMATION: NG25 nucleotide sequence

<400> SEQUENCE: 185

| | |
|---|---|
| caggtaaagc tggaggagtc tgggggaggc ttggtgcagg ctgggggtc tctgaaactc | 60 |
| tcctgtgtag cctctggaag ccgcttcagt gaaaatgcca tgggctggta tcaccaggct | 120 |
| ccagacaaac agcgcacctt ggtcgcagct attactagta gtcgtagcac tctttatata | 180 |
| gactccgtga agggccgctt caccatctcc agagacaacg ccaagaacac ggtatatctg | 240 |
| caaatgagca acctgaaacc tgaggacacc ggcgtctatt actgtaaccc gtaccctcc | 300 | ccaaattcct actggggcca ggggacccag gtcaccgtct cctca        345

<210> SEQ ID NO 186
<211> LENGTH: 348
<212> TYPE: DNA
<213> ORGANISM: artificial sequence
<220> FEATURE:
<223> OTHER INFORMATION: NG19 nucleotide sequence

<400> SEQUENCE: 186
caggtaaagc tggaggagtc tggggaggc ttggtgcagc ctgggggtc tctaagactc        60 tcctgtgcag cctctggact cgtcttcagt gccaataaga tgggctggta ccgccaggct      120
ccagggaagc agcgcgagtt ggtcgcacgt attagcactg acggacgtac aaactatgcg      180
gactccgtga agggccgatt caccatctcc agagacaacg ccgagaagac ggtgtttctg      240
caaatgaaca gcctgaatcc tgacgacacg gccgtctatt actgtaatgc aaactggctc      300
gataaatatg actactgggg ccaggggacc caggtcaccg tctcctca                   348

<210> SEQ ID NO 187
<211> LENGTH: 360
<212> TYPE: DNA
<213> ORGANISM: artificial sequence
<220> FEATURE:
<223> OTHER INFORMATION: NG26(G21-1) nucleotide sequence

<400> SEQUENCE: 187
caggtaaagc tggaggagtc tggggaggc ttggtggagc ctgggggtc tctgagactc        60 tcctgtgtgg cctctggaag catctccagt gccagatcca tgacctggta ccgccaggct     120
cacgggaagc agcgcgagtt ggtcgcagtt attactagtg gcggtagcac aatgtatgca     180
gactccgtga agggccgatt caccatctcc agagacagcg ccaagaacac ggtgtatcta     240
caaatgaaca gcctgaaacc tgaggacacg gccgtctatt attgtaatgc agactggggg     300
gaagtcgggt ttgtgaactt aggtccctgg ggccagggga cccaggtcac cgtctcctca     360

<210> SEQ ID NO 188
<211> LENGTH: 366
<212> TYPE: DNA
<213> ORGANISM: artificial sequence
<220> FEATURE:
<223> OTHER INFORMATION: G18 nucleotide sequence

<400> SEQUENCE: 188
gaggtacagc tggtggaatc tggggaggc ttggtgcagc ctgggggtc tctgagactc        60 tcctgtgcag cctctggaag catcttcggt ttcaatggcg tggcctggtt ccgccaggct     120
ccagggaagc agcgcgagtt ggtcgcagtt attcgtagtg gtggtaacac gctctatgca     180
gactccgtga agggccgatt caccatctcc agagacaacg ccaagaacac ggtgtatctg     240
caaatgaaca gcctgaaacc tgaggacacg gccgtctatt actgtaatgt agattactcc     300
ccgcccggta gtctggttcc tgacttaggt ccctgggggcc aggggaccca ggtcaccgtc    360
tcctca                                                                366

<210> SEQ ID NO 189
<211> LENGTH: 369
<212> TYPE: DNA
<213> ORGANISM: artificial sequence
<220> FEATURE:
<223> OTHER INFORMATION: G16# nucleotide sequence

<400> SEQUENCE: 189

```
gaggtacagc tggaggagtc tgggggaggc ttggtgcagc ctgggggtc tctgagactc        60
tcctgtgcag cctctggaag catcgccagt atcaatgcca tgggctggta ccgccaggct      120
ccagggaagc agcgcgagtt ggtcgcagct attactagag gtggtagcac aaactatgca      180
gactccgtga agggccgatt caccatctcc agagacaacg ccaagaacac ggtatatctg      240
caaatgaaca gcctgaaacc ggaggacacg gccgtctatt catgtaatgg tttgtgctca      300
gacgatcggt gttatgggga ctccctttt gcccctggg gcccggggac ccaggtcacc        360
gtctcctca                                                              369
```

<210> SEQ ID NO 190
<211> LENGTH: 354
<212> TYPE: DNA
<213> ORGANISM: artificial sequence
<220> FEATURE:
<223> OTHER INFORMATION: G24 nucleotide sequence

<400> SEQUENCE: 190

```
gaggtacagc tggtggaatc tgggggagga ttggtgcagc ctgggggtc tctgagactg        60
tcctgtctag tctctggaag gggcgtcagt ctcgatgccg tgggctggtc gcgcgtggct      120
ccagggaagc agcgcgactt cgtcgcacgt attgatagta ggggtagcgc atactatgca      180
gactccgtag agggccgatt caccatctcc agagacaacg ccaagaacac ggtgtatctg      240
caagtggaca cgctgaaacc tgaggacacg gccgtctatt attgttttgc gtactacggg      300
gctcaaatat cttttggtcc gtggggccag gggacccagg tcaccgtctc ttca            354
```

<210> SEQ ID NO 191
<211> LENGTH: 405
<212> TYPE: DNA
<213> ORGANISM: artificial sequence
<220> FEATURE:
<223> OTHER INFORMATION: G19 nucleotide sequence

<400> SEQUENCE: 191

```
gatgtgcagc tgcaggcgtc tgggggagga ttggtgcagc ctgggggtc tctgagactg        60
tcctgtgtag tctctggaag gggcgtcaat ctcgatgcca tgggctggtc gcgcgtggct      120
ccagggaagc agcgcgactt cgtcgcacat attgatgata gggtaccgc atactatgca       180
gacttcgtaa agggccgatc caccatctcc agagacaacg ccaagaacac ggtgtatctg      240
caagtggaca cgctgaaacc tgaggacacg gccgtctatt attgctttgc gtggcagggt      300
gcggaaacat attggggcct ggggacccgg gtcaccgtct cctcaggatc cgaaccaaaa      360
ctgatcaacg aagaacatct gaaccatcac catcaccatt attga                      405
```

<210> SEQ ID NO 192
<211> LENGTH: 360
<212> TYPE: DNA
<213> ORGANISM: artificial sequence
<220> FEATURE:
<223> OTHER INFORMATION: G5-1 nucleotide sequence

<400> SEQUENCE: 192

```
gaggtacagc tggtggaatc tgggggaggc ttggtgcagg ctgggggtc tctgagactc        60
tcctgtgtag cctctggaag catcttcagt gtcaatgccg tggcctggta ccgccaggct      120
ccagggaaac agcgcgagtt ggtcgcatat atacgtcgta gtggtagcac aaactatgca      180
gactccgtga agggccgatt caccatctcc agagacaatg ccaagaacac gctgtatctg      240
```

```
caaatgaaca gcctgaaacc tgacgacaca gccgtgtatt attgtaatgc ggggcggaca    300
ggggatcgtt ttaatttggt ggcgtattgg ggccagggga cccaggtcac cgtctcctca    360
```

<210> SEQ ID NO 193
<211> LENGTH: 369
<212> TYPE: DNA
<213> ORGANISM: artificial sequence
<220> FEATURE:
<223> OTHER INFORMATION: G26 nucleotide sequence

<400> SEQUENCE: 193

```
gaggtacagc tggtggaatc tggggagga ttggcgcagg ctgggggctc tctgagactc    60
tcctgtacag cctctggacg caccttcagt acctatttca tggcctggtt ccgccagcct   120
ccagggaaag agcgtgaata cgtaggcggt attaggtgga gtgatggtgt tccacactat   180
gcagactccg tgaagggccg attcaccatc tccagagaca cgccaagaa cacggtgtat    240 ttgcaaatga acagcctgaa acctgaggac acggccgtct attactgcaa tgcagattac   300
tccccgcccg cagccggtt ccctgactta ggtccctggg gccaggggac ccaggtcacc    360
gtctcctca                                                            369
```

<210> SEQ ID NO 194
<211> LENGTH: 356
<212> TYPE: DNA
<213> ORGANISM: artificial sequence
<220> FEATURE:
<223> OTHER INFORMATION: G27 nucleotide sequence

<400> SEQUENCE: 194

```
gaggtgcagc tgcaggcgtc tggggaggc ttggtgcagc ctgggggtc tctgagactc     60 tcctgtgtag cctctggaag catcttcagt atcaaagcca tggcctggta ccgccaggct   120
ccagggaagc agcgcgagtt ggtcgcatac attcgtagtg gtggtacgac aaactatgca   180
gactccgtga agggccgatt caccatctcc agagacatcg ccaagaacac ggtgtatctg   240
caaatgaaca gcctgaaatc tgaggacacg ccgtttatt tttgtgcatc acggggtatt    300
gcggatggat ctgctttggt tcctacggcc aggggaccca ggtcaccgtc tcctca        356
```

<210> SEQ ID NO 195
<211> LENGTH: 366
<212> TYPE: DNA
<213> ORGANISM: artificial sequence
<220> FEATURE:
<223> OTHER INFORMATION: G1-2 nucleotide sequence

<400> SEQUENCE: 195

```
gaggtacagc tggtggaatc tgggggaggc ttggtgcagg ctgggcctc cgtgagactc     60 tcctgtgcag cctctggacg cgccaacagt ttgtatgcca tgggctggtt ccgccaggct   120
ccagggaagc agcgcgagtt ggtcgcatac attcgtagtg gtggtacgac aaactatgca   180
gactccgtga agggccgatt caccatctcc agagacatcg ccaagaacac ggtgtatctg   240
caaatgaaca gcctgaaacc tgaggacacg ccgtctatt actgcaatgc agattactcc    300
ccgcccggca gccggttccc tgacttaggt ccctggggcc aggggaccca ggtcaccgtc   360
tcctca                                                               366
```

<210> SEQ ID NO 196
<211> LENGTH: 372
<212> TYPE: DNA

<213> ORGANISM: artificial sequence
<220> FEATURE:
<223> OTHER INFORMATION: G28 nucleotide sequence

<400> SEQUENCE: 196

| | | | | | |
|---|---|---|---|---|---|
| gaggtacagc | tggtggaatc | tgggggagga | ttggtgcaaa | ttggggactc | tgtgagactc | 60 |
| tcctgtatag | cctctggagg | caccttcaga | acttatgcta | tgggttggtt | ccgccaggct | 120 |
| ccaggggctg | agcgtgaatt | tgtagctgcc | attagccggc | gcggtaataa | gacagattat | 180 |
| gcagagtccg | tgaagggccg | attcacagtc | tccagagaca | acgccgagaa | tacggtgtat | 240 |
| ttgcaaatga | acagcctgaa | acctgatgac | atgggcgttt | attactgtgc | agcgtcggcg | 300 |
| cgtaatttca | tcggcaccca | gccacttgat | tatgactact | ggggccaggg | gacccaggtc | 360 |
| accgtctcct | ca | | | | | 372 |

<210> SEQ ID NO 197
<211> LENGTH: 360
<212> TYPE: DNA
<213> ORGANISM: artificial sequence
<220> FEATURE:
<223> OTHER INFORMATION: G29 nucleotide sequence

<400> SEQUENCE: 197

| | | | | | |
|---|---|---|---|---|---|
| caggtaaagc | tggaggagtc | tgggggagga | atggtgcagg | ctgggggctc | tctgagactc | 60 |
| tcctgtgtag | cctctggacg | ctccttcgtt | ggctatttca | tggcctggtt | ccgccagcct | 120 |
| ccagggaaag | agcgtgaata | cgtaggcggt | attaggtgga | gtgatggtgt | tccacactat | 180 |
| gcagactccg | tgaagggccg | attcaccatc | tccagagaca | acgccaagaa | cacggtgtat | 240 |
| ttgcaaatga | acagcctgaa | atctgaggac | acggccgttt | attttgtgc | atcacggggt | 300 |
| attgcggatg | gatctgactt | tggttcctac | ggccagggga | cccaggtcac | cgtctcctca | 360 |

<210> SEQ ID NO 198
<211> LENGTH: 366
<212> TYPE: DNA
<213> ORGANISM: artificial sequence
<220> FEATURE:
<223> OTHER INFORMATION: G2-1 nucleotide sequence

<400> SEQUENCE: 198

| | | | | | |
|---|---|---|---|---|---|
| gaggtacagc | tggtggaatc | tgggggaggc | ttggtgcagc | ctgggggtc | tctgagactc | 60 |
| tcctgtgcag | cctctggaag | catcttcagt | atcaatgcca | tgggctggta | ccgccaggct | 120 |
| ccagggaagc | agcgcgaatt | ggtcgcagct | attactaaaa | gtaataacat | aaactatgca | 180 |
| gactccgtga | agggccgatt | caccatctcc | agagacaacg | ccaagaacac | ggtgtatctg | 240 |
| caaatgaaca | gcctgaaacc | tgaggacacg | gccgtctatt | attgtaatgg | attcttcact | 300 |
| ttgcctgggt | acagtagtga | agaatttggt | ccctggggcc | tggggaccca | ggtcaccgtc | 360 |
| tcctca | | | | | | 366 |

<210> SEQ ID NO 199
<211> LENGTH: 21
<212> TYPE: DNA
<213> ORGANISM: artificial sequence
<220> FEATURE:
<223> OTHER INFORMATION: YF-1

<400> SEQUENCE: 199

| | |
|---|---|
| cgccatcaag gtaccagttg a | 21 |

```
<210> SEQ ID NO 200
<211> LENGTH: 29
<212> TYPE: DNA
<213> ORGANISM: artificial sequence
<220> FEATURE:
<223> OTHER INFORMATION: YF-2

<400> SEQUENCE: 200
ggggtacctg tcatccacgg accagctga                                         29

<210> SEQ ID NO 201
<211> LENGTH: 43
<212> TYPE: DNA
<213> ORGANISM: Artificial Sequence
<220> FEATURE:
<223> OTHER INFORMATION: YBN
<220> FEATURE:
<221> NAME/KEY: variation
<222> LOCATION: (16)..(16)
<223> OTHER INFORMATION: S is G or C
<220> FEATURE:
<221> NAME/KEY: variation
<222> LOCATION: (17)..(17)
<223> OTHER INFORMATION: M is A or C
<220> FEATURE:
<221> NAME/KEY: variation
<222> LOCATION: (18)..(18)
<223> OTHER INFORMATION: K is G or T
<220> FEATURE:
<221> NAME/KEY: variation
<222> LOCATION: (21)..(21)
<223> OTHER INFORMATION: R is A or G
<220> FEATURE:
<221> NAME/KEY: variation
<222> LOCATION: (33)..(33)
<223> OTHER INFORMATION: K is G or T

<400> SEQUENCE: 201
cagccggcca tggccsmkgt rcagctggtg gaktctgggg gag                         43

<210> SEQ ID NO 202
<211> LENGTH: 41
<212> TYPE: DNA
<213> ORGANISM: artificial sequence
<220> FEATURE:
<223> OTHER INFORMATION: YV-BACK

<400> SEQUENCE: 202
catgtgcatg gcctagactc gcggcccagc cggccatggc c                           41

<210> SEQ ID NO 203
<211> LENGTH: 47
<212> TYPE: DNA
<213> ORGANISM: artificial sequence
<220> FEATURE:
<223> OTHER INFORMATION: YV-FOR

<400> SEQUENCE: 203
catgtgtaga ttcctggccg gcctggcctg aggagacggt gacctgg                     47

<210> SEQ ID NO 204
<211> LENGTH: 41
<212> TYPE: DNA
<213> ORGANISM: Artificial Sequence
<220> FEATURE:
<223> OTHER INFORMATION: 5' primer
<220> FEATURE:
<221> NAME/KEY: variation
<222> LOCATION: (21)..(21)
<223> OTHER INFORMATION: S is G or C
<220> FEATURE:
```

```
<221> NAME/KEY: variation
<222> LOCATION: (22)..(22)
<223> OTHER INFORMATION: V is G or A or C
<220> FEATURE:
<221> NAME/KEY: variation
<222> LOCATION: (23)..(23)
<223> OTHER INFORMATION: K is G or T
<220> FEATURE:
<221> NAME/KEY: variation
<222> LOCATION: (27)..(27)
<223> OTHER INFORMATION: M is A or C
<220> FEATURE:
<221> NAME/KEY: variation
<222> LOCATION: (34)..(34)
<223> OTHER INFORMATION: W is A or T
<220> FEATURE:
<221> NAME/KEY: variation
<222> LOCATION: (38)..(38)
<223> OTHER INFORMATION: K is G or T

<400> SEQUENCE: 204
gaagaagaag acaacaggcc svkgtgmagc tggwggaktc t          41

<210> SEQ ID NO 205
<211> LENGTH: 37
<212> TYPE: DNA
<213> ORGANISM: artificial sequence
<220> FEATURE:
<223> OTHER INFORMATION: 3' primer

<400> SEQUENCE: 205
gaagatctcc ggatcctgag gagacggtga cctgggt               37
```